US012692532B2

(12) United States Patent
Aronoff et al.

(10) Patent No.: US 12,692,532 B2
(45) Date of Patent: Jul. 28, 2026

(54) COMPOUNDS AND METHODS FOR AMINE OXIDASE IMAGING

(71) Applicant: ETH ZURICH, Zurich (CH)

(72) Inventors: Matthew Ronald Aronoff, Moenchaltorf (CH); Helma Wennemers, Zurich (CH)

(73) Assignee: ETH ZURICH, Zurich (CH)

( * ) Notice: Subject to any disclaimer, the term of this patent is extended or adjusted under 35 U.S.C. 154(b) by 916 days.

(21) Appl. No.: 17/782,479

(22) PCT Filed: Dec. 3, 2020

(86) PCT No.: PCT/EP2020/084462

§ 371 (c)(1),
(2) Date: Jun. 3, 2022

(87) PCT Pub. No.: WO2021/110834

PCT Pub. Date: Jun. 10, 2021

(65) Prior Publication Data

US 2023/0104758 A1 Apr. 6, 2023

(30) Foreign Application Priority Data

Dec. 5, 2019 (EP) .................................... 19213787

(51) Int. Cl.
*C12Q 1/26* (2006.01)
*C07D 311/16* (2006.01)
*G01N 21/64* (2006.01)

(52) U.S. Cl.
CPC .............. *C12Q 1/26* (2013.01); *C07D 311/16* (2013.01); *C12Y 104/03006* (2013.01); *G01N 21/6428* (2013.01); *G01N 2021/6439* (2013.01); *G01N 2333/90638* (2013.01)

(58) Field of Classification Search
CPC ................................ C12Q 1/26; C07D 311/16
See application file for complete search history.

(56) References Cited

FOREIGN PATENT DOCUMENTS

| | | | |
|---|---|---|---|
| EP | 0411912 | A2 | 2/1991 |
| EP | 0424525 | A1 | 5/1991 |
| WO | WO 2007/050810 | A2 | 5/2007 |

OTHER PUBLICATIONS

Altschul SF, Gish W, Miller W, Myers EW, Lipman DJ. Basic local alignment search tool. J Mol Biol. Oct. 5, 1990;215 (3):403-10. doi: 10.1016/S0022-2836(05)80360-2. PMID: 2231712.
Barker, H., Cox, T. & Erler, J. The rationale for targeting the LOX family in cancer. Nat Rev Cancer 12, 540-552 (2012). https://doi.org/10.1038/nrc3319.
Chang D, Kim KT, Lindberg E, Winssinger N. Accelerating Turnover Frequency in Nucleic Acid Templated Reactions. Bioconjug Chem. Jan. 17, 2018;29(1):158-163. doi: 10.1021/acs.bioconjchem.7b00663. Epub Dec. 12, 2017. PMID: 29178795.
Engel, J, et al., The triple helix ⇌ coil conversion of collagen-like polytripeptides in aqueous and nonaqueous solvents. Comparison of the thermodynamic parameters and the binding of water to (L-Pro-L-Pro-Gly)n and (L-Pro-L-Hyp-Gly)n, BiopolymersVolume 16, Issue 3 p. 601-622, Mar. 1977.
Frank, Sabine, et al., Stabilization of short collagen-like triple helices by protein engineering, JMB, Mar. 22, 2001, 308, 1081-1089.
Arkin MA, Blackshields G, Brown NP, Chenna R, McGettigan PA, McWilliam H, Valentin F, Wallace IM, Wilm A, Lopez R, Thompson JD, Gibson TJ, Higgins DG. Clustal W and Clustal X version 2.0. Bioinformatics. Nov. 1, 2007;23 (21):2947-8. doi: 10.1093/bioinformatics/btm404. Epub Sep. 10, 2007. PMID: 17846036.
Palamakumbura, A., et al., Fluorometric Assay for Detection of Lysyl Oxidase Enzyme Activity in Biological Samples, halytical Biochemistry, vol. 300, Issue 2, Jan. 2002, pp. 245-251, ISSN 0003-2697.
International Search Report and Written Opinion for PCT/EP2020/084462 dated Sep. 29, 2021.
Farina, Roberta, et al., Structure-based Design and Optimization of Multitarget-Directed 2 H-Chromen-2-one Derivatives as Potent Inhibitors of Manoamine Oxidase B and Cholinestrerases, Journal of Medicinal Chemistry, vol. 58, No. 14, pp. 5561-5578, Jul. 9, 2015.

*Primary Examiner* — Golam M Shameem
(74) *Attorney, Agent, or Firm* — Bryan D. Zerhusen, Esq.; Nicholas R. Herrel, Esq.; CANTOR COLBURN LLP

(57) ABSTRACT

The invention pertains to a functionalizable and enzyme-activatable fluorescent probe and methods for monitoring the activity of amine oxidases. Amine oxidases catalyze the oxidative deamination, e.g. of the ε-amine of a lysine to an aldehyde which in turn can form covalent bonds with neighboring side chains, e.g. in the context of collagen cross-linking. Amine oxidase activity can be correlated with collagen-associated diseases including pulmonary and hepatic fibrosis, cardiomyopathy and tumor metastasis.

19 Claims, 37 Drawing Sheets

Specification includes a Sequence Listing.

COMPOUNDS AND METHODS FOR AMINE OXIDASE IMAGING

CROSS-REFERENCE TO RELATED APPLICATIONS

The present application is a National Stage Entry of PCT/EP2020/084462, filed 3 Dec. 2020, published as WO 2021/110834 A2, which claims the benefit of and priority to EP Application 19213787.5, filed 5 Dec. 2019, each of which is incorporated herein by reference in its entirety.

INCORPORATION BY REFERENCE

In compliance with 37 C.F.R. § 1.52(e)(5), the sequence information contained in electronic file name: 50794PCT_Sequence_ST25.txt; size 21.5 KB; created on: 3 Dec. 2020; using Patent-In 3.5.1, and Checker 4.4.6 is hereby incorporated herein by reference in its entirety.

FIELD OF THE INVENTION

The invention pertains to a functionalizable and enzyme-activatable fluorescent probe and methods for monitoring the activity of amine oxidases. Amine oxidases catalyze the oxidative deamination, e.g. of the ε-amine of a lysine to an aldehyde which in turn can form covalent bonds with neighboring side chains, e.g. in the context of collagen cross-linking. Amine oxidase activity can be correlated with collagen-associated diseases including pulmonary and hepatic fibrosis, cardiomyopathy and tumor metastasis.

BACKGROUND OF THE INVENTION

Amine oxidases are enzymes that catalyze the oxidative cleavage of alkylamines into aldehydes and ammonia, e.g. the oxidative deamination of the ε-amine of a lysine to an aldehyde. There are two subfamilies of amine oxidases characterized by the cofactor they contain. Representative amine oxidases with copper as cofactor are lysyl oxidase (LOX), primary-amine oxidase (e.g. AOC2, AOC3) and diamine oxidase (AOC1). Representative monoamine oxidases with flavin as cofactor are monoamine oxidases A and B (MAOA and MAOB).

Collagen is an essential protein that provides mechanical strength to skin and other tissues. The cross-linking of collagen gives rise to many of the macroscopic structural qualities of collagen, such as tensile strength and proteolytic resistance. This cross-linking occurs post-translationally by amine oxidases, e.g. LOX, which form covalent bonds with adjacent amino acid strands of collagen. Cross-linking can occur as a normal mechanism, e.g. during tissue maturation, growth and development as well as for wound healing. However, increases in amine oxidase activity, e.g. LOX activity, are correlated with a number of diseases and disorders including fibrosis, cardiomyopathy and cancer.

Existing probes for amine oxidases, e.g. for LOX, do not enable synthetic functionalization which is necessary for controlling the localization, spatial accumulation and site of action of the probe, e.g. in cells or tissues, also in the context of diagnosis. Furthermore, existing fluorescent probes for other enzymes share a low quantum yield.

Aslam et al. (Chemical Science 2015, 6, 4946-4953) disclose a fluorescent probe to visualize LOX activity. However, this probe exhibits a poor fluorescence increase upon unmasking and cannot be functionalized for diagnostic purposes.

The objective technical problem underlying the present invention is the provision of a new compound and method for detecting amine oxidase activity.

SUMMARY OF THE INVENTION

In a first aspect, the present invention is directed to a compound according to Formula I Formula I

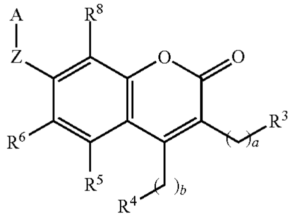

wherein

- a and b are independently an integer from 0 to 10, optionally 1 or 2;
- A is a structure selected from the group consisting of

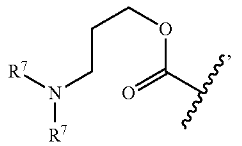

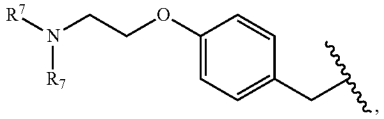

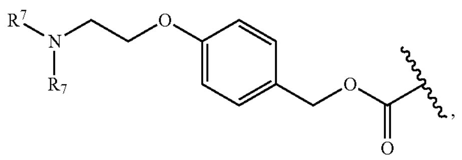

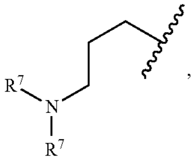

,

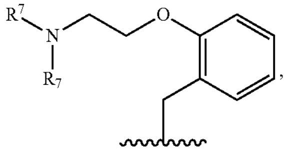

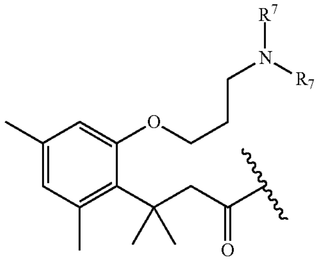

and

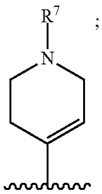

;

$R^3$ and $R^4$ are independently selected from the group consisting of
—$NHR^{9'}$, —$OR^{9'}$, $SR^{9'}$,

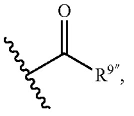 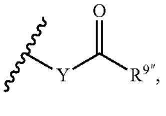

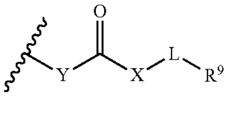 and 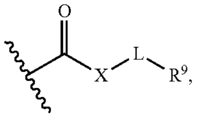

optionally —$SR^9$ when a is 0 to 3;

linear or branched, substituted or non-substituted $(C_{1-10})$ alkyl, optionally methyl, ethyl and propyl, $(C_{2-10})$alkenyl and $(C_{2-10})$alkynyl, substituted or non-substituted carbocycle selected from the group consisting of $(C_{3-10})$carbocycle, optionally aromatic $(C_6)$carbocycle, optionally if a and/or b are/is 0;

substituted or non-substituted triphenylphosphine connected via the phosphorous;

N-maleimidyl; and halogens, optionally F, Cl, Br and I, optionally if one of $R^3$ or $R^4$ is a proteinogenic amino acid, a non-proteinogenic amino acid or a peptide, the other of $R^3$ or $R^4$ is a halogen, optionally F, Cl, Br or I;

L is absent or a linker, optionally a linker selected from the group consisting of linear or branched, substituted or non-substituted $(C_{1-10})$alkyl, optionally propyl, butyl and pentyl, $(C_{2-10})$alkenyl and $(C_{2-10})$alkynyl;

a $(C_{1-10})$ alkyl comprising one or more amide functionalities in the alkyl chain, optionally

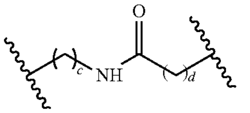 or

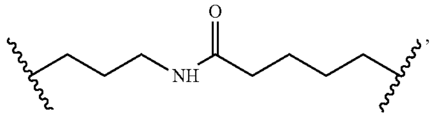

wherein c and d are independently selected from 1, 2, 3, 4, and 5; and linear or branched, substituted or non-substituted $(C_{1-20})$ alkyl ether, optionally a polyethylene glycol (PEG) chain, optionally a PEG chain with 1 to 10 ethylene oxide entities, $(C_{2-10})$alkenyl ether, $(C_{2-10})$alkynyl ether and $(C_{4-10})$carbocyclic ether;

X, Y and Z are independently selected from the group consisting of O, N and S, optionally Z is selected from the group consisting of O and N, optionally Z is O;

$R^{9'}$ is selected from the group consisting of hydrogen;

linear or branched, substituted or non-substituted, optionally sulfonated, $(C_{1-10})$alkyl, optionally methyl, ethyl and propyl, $(C_{2-10})$alkenyl and $(C_{2-10})$ alkynyl;

linear or branched, substituted or non-substituted $(C_{1-20})$alkyl ether, optionally a polyethylene glycol (PEG) chain, optionally a PEG chain with 1 to 10 ethylene oxide entities, $(C_{2-10})$alkenyl ether, $(C_{2-10})$ alkynyl ether and $(C_{4-10})$carbocyclic ether;

substituted or non-substituted carbocycle selected from the group consisting of $(C_{3-10})$-carbocycle, optionally aromatic $(C_6)$carbocycle, optionally a carbocycle substituted by a substituent selected from the group consisting of Cl, F, Br, substituted or non-substituted methyl, optionally —$(CF_3)$, ethyl, propyl and cyclopropyl;

substituted or non-substituted triphenylphosphine connected via the phosphorous;

substituted or non-substituted $(C_{3-6})$heterocycle and $(C_7\text{-}C_{10})$carbo- or heterobicycle having 1 to 3 heteroatoms each independently selected from N, O and S, optionally substituted or non-substituted $(C_7)$heterobicycle having 2 heteroatoms selected from N and S;

a proteinogenic amino acid, a non-proteinogenic amino acid, optionally an aminooxy or hydrazide derivative of a proteinogenic or non-proteinogenic amino acid, optionally lysine, proline, glycine, 4-hydroxyproline, 4-aminoproline, and 4-aminooxyproline;

a peptide, optionally comprising 1 to 2000, optionally 1 to 100, optionally 1 to 25 amino acids, optionally a peptide comprising 1 to 10, optionally 7 [proline]-[4-hydroxyproline]-[glycine] units;

a collagen peptide, fibronectin peptide, fibrillin peptide, elastin peptide and an RGD (arginylglycylaspartic acid) peptide; and an antibody, optionally an anti-collagen, anti-elastin, anti-fibronectin and anti-fibrillin antibody;

$R^9$ is selected from residues defined for $R^{9'}$ and is further selected from the group consisting of azide, N-maleimidyl, —$NH_2$, —OH and —$SH_2$;

$R^{9''}$ is selected from the group consisting of halogens, optionally F, Cl, Br and I, substituted or non-substituted triphenylphosphine connected via the phosphorous, azide, —$SR^{10}$,

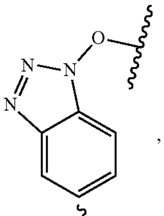 , 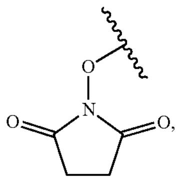

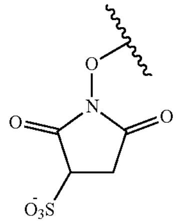 and 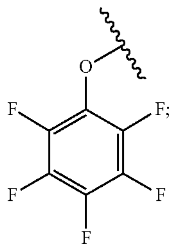

$R^{10}$ is selected from the group consisting of linear or branched, substituted or non-substituted $(C_{1-10})$alkyl, optionally methyl, ethyl and propyl, $(C_{2-10})$alkenyl and $(C_{2-10})$alkynyl; and linear or branched, substituted or non-substituted $(C_{1-20})$alkyl ether, optionally a polyethylene glycol (PEG) chain, optionally a PEG chain with 1 to 10 ethylene oxide entities, $(C_{2-10})$alkenyl ether, $(C_{2-10})$ alkynyl ether and $(C_{4-10})$carbocyclic ether;

$R^5$ is selected from the group consisting of
hydrogen and —OH; and
halogens, optionally F, Cl, Br and I;

$R^6$ and $R^8$ are independently selected from the group consisting of hydrogen, —OH, halogens, optionally F, Cl, Br and I; and/or $R^7$ is each independently selected from the group consisting of
hydrogen;
linear or branched, substituted or non-substituted $(C_{1-10})$alkyl, optionally methyl, ethyl and propyl, $(C_{2-10})$ or $(C_{3-10})$alkenyl and $(C_{2-10})$ or $(C_{3-10})$alkynyl;
linear or branched, substituted or non-substituted $(C_{1-20})$alkyl ether, optionally a polyethylene glycol (PEG) chain, optionally a PEG chain with 1 to 10 ethylene oxide entities, $(C_{2-10})$alkenyl ether, $(C_{2-10})$ alkynyl ether and $(C_{4-10})$carbocyclic ether;
—$N_2$ forming an azide with the nitrogen atom of A; and
tert-Butyloxycarbonyl (Boc), 9-fluorenylmethoxycarbonyl (Fmoc), benzyloxycarbonyl (Cbz), acetyl (Ac), trifluoroacetic acid (TFA), phthalimide, benzyl (Bn), triphenylmethyl (Tr), benzylidene, or para-toluenesulfonyl (Ts);

and salts and solvates thereof, optionally physiologically acceptable salts and solvates.

Without wishing to be bound by theory, the cleavable masking group A-Z of the present compounds masks the fluorescence of the fluorescent probe until cleavage by an amine oxidase (see scheme below for a representative example, LOX=lysyl oxidase). Furthermore, the cleavage leads to a shift in the emission wavelength of the compounds which allows to discriminate between the unaltered probe and the probe that is deaminated by an amine oxidase.

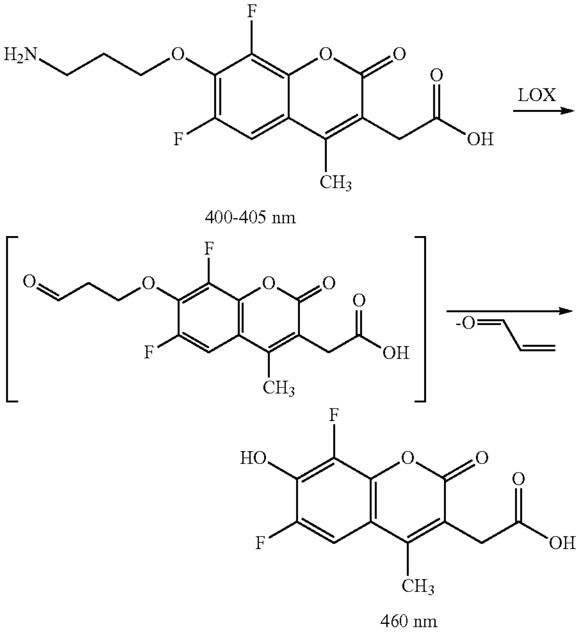

For example, the enzyme-cleavable masking group A-Z of the compounds described herein greatly reduces quantum yield, e.g. by a factor of more than 10, while the functionalization possibilities provide a platform for introducing the fluorescent probe into collagen model peptides, e.g. for in vivo imaging of collagen-associated processes (e.g. wound healing, see Example 16 and FIGS. 31 and 40 to 44). Furthermore, the compounds can also be, e.g., attached to specific targeting moieties such as, e.g., antibodies which direct the compounds to the desired location.

The compounds described herein feature a significant shift in excitation wavelength. For example, when masked, the wavelength is shifted from a maximum to a shorter wavelength such that the fluorescence characteristics of the compound are efficiently masked under a normal excitation wavelength, e.g. used for fluorescence microscopy or other means of detection (e.g. 400-405 nm). When unmasked, e.g. by an amine oxidase enzyme, the excitation wavelength is shifted essentially to that of the fluorophore core of the compounds, whereby enzyme activity and localization can be determined (see, e.g. FIGS. 1 and 2). In comparison to state of the art probes (e.g. oLOX probe of Aslam et al., Chemical Science 2015, 6, 4946-4953) the compounds of the present invention unexpectedly show a significantly higher (e.g. 4-fold higher) increase in fluorescence upon unmasking by an amine oxidase while not showing any background fluorescence before unmasking (see, e.g., FIG. 13).

Furthermore, functionalization of the compounds can be easily done due to the presence of functional groups such as, e.g., esters which can react with any molecule exhibiting a nucleophile such as, e.g., an alcohol or amine. Alternatively, a nucleophilic residue of the compounds described herein can be reacted with an electrophilic group of a target, e.g. an amino acid sequence or a protein. The compounds according to the present invention specifically detect amine oxidase activity of different amine oxidases in vitro (see, e.g., FIGS. 11, 12, 13 and 34), ex vivo (see, e.g., FIGS. 3 to 5, 8 to 10, 13 and 35 to 39) and in vivo (see, e.g., FIGS. 31 and 40 to 44).

The compounds of the present may comprise residues, e.g. functional groups, that are protected, e.g. by protecting groups used in organic chemistry or peptide chemistry. The compounds described herein can be installed into a peptide, e.g. a synthetic peptide, by applying common peptide synthetic strategies such as Fmoc/t-Bu peptide synthesis protocols which are compatible with but not limited to all stages of peptide synthesis.

In an embodiment, the compound of the present invention is one, wherein

A is a structure selected from the group consisting of

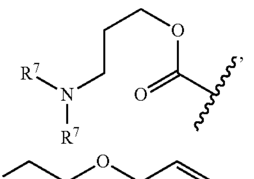

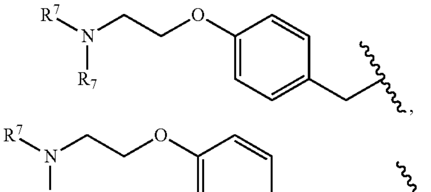

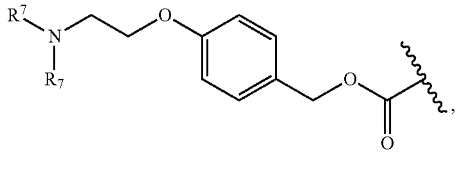

-continued

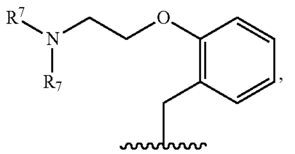

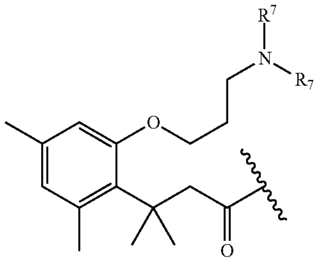

and

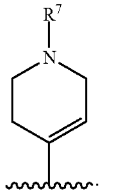

In an embodiment, the compound of the present invention is one, wherein $R^3$ is

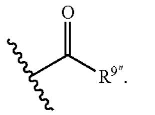

In an embodiment, the compound of the present invention is one, wherein $R^3$ is

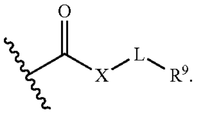

In an embodiment, the compound of the present invention is one, wherein a and b are independently an integer from 0 to 3, optionally 1 or 2;

A is a structure selected from the group consisting of

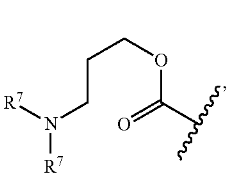

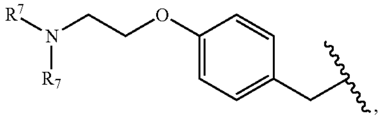

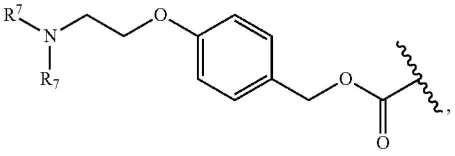

-continued

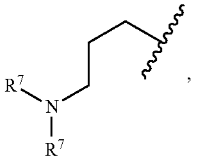

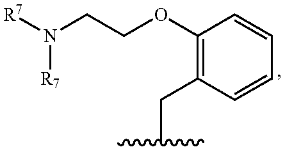

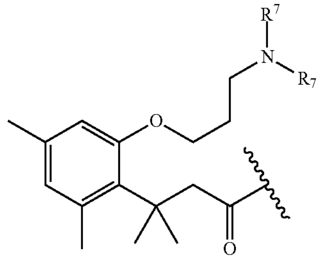

and

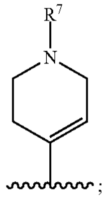

$R^3$ and $R^4$ are independently selected from the group consisting of

—$NHR^{9'}$, —$OR^{9'}$, $SR^{9'}$,

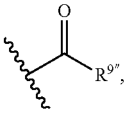

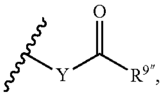

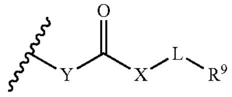

and

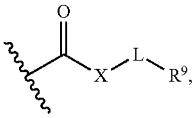

optionally —$SR^{9'}$ when a is 0 to 3;

linear or branched, substituted or non-substituted ($C_{1-10}$) alkyl, optionally methyl, ethyl and propyl, optionally if a and/or b are/is 0;

triphenylphosphine connected via the phosphorous;

N-maleimidyl; and halogens, optionally F, Cl, Br and I, optionally if one of $R^3$ or $R^4$ is a proteinogenic amino acid, a non-proteinogenic amino acid or a peptide, the other of $R^3$ or $R^4$ is a halogen, optionally F, Cl, Br or I;

L is absent or a linker, optionally a linker selected from the group consisting of linear or branched, substituted or non-substituted ($C_{1-10}$)alkyl, optionally propyl, butyl and pentyl

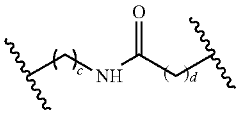

or

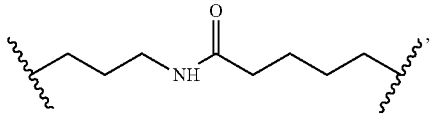

wherein c and d are independently selected from 1, 2, 3, 4, and 5; and linear or branched, substituted or non-substituted ($C_{1-20}$) alkyl ether, optionally a polyethylene glycol (PEG) chain, optionally a PEG chain with 1 to 10 ethylene oxide entities;

X, Y and Z are independently selected from the group consisting of O, N and S, optionally Z is selected from the group consisting of O and N, optionally Z is O;

$R^{9'}$ is selected from the group consisting of hydrogen;

linear or branched, substituted or non-substituted, optionally sulfonated, $(C_{1-10})$alkyl, optionally methyl, ethyl and propyl, $(C_{2-10})$alkenyl and $(C_{2-10})$alkynyl;

linear or branched, substituted or non-substituted $(C_{1-20})$alkyl ether, optionally a polyethylene glycol (PEG) chain, optionally a PEG chain with 1 to 10 ethylene oxide entities;

triphenylphosphine connected via the phosphorous;

a proteinogenic amino acid, a non-proteinogenic amino acid, optionally an aminooxy or hydrazide derivative of a proteinogenic or non-proteinogenic amino acid, optionally lysine, proline, glycine, 4-hydroxyproline, 4-aminoproline, and 4-aminooxyproline;

a peptide, optionally comprising 1 to 2000, optionally 1 to 100, optionally 1 to 25 amino acids, optionally a peptide comprising 1 to 10, optionally 7 [proline]-[4-hydroxyproline]-[glycine] units;

a collagen peptide, fibronectin peptide, fibrillin peptide, elastin peptide and an RGD (arginylglycylaspartic acid) peptide; and an antibody, optionally an anti-collagen, anti-elastin, anti-fibronectin and anti-fibrillin antibody;

$R^9$ is selected from residues defined for $R^{9'}$ and is further selected from the group consisting of azide, N-maleimidyl, —$NH_2$, —OH and —$SH_2$;

$R^{9''}$ is selected from the group consisting of azide, —$SR^{10}$,

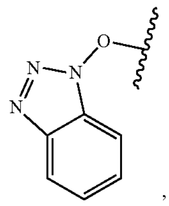
,
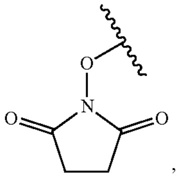
,
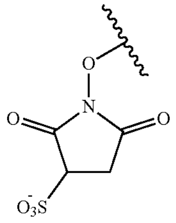
and
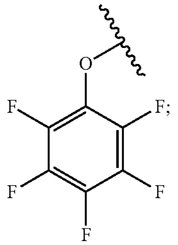

$R^{10}$ is selected from the group consisting of linear or branched, substituted or non-substituted $(C_{1-10})$alkyl, optionally methyl, ethyl and propyl; and linear or branched, substituted or non-substituted $(C_{1-20})$alkyl ether, optionally a polyethylene glycol (PEG) chain, optionally a PEG chain with 1 to 10 ethylene oxide entities;

$R^5$ is selected from the group consisting of hydrogen and —OH; and halogens, optionally F, Cl, Br and I;

$R^6$ and $R^8$ are independently selected from the group consisting of hydrogen, halogens, optionally F, Cl, Br and I; and/or $R^7$ is each independently selected from the group consisting of hydrogen;

linear or branched, substituted or non-substituted $(C_{1-10})$alkyl, optionally methyl, ethyl and propyl;

linear or branched, substituted or non-substituted $(C_{1-20})$alkyl ether, optionally a polyethylene glycol (PEG) chain, optionally a PEG chain with 1 to 10 ethylene oxide entities;

—$N_2$ forming an azide with the nitrogen atom of A; and

Boc, Fmoc, Cbz, Ac, TFA, phthalimide, Bn, Tr, benzylidene, and Ts;

In a further embodiment, the compound of the present invention is one, wherein a is an integer from 0 to 3, optionally 1 or 2;

b is 0;

A is a structure selected from the group consisting of

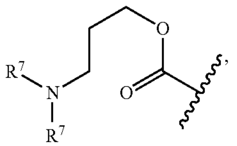
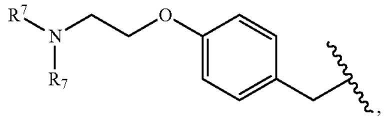
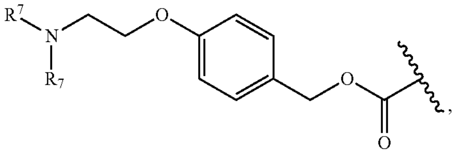
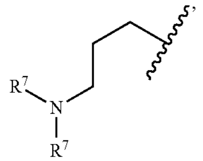
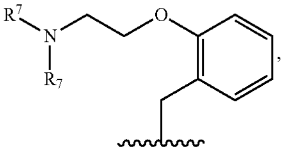
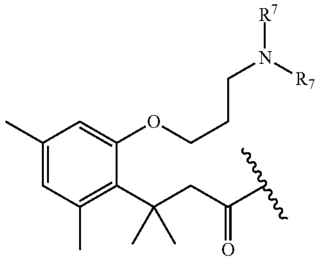
and
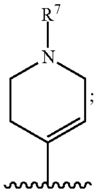
;

$R^3$ is

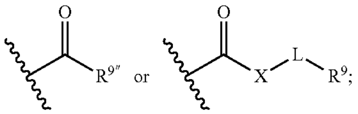

$R^4$ is hydrogen, linear or branched, substituted or non-substituted $(C_{1-10})$alkyl, optionally methyl, ethyl and propyl;

L is absent or a linker, optionally a linker selected from the group consisting of linear or branched, substituted or non-substituted $(C_{1-10})$alkyl, optionally propyl, butyl and pentyl;

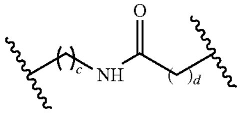

or

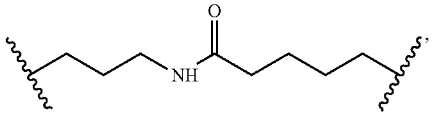

wherein c and d are independently selected from 1, 2, 3, 4, and 5; and linear or branched, substituted or non-substituted $(C_{1-10})$ alkyl ether, optionally a polyethylene glycol (PEG) chain, optionally a PEG chain with 1 to 10 ethylene oxide entities;

X is selected from the group consisting of O, N and S;

Z is O;

$R^9$ is selected from the group consisting of hydrogen, N-maleimidyl;

linear or branched, substituted or non-substituted $(C_{1-10})$alkyl, optionally methyl, ethyl and propyl, $(C_{2-10})$alkenyl and $(C_{2-10})$alkynyl;

linear or branched, substituted or non-substituted $(C_{1-20})$alkyl ether, optionally a polyethylene glycol (PEG) chain, optionally a PEG chain with 1 to 10 ethylene oxide entities;

triphenylphosphine connected via the phosphorous;

a proteinogenic amino acid, a non-proteinogenic amino acid, optionally lysine, proline, glycine, 4-hydroxyproline, 4-aminoproline, and 4-aminooxyproline;

a peptide, optionally comprising 1 to 2000, optionally 1 to 100, optionally 1 to 25 amino acids, optionally a peptide comprising 1 to 10, optionally 7 [proline]-[4-hydroxyproline]-[glycine] units;

a collagen peptide, fibronectin peptide, fibrillin peptide, elastin peptide and an RGD (arginylglycylaspartic acid) peptide;

an antibody, optionally an anti-collagen, anti-elastin, anti-fibronectin and anti-fibrillin antibody; and azide, —$NH_2$, —OH and —$SH_2$;

$R^{9''}$ is selected from the group consisting of azide, —$SR^{10}$,

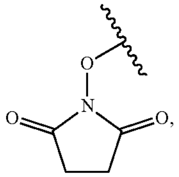

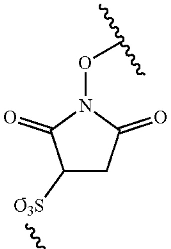

and

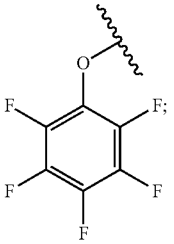

$R^{10}$ is selected from the group consisting of linear or branched, substituted or non-substituted $(C_{1-10})$alkyl, optionally methyl, ethyl and propyl, $(C_{2-10})$alkenyl and $(C_{2-10})$alkynyl;

$R^5$ is selected from the group consisting of hydrogen and —OH; and halogens, optionally F, Cl, Br and I;

$R^6$ and RB are independently selected from the group consisting of hydrogen, halogens, optionally F, Cl, Br and I; and/or $R^7$ is each independently selected from the group consisting of hydrogen;

linear or branched, substituted or non-substituted $(C_{1-10})$alkyl, optionally methyl, ethyl and propyl;

—$N_2$ forming an azide with the nitrogen atom of A; and

Boc, Fmoc and Cbz.

In another embodiment, the compound of the present invention is a compound according to Formula II Formula II

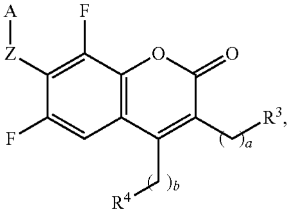

wherein a is 1 or 2;

b is 0;

A is a structure selected from the group consisting of

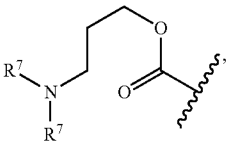

-continued

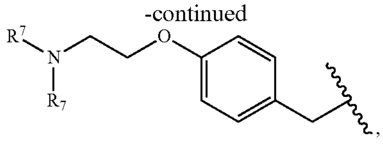,

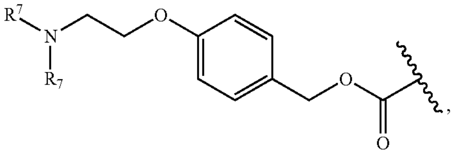,

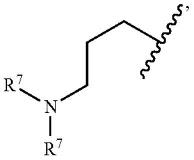

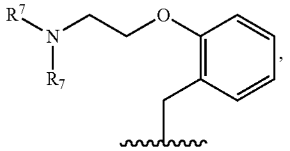,

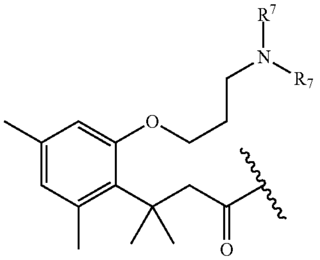 and

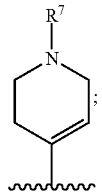;

$R^3$ is

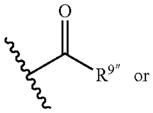 or 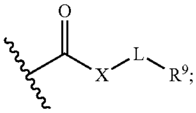;

$R^4$ is hydrogen, linear or branched, substituted or non-substituted $(C_{1-10})$alkyl, optionally methyl, ethyl and propyl;

L is absent,

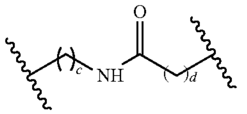 or

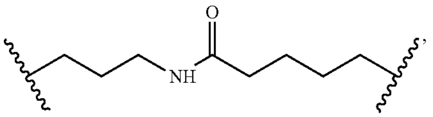

wherein c and d are independently selected from 1, 2, 3, 4, and 5;

X is selected from the group consisting of O and N;

Z is O;

$R^9$ is selected from the group consisting of hydrogen, N-maleimidyl;

linear or branched, substituted or non-substituted $(C_{1-10})$alkyl, optionally methyl, ethyl and propyl, triphenylphosphine connected via the phosphorous;

a proteinogenic amino acid, a non-proteinogenic amino acid, optionally lysine, proline, glycine, 4-hydroxyproline, 4-aminoproline, and 4-aminooxyproline;

a collagen peptide, fibronectin peptide, fibrillin peptide, elastin peptide and an RGD (arginylglycylaspartic acid) peptide; and azide, $—NH_2$, —OH and $—SH_2$;

$R^{9''}$ is selected from the group consisting of azide,

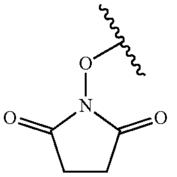 and 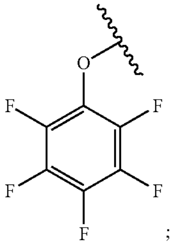;

and/or $R^7$ is each independently selected from the group consisting of hydrogen; and linear or branched, substituted or non-substituted $(C_{1-10})$alkyl, optionally methyl, ethyl and propyl.

Where a compound described herein exists in various tautomeric forms, a recited compound is not limited to any one specific tautomer, but rather is intended to encompass all tautomeric forms.

Recited compounds are further intended to encompass compounds in which one or more atoms are replaced with an isotope, i.e., an atom having the same atomic number but a different mass number. By way of general example, and without limitation, isotopes of hydrogen include tritium and deuterium and isotopes of carbon include $^{11}C$, $^{13}C$, and $^{14}C$.

As used herein, a "substituent" or "residue" or "R", refers to a molecular moiety that is covalently bound to an atom within a molecule of interest. For example, a "substituent", "R" or "residue" may be a moiety such as a halogen, alkyl group, haloalkyl group or any other substituent described herein that is covalently bonded to an atom, optionally a carbon, oxygen or nitrogen atom, that forms part of a molecule of interest.

The term "substituted" as used herein, means that any one or more hydrogens on the designated atom or group is replaced with a different atom than hydrogen, optionally by a halogen, optionally by fluorine, by a sulfonyl group, by a tertiary or quaternary amine or by a selection from the indicated substituents, provided that the designated atom's normal valence is not exceeded, and that the substitution results in a stable compound, i.e., a compound that can be isolated and characterized using conventional means. Optionally, "substituted" as used herein, means that any one or more hydrogens on the designated atom or group is replaced with a group that increases solubility of the compounds described herein, e.g. in water, aqueous buffers or physiological liquids such as, e.g. serum, saliva or blood. For example, substitution can be in the form of an oxygen bound to any chemical atom other than carbon, e.g. hydroxyl group, or an oxygen anion. When a substituent is oxo, i.e., =O, then 2 hydrogens on the atom are replaced. An oxo group that is a substituent of an aromatic carbon atom results in a conversion of —CH— to —C(=O)— and a loss of aromaticity. For example, a pyridyl group substituted by oxo is a pyridone.

For all aspects and embodiments of the present invention, $R^3$, $R^4$ and/or $R^9$ can be, e.g., selected from maleimide, resulting in the following exemplary structures:

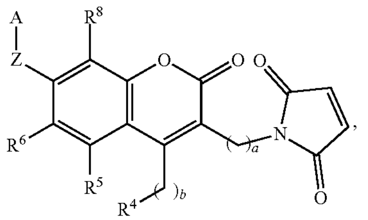

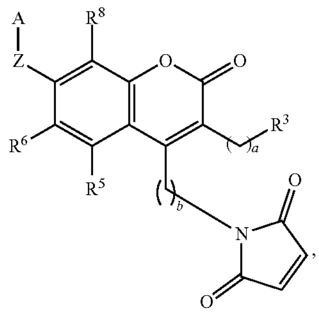

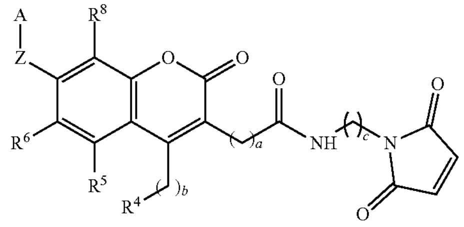

or

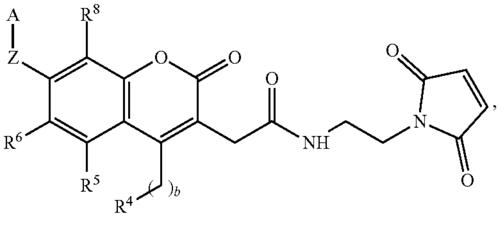

wherein all residues R, Z, A and the integers a, b and c are as defined herein and the residues shown for $R^3$ can also, e.g. instead, be selected for $R^4$.

The linker L as used herein for all aspects and embodiments, can be, e.g., a substituted or non-substituted ($C_{1-10}$) alkyl comprising one or more amide functionalities in the alkyl chain, i.e. wherein at least two carbon atoms are linked to each other via an amide bond, for example:

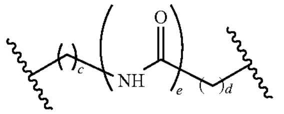

or

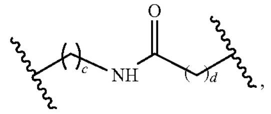

wherein e is selected from 1, 2 or 3 and c and d are independently selected from 1, 2, 3, 4, and 5. The linker L can either be attached to the structure of formulas I or II on the amine side of the amide or on the carbonyl side of the amide, optionally on the amine side, and to $R^9$ at the carbonyl side of the amine or the amine side of the amide, optionally at the carbonyl side, e.g. as follows:

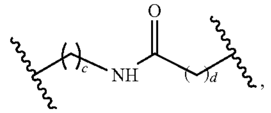

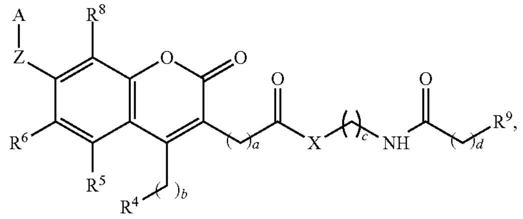

wherein X is as defined herein or optionally N, or

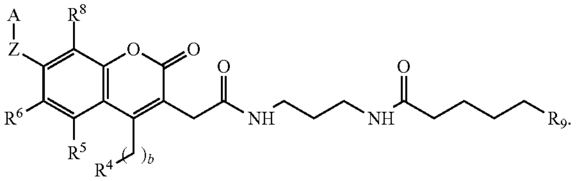

The triphenylphosphine moiety for $R^3$, $R^4$, $R^9$, $R^{9'}$ and $R^{9''}$ is attached at the phosphorous atom, i.e. as follows:

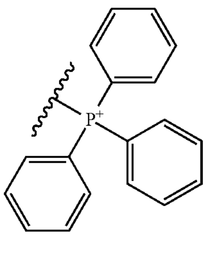 [SMILES: *[P+](c1ccccc1)(c1ccccc1)c1ccccc1]

and may be complemented by any suitable anion such as, e.g., a halogen anion, optionally $Cl^-$, $Br^-$, $I^-$ or trifluoroacetate. Also, the triphenylphosphine may be substituted or non-substituted, i.e. the phenyl rings of the triphenylphosphine moiety may be substituted or non-substituted, optionally by halogens.

Exemplary structures of triphenylphosphine-comprising compounds according to the present invention are shown below:

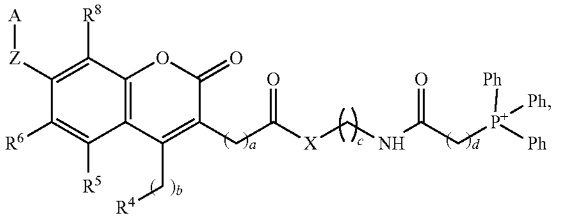

wherein X is as defined herein or optionally N; or, e.g.,

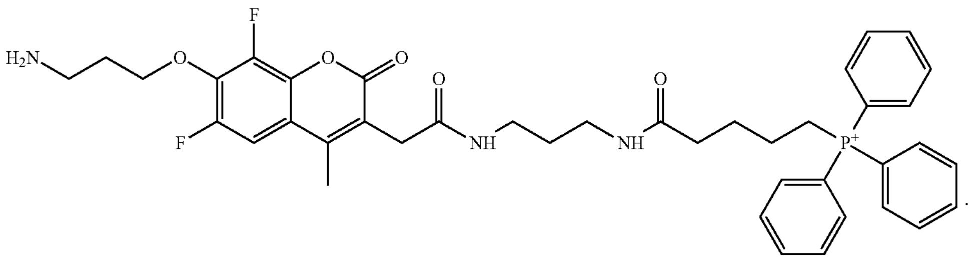 [SMILES: Cc1c(CC(=O)NCCCNC(=O)CCCC[P+](c2ccccc2)(c2ccccc2)c2ccccc2)c(=O)oc2c(F)c(OCCCN)c(F)cc12]

The terms "proteinogenic amino acid" as used herein, refers to any amino acid that is incorporated biosynthetically into proteins during translation, optionally lysine, proline and glycine. The term "non-proteinogenic amino acid", as used herein, refers to any amino acid that is not naturally encoded in the genetic code of any organism, for example D-amino acids, non-alpha amino acids, amino acids lacking a hydrogen on the alpha-carbon. Optionally, e.g. for R9' in all aspects of the present invention, proline, lysine, glycine or hydroxy, amino, aminooxy or hydrazide derivatives of proteinogenic or non-proteinogenic amino acids are encompassed for use in the present invention. Optionally, the derivatives can be selected from the group consisting of hydroxyproline, 4-hydroxyproline, cis-4-hydroxyproline, trans-4-hydroxyproline, 3-hydroxyproline, cis-3-hydroxyproline, trans-4-hydroxyproline, aminoproline, 4-aminoproline, cis-4-aminoproline, trans-4-aminoproline, 3-aminoproline, cis-3-aminoproline, trans-4-aminoproline, aminoxyproline, 4-aminoxyproline, cis-4-aminoxyproline, trans-4-aminoxyproline, 3-aminoxyproline, cis-3-aminoxyproline, trans-4-aminoxyproline, cis- or trans-4-hydrazinecarbonyl proline derivatives, optionally

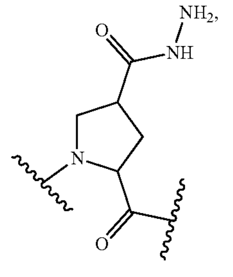 [SMILES: *C(=O)C1CC(C(=O)NN)CN1*]

and cis- or trans-4-hydrazinecarboxylate proline derivates, optionally

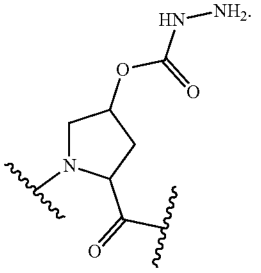 [SMILES: *C(=O)C1CC(OC(=O)NN)CN1*]

Optionally, e.g. for R9', in all aspects of the present invention, one or more proline-hydroxyproline-glycine or 4-proline-hydroxyproline-glycine units are preferred to mimic the structure of collagen.

The term "heteroatom" as used herein shall be understood to mean atoms other than carbon and hydrogen such as, e.g., O, N, S and P.

In the context of the present invention it is understood that antecedent terms such as "linear or branched", "substituted or non-substituted" indicate that each one of the subsequent terms is to be interpreted as being modified by said antecedent term. For example, the scope of the term "linear or branched, substituted or non-substituted alkyl, alkenyl, alkynyl, carbocycle" encompasses linear or branched, substituted or non-substituted alkyl; linear or branched, substituted or non-substituted alkenyl; linear or branched, substituted or non-substituted alkynyl; linear or branched, substituted or non-substituted alkylidene; and linear or branched, substituted or non-substituted carbocycle. For example, the term "($C_{2-10}$) alkenyl, alkynyl or alkylidene" indicates the group of compounds having 2 to 10 carbons and alkenyl, alkynyl or alkylidene functionality.

The expression "alkyl" refers to a saturated, straight-chain or branched hydrocarbon group that contains the number of carbon items indicated, e.g. "($C_{1-10}$)alkyl" denotes a hydrocarbon residue containing from 1 to 10 carbon atoms, e.g. a methyl, ethyl, propyl, iso-propyl, n-butyl, iso-butyl, sec-butyl, tert-butyl, n-pentyl, iso-pentyl, n-hexyl, 2,2-dimethylbutyl, etc.

The expression "alkenyl" refers to an at least partially unsaturated, substituted or non-substituted straight-chain or branched hydrocarbon group that contains the number of carbon atoms indicated, e.g. "($C_{2-10}$)alkenyl" denotes a hydrocarbon residue containing from 2 to 10 carbon atoms, for example an ethenyl (vinyl), propenyl (allyl), iso-propenyl, butenyl, isoprenyl or hex-2-enyl group, or, for example, a hydrocarbon group comprising a methylene chain interrupted by one double bond as, for example, found in monounsaturated fatty acids or a hydrocarbon group comprising methylene-interrupted polyenes, e.g. hydrocarbon groups comprising two or more of the following structural unit —[CH═CH—$CH_2$]—, as, for example, found in polyunsaturated fatty acids. Alkenyl groups have one or more, e.g. 1, 2, 3, 4, 5, or 6 double bond(s).

The expression "alkynyl" refers to at least partially unsaturated, substituted or non-substituted straight-chain or branched hydrocarbon groups that contain the number of carbon items indicated, e.g. "($C_{2-10}$)alkynyl" denotes a hydrocarbon residue containing from 2 to 10 carbon atoms, for example an ethinyl, propinyl, butinyl, acetylenyl, or propargyl group. Optionally, alkynyl groups have one or two (e.g. one) triple bond(s).

Furthermore, the terms "alkyl", "alkenyl" and "alkynyl" also refer to groups in which one or more hydrogen atom(s) have been replaced, e.g. by a halogen atom, optionally F, Cl or Br, such as, for example, a 2,2,2-trichloroethyl, tribromoethyl or a trifluoromethyl group.

The term "carbocycle" shall be understood to mean a substituted or non-substituted aliphatic hydrocarbon cycle containing the number of carbon items indicated, e.g. "($C_{3-10}$)carbocycle" or from 3 to 10, optionally from 3 to 6 carbon atoms, optionally 5 or 6 carbon atoms. These carbocycles may be either aromatic or non-aromatic systems. The non-aromatic ring systems may be mono- or polyunsaturated.

The term "carbobicycle" refers to a carbocycle as defined above comprising more than 1 ring, optionally two rings. Exemplary carbocycles and carbobicycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl, benzocycloheptenyl, spiro[4,5]decanyl, norbornyl, decalinyl, bicyclo[4.3.0]nonyl, tetraline, or cyclopentylcyclohexyl. The carbo- and/or carbobicyclic residue may be bound to the remaining structure of the complete molecule by any atom of the cycle, which results in a stable structure.

The term "carbocycle" shall also include "cycloalkyl" which is to be understood to mean aliphatic hydrocarbon-containing rings optionally having from 3 to 12 carbon atoms. These non-aromatic ring systems may be mono- or polyunsaturated, i.e. the term encompasses cycloalkenyl and cycloalkynyl.

The term "heterocycle" refers to a stable substituted or non-substituted, aromatic or non-aromatic, optionally 3 to 10 membered, optionally 3-6 membered, optionally 5 or 6 membered, monocyclic, heteroatom-containing cycle. Each heterocycle consists of carbon atoms and one or more, optionally 1 to 4, optionally 1 to 3 heteroatoms optionally chosen from nitrogen, oxygen and sulphur. A heterocycle may contain the number of carbon atoms in addition to the non-carbon atoms as indicated: a "($C_{3-6}$)heterocycle" is meant to have 3 to 6 carbon atoms in addition to a given number of heteroatoms.

The term "heterobicycle" refers to a heterocycle as defined above comprising more than 1 ring, optionally two rings.

The hetero- and/or heterobicyclic residue may be bound to the remaining structure of the complete molecule by any atom of the cycle, which results in a stable structure. Exemplary heterocycles and heterobicycles include, but are not limited to pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, 1-oxo-λ4-thiomorpholinyl, 13-oxa-11-aza-tricyclo[7.3.1.0-2,7]tridecy-2,4,6-triene, tetrahydropyranyl, 2-oxo-2H-pyranyl, tetrahydrofuranyl, 1,3-dioxolanone, 1,3-dioxanone, 1,4-dioxanyl, 8-oxa-3-aza-bicyclo[3.2.1]octanyl, 2-oxa-5-aza-bicyclo[2.2.1]heptanyl, 2-thia-5-aza-bicyclo[2.2.1]heptanyl, piperidinonyl, tetrahydro-pyrimidonyl, pentamethylene sulphide, pentamethylene sulfoxide, pentamethylene sulfone, tetramethylene sulphide, tetramethylene sulfoxide and tetramethylene sulfone, indazolyl, benzimidazolyl, benzodioxolyl, imidazolyl, 1,3-benzodioxolyl and pyrazolyl.

The expressions "alkyl/alkenyl/alkynyl ether" refer to a saturated or non-saturated, straight-chain or branched hydrocarbon group that contains the number of carbon items indicated. For example, "($C_{1-20}$)alkyl ether" denotes a hydrocarbon residue containing from 1 to 20 carbon atoms, and any suitable number of oxygen atoms that will result in an ether structure. Alkyl/alkenyl/alkynyl ether groups as used herein, shall be understood to mean any linear or branched, substituted or non-substituted alkyl/alkenyl/alkynyl chain comprising an oxygen atom either as an ether motif, i.e. an oxygen bound by two carbons. Exemplary alkyl ethers are polyethylene glycol (PEG) chains. The term polyethylene glycol as used herein refers to a chain of substituted or non-substituted ethylene oxide monomers. For example, a PEG chain may comprise 1 to 10 ethylene oxide monomers. The ether residue can be attached to the Formulas provided in the present invention either via the carbon atom or via the oxygen atom of the ether residue.

The "substituent" or "residue" or "R" as used herein, optionally $R^3$, $R^4$, $R^5$, $R^6$, $R^7$, $R^8$, $R^9$, $R^{9'}$, $R^{9''}$, and/or $R^{10}$ can be attached directly to the Formulas provided in the present invention or optionally by means of a linker. Said linker can also be in the form of PEG.

If more than one residue R is attached to a given atom of a formula described herein, one residue R can be absent if the attachment of the other R leads to a full valency of the atom. For Example, $R^7$ can be —$N_2$. This leads to an azide formed with the nitrogen to which $R^7$ is attached. In this case, only one $R^7$ is attached to the nitrogen and the other $R^7$ is absent as shown below.

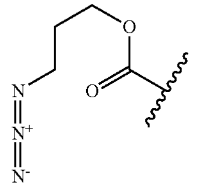 [SMILES: *C(=O)OCCCN=[N+]=[N-]]

As used herein, the terms "nitrogen" or "N" and "sulphur" or "S" include any oxidized form of nitrogen and sulphur and the quaternized form of any basic nitrogen as long as the resulting compound is chemically stable. For example, for an —S—$C_{1-6}$ alkyl radical shall be understood to include —S(O)—$C_{1-6}$alkyl and —$S(O)_2$—$C_{1-6}$ alkyl.

As used herein, a wording defining the limits of a range of length such as, e. g., "from 1 to 5" or "($C_{1-5}$)" means any integer from 1 to 5, i. e. 1, 2, 3, 4 and 5. In other words, any range defined by two integers explicitly mentioned is meant to comprise and disclose any integer defining said limits and any integer comprised in said range.

The scope of the present invention includes those analogs of the compounds as described above and in the claims that feature the exchange of one or more carbon-bonded hydrogens, optionally one or more aromatic carbon-bonded hydrogens, with halogen atoms such as F, Cl, or Br, optionally F. The exchange of one or more of the carbon-bonded hydrogens, e.g. by fluorine, can be done, e.g., for reasons of metabolic stability and/or pharmacokinetic and physico-chemical properties.

In another aspect, the present invention is directed to a composition, optionally a pharmaceutical composition, comprising as active substance a compound for use as described herein or a pharmaceutically acceptable derivative thereof, optionally combined with excipients and/or carriers.

The invention includes pharmaceutically acceptable salts or solvates of the compounds of Formula (I) and (II) of the present invention. A "pharmaceutically acceptable salt or solvate" refers to any pharmaceutically acceptable salt, solvate or ester or any other compound which, upon administration to a patient, is capable of providing (directly or indirectly) a compound of the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the present invention.

Pharmaceutically acceptable salts include those derived from pharmaceutically acceptable inorganic and organic acids and bases. Examples of suitable acids include hydrochloric, hydrobromic, sulphuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g. magnesium), ammonium and N—$(C_1$-$C_4$alkyl$)_4$ salts.

The terms "compound (according to the present invention)" and "probe" are used interchangeably herein.

The terms "polypeptide" and "peptide" are used interchangeably and, as used herein, are meant to comprise peptides, polypeptides, oligopeptides and proteins that comprise two or more amino acids linked covalently through peptide bonds. The term does not refer to a specific length of the product. Polypeptides include post-translational modifications of the polypeptides, for example, glycosylations, acetylations, phosphorylations, disulfide bridges, cleavages and the like. The terms peptide and polypeptide also encompass polypeptide analogs, (poly)peptides comprising non-natural amino acids, peptidomimetics, ß-amino acids, etc.

The terms "peptide" and "polypeptide", as used herein, also encompasses an isolated and purified glycosylated or non-glycosylated polypeptide.

Exemplary peptides for $R^9$ of all aspects and embodiments include, e.g., $[ChaR]_3$ (see Example 18), -[ProHypGly$]_3$-AopProGly-[ProHypGly$]_3$, -[ProHypGly$]_7$ or -[ProProGly$]_7$ (see Examples 11 to 13) with or without a linker as defined herein.

In another aspect, the present invention is directed to a compound as described herein or a pharmaceutically acceptable salt thereof, for use in the diagnosis of an amine oxidase-associated disease and/or a collagen- or elastin-associated disease.

The term "amine oxidase" as used herein, for all aspects is meant to describe any enzyme, i.e. a polypeptide, having catalytic activity in at least catalyzing the oxidative cleavage of alkylamines into aldehydes and ammonia, optionally the oxidative deamination of the ε-amine of a lysine to an aldehyde. Tests and assays for determining whether a given enzyme is an amine oxidase as defined herein are well known in the art (see, e.g., A. H. Palamakumbura, P. C. Trackman, Analytical Biochemistry 2002, 300, 245-251). Alternatively or additionally, the test of Example 2 below can be used to determine whether a given enzyme is an amine oxidase as defined herein. Optionally, a change in at least 5%, 10%, 15%, 20%, 25%, 30%, 35%, 40%, 45%, 50%, 55%, 60%, 65%, 70%, 75% or 80% in fluorescence emission at the emission maximum of the fluorescent cleavage probe is indicative of amine oxidase activity as used herein. Optionally and with reference to the Figures and Examples (and the corresponding conditions) provided herein, a change in at least 1000, 1500, 2000, 2500, 3000, 3500, 4000, 4500, 5000, 5500, 6000, 6500, 7000, 7500, 8000, 8500, 9000, 9500, 10000, 10500, 11000, 12000, 13000, 14000, 15000, 16000, 17000, 18000, 19000 or 20000 RFU in fluorescence emission at the emission maximum of the fluorescent cleavage probe is indicative of amine oxidase activity as used herein. Optionally, any enzyme that cleaves 95, 90, 85, 80, 75, 70, 65, 60, 55, 50, 45, 40, 35, 30, 25 or 20% of the provided alkylamines into aldehydes and ammonia under the known conditions or the conditions set forth in Example 2, is an amine oxidase as used herein.

Optionally, the amine oxidase described herein is an animal or human amine oxidase, optionally a mammalian amine oxidase, optionally a human amine oxidase.

The term "catalyze" as used herein means that the amine oxidase described herein increases the rate of the reaction towards the desired product, i.e. towards the oxidative cleavage of alkylamines into aldehydes and ammonia, optionally towards the deamination of an ε-amine of lysine to an aldehyde, to a greater extent compared to the rate of the reaction in the absence of the amine oxidase.

An "amine oxidase associated disease" described herein is any disease that is directly or indirectly caused or exacerbated by an amine oxidase. The disease may be caused or exacerbated by, e.g., a defect in the expression of the amine oxidase, amine oxidase under-expression, amine oxidase over-expression, amine oxidase degradation or accumulation, increased or decreased amine oxidase activity or any other influence on an amine oxidase that leads to a non-healthy, e.g. non-standard or pathological amine oxidase function. The amine oxidase associated disease may be a disease which results from, leads to, is based on or is connected with a collagen- or elastin-associated disease.

The term "collagen- or elastin-associated disease" as used herein for all aspects is a disease that results from or leads to defects in the collagen or elastin structures, e.g. the extracellular matrix. Optionally, the collagen- or elastin-associated diseases described herein are based on or reflected in defects in the cross-linking of collagen or elastin, e.g. due to increases or decreases in amine oxidase activity.

In another aspect, the present invention is directed to a use of a compound as described herein in the in vitro or ex vivo diagnosis of an amine oxidase-associated disease and/or a collagen- or elastin-associated disease.

The diagnosis of an amine oxidase-, collagen- or elastin-associated disease is based on the detection of the catalytic activity of an amine oxidase by the compounds described herein. The compounds' fluorescent signal may be used to detect, localize and/or quantify amine oxidase activity. Based on the detection, localization or quantification of the amine oxidase activity, an amine oxidase-, collagen- or elastin-associated disease can be diagnosed or detected and progression of such a disease can be monitored.

The diagnosis of any aspect described herein or the diagnostic use and method described herein can be performed in vitro, in or ex vivo. In vivo application may include, e.g. a mouthwash comprising a compound according to the present invention, wherein the mouthwash is suitable for diagnosing amine oxidase activity in the oral cavity of a subject by irradiating the cavity with light and assessing the fluorescence emitted by the compound. Another diagnostic method may include treating the tissue topically or contacting a site of tissue removal in a patient, e.g. during surgery, with a compound according to the present invention in order to determine whether tissue with, e.g. elevated, amine oxidase activity is still present in the patient. In general, fluorescence can be detected by any method known in the art, including by fluorescence microscopy or the naked eye to qualitatively determine the presence or absence of, e.g. elevated, amine oxidase activity.

Optionally, the compound or pharmaceutical composition as described herein is for use in the diagnosis of animals or humans, optionally mammalians, optionally humans.

The term "a sample of a patient" as used in the present context is meant to include any tissue, e.g. biopsy, body liquid, e.g. blood, serum, cerebral or cerebrospinal fluid.

For diagnostic use, the compounds described herein may be administered in any conventional dosage form in any conventional manner. Routes of administration include, but are not limited to oral administration, e.g. a mouth wash, topical administration, e.g. a liquid, cream, gel, spray or dispersion, dermal administration, inhaled administration, intravenous, intramuscular and subcutaneous injections. Exemplary modes of administration are topical, intravenous, intradermal or subcutaneous.

The compounds may be administered alone or in combination in certain embodiments with adjuvants that enhance stability of the compounds, facilitate administration of pharmaceutical compositions containing them, retard or enhance the release of the compounds, provide increased dissolution or dispersion, increase activity, and the like, including other active ingredients.

The herein-described compounds may be physically combined with conventional thera-peutics, diagnostics or other adjuvants into a single pharmaceutical composition. Reference in this regard may be made to Cappola et al.: U.S. patent application Ser. No. 09/902,822, PCT/US 01/21860 und U.S. provisional application No. 60/313,527, each incorporated by reference herein in their entirety. Advantageously, the compounds may then be administered together in a single dosage form. In some embodiments, the pharmaceutical compositions comprising such combinations of compounds contain at least about 5%, optionally at least about 20%, of a compound of the present invention (w/w). The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds described herein in all aspects include pharmaceutically acceptable carriers and adjuvants known to those of ordinary skill in the art. Methods for preparing such dosage forms are known (see, for example, H. C. Ansel and N. G. Popovish, Pharmaceutical Dosage Forms and Drug Delivery Systems, $5^{th}$ ed., Lea and Febiger (1990)). Dosage levels and requirements are well-recognized in the art and may be selected by those of ordinary skill in the art from available methods and techniques suitable for a particular patient. In some embodiments, dosage levels range from 1-500 mg/dose for a 70 kg patient. Although one dose per day may be sufficient, up to 5 doses per day may be given. For oral doses, up to 2500 mg/day may be required. For topical doses, a concentration of e.g. 10-10000 μM per $cm^2$ can be used. Reference in this regard may also be made to U.S. provisional application No. 60/339,249. As the skilled artisan will appreciate, lower or higher doses may be required depending on particular factors. For instance, specific doses and diagnostic regimens will depend on factors such as the patient's general health profile, the severity and course of the patient's disorder or disposition thereto, and the judgment of the treating physician.

In an embodiment, the compound for use or the use as described herein is one, wherein the amine oxidase associated disease is a disease associated with an amine oxidase selected from the group consisting of (i) a lysyl oxidase (LOX), optionally a lysyl oxidase having at least 80%, optionally at least 85%, 90% or 95% sequence identity, optionally over the whole sequence, with at least one of SEQ ID NOs: 1 to 3;
(ii) lysyl oxidase homolog 1, 2, 3 or 4 (LOXL 1, 2, 3 or 4),
(iii) a primary-amine oxidase, optionally AOC2 or AOC3,
(iv) a diamine oxidase, optionally AOCl,
(v) a monoamine oxidase, optionally MAOA or MAOB, optionally a monoamine oxidase having at least 80%, optionally at least 85%, 90% or 95% sequence identity, optionally over the whole sequence, with at least one of SEQ ID NOs: 4 to 7.

The percentage identity of amino acid sequences as described herein can be determined with the assistance of known methods. In general, special computer programs are employed that use algorithms adapted to accommodate the specific needs of this task. Exemplary methods for determining amino acid identity begin with the generation of the largest degree of identity among the sequences to be compared. Exemplary computer programs for determining the identity among two amino acid sequences comprise, but are not limited to, TBLASTN, BLASTP, BLASTX, TBLASTX (Altschul et al., J. Mol. Biol., 215, 403-410, 1990), or ClustalW (Larkin M A et al., Bioinformatics, 23, 2947-2948, 2007). The BLAST programs can be obtained from the National Center for Biotechnology Information (NCBI) and from other sources (BLAST handbook, Altschul et al., NCB NLM NIH Bethesda, MD 20894). The ClustalW program can be obtained from http://www.clustal.org.

The amine oxidases described herein which may be monitored by means of the compounds of the invention encompass any functional derivative or functional fragment thereof. The term "functional derivative" of an enzyme or peptide described in the context of the present invention is meant to include any enzyme or peptide or fragment thereof that has been chemically, post-translationally or genetically modified in its amino acid sequence, e.g. by addition, substitution and/or deletion of amino acid residue(s) and/or has been chemically modified in at least one of its atoms and/or functional chemical groups, e.g. by glycosylation(s), additions, deletions, rearrangement, oxidation, reduction, disulphide bridging etc. as long as the derivative still has at least some amine oxidase activity to a measurable extent, e.g. of at least about 1 to 10%, optionally at least about 20 to 50% amine oxidase activity of the unmodified peptide, e.g. an amine oxidase, a LOX, LOXL, primary amine oxidase, diamine oxidase, monoamine oxidase or an amine oxidase comprising any one of SEQ ID NOs: 1 to 7.

In this context a "functional fragment" as used herein is one that forms part of a peptide or derivative mentioned in the context of the invention and still has at least some amine oxidase activity to a measurable extent, e.g. of at least about 1 to 10%, optionally at least about 20 to 50% amine oxidase activity of the unmodified peptide. For example, lysyl oxidase according to SEQ ID NO: 1 is cleaved in cells into a signal peptide (amino acids 1 to 21), a propeptide (amino acids 22 to 168), a lysyl oxidase long form (amino acids 169 to 417; SEQ ID NO: 2) and a lysyl oxidase short form (amino acids 219 to 417; SEQ ID NO: 3). Both, the long and short form are functional fragments of the lysyl oxidase according to SEQ ID NO:1.

Inappropriate expression of amine oxidases has been observed in a number of human diseases (many involving a fibrotic response), in particular cancer (Barker et al. 2012, Nature Reviews Cancer, 12, 540-552).

In an embodiment, the compound for use or the use as described herein is one, wherein the disease is selected from the group consisting of fibrosis, optionally pulmonary and hepatic fibrosis, cardiomyopathy, occipital horn syndrome (OHS), Menkes' syndrome, myocardial ischaemia, atherosclerosis, scleroderma, keloid disorder, liver cirrhosis, Alzheimer's and non-Alzheimer's dementia, Wilson's disease, primary biliary cirrhosis, chronic venous insufficiency, pseudoexfoliation syndrome, glaucoma, pelvic organ prolapse, endometriosis, intracranial aneurysms, heart failure and cancer including tumor metastasis.

In an embodiment, the compound for use or the use as described herein is one, wherein the cancer is selected from the group consisting of colorectal cancer, bladder cancer, pancreatic cancer, breast cancer, head and neck squamous-cell carcinoma (HNSCC), laryngeal cancer, lung cancer, gastric cancer, prostate cancer, esophageal squamous cell cancer, endometrial cancer, testicular seminoma cancer, hepatocellular cancer, renal clear cell cancer, and basal and squamous skin cell carcinoma.

In another aspect, the present invention is directed to a use of a compound as described herein for the detection of amine oxidase activity, optionally of activity of an amine oxidase selected from the group consisting of (i) a lysyl oxidase (LOX), optionally a lysyl oxidase having at least 80%, optionally at least 85%, 90% or 95% sequence identity, optionally over the whole sequence, with at least one of SEQ ID NOs: 1 to 3;
(ii) lysyl oxidase homolog 1, 2, 3 or 4 (LOXL 1, 2, 3 or 4),
(iii) a primary-amine oxidase, optionally AOC2 or AOC3,
(iv) a diamine oxidase, optionally AOC1,
(v) a monoamine oxidase, optionally MAOA or MAOB, optionally a monoamine oxidase having at least 80%, optionally at least 85%, 90% or 95% sequence identity, optionally over the whole sequence, with at least one of SEQ ID NOs: 4 to 7.

In another aspect, the present invention is directed to a method, optionally an in vivo, in vitro or ex vivo method, for the detection of amine oxidase activity comprising the following steps:

(a) providing a compound as described herein;
(b) providing and contacting a cell, tissue or body fluid with the compound of step (a), optionally in vivo, in vitro or ex vivo, under conditions which allow for amine oxidase activity;
(c) measuring fluorescence in the cell, tissue or body fluid, optionally by fluorescence microscopy, and
(d) determining the activity and/or location of the amine oxidase based on the fluorescence measured in step (c).

In another aspect, the present invention is directed to a method for the diagnosis of an amine oxidase-associated disease and/or a collagen- or elastin-associated disease in a patient, optionally a mammal, or sample of a patient in need thereof, comprising the following steps:

(a) providing a compound as described herein;
(b) contacting the patient or the sample of the patient in need thereof with an effective amount of the compound of step (a), wherein the effective amount is effective for detecting an amine oxidase activity;
(c) measuring fluorescence in the patient or sample of the patient; and
(d) determining activity and/or location of the amine oxidase based on the fluorescence measured in step (c).

In an embodiment, the method as described herein is one, wherein the amine oxidase is selected from the group consisting of (i) a lysyl oxidase (LOX), optionally a lysyl oxidase having at least 80%, optionally at least 85%, 90% or 95% sequence identity, optionally over the whole sequence, with at least one of SEQ ID NOs: 1 to 3;
(ii) lysyl oxidase homolog 1, 2, 3 or 4 (LOXL 1, 2, 3 or 4),
(iii) a primary-amine oxidase, optionally AOC2 or AOC3,
(iv) a diamine oxidase, optionally AOC1,
(v) a monoamine oxidase, optionally MAOA or MAOB, optionally a monoamine oxidase having at least 80%, optionally at least 85%, 90% or 95% sequence identity, optionally over the whole sequence, with at least one of SEQ ID NOs: 4 to 7.

In an embodiment, the method as described herein is one, wherein the disease is selected from the group consisting of fibrosis, optionally pulmonary and hepatic fibrosis, cardiomyopathy, occipital horn syndrome (OHS), Menkes' syndrome, myocardial ischaemia, atherosclerosis, scleroderma, keloid disorder, liver cirrhosis, Alzheimer's and non-Alzheimer's dementia, Wilson's disease, primary biliary cirrhosis, chronic venous insufficiency, pseudoexfoliation syndrome, glaucoma, pelvic organ prolapse, endometriosis, intracranial aneurysms, heart failure and cancer including tumor metastasis, optionally a cancer selected from the group consisting of colorectal cancer, bladder cancer, pancreatic cancer, breast cancer, head and neck squamous-cell carcinoma (HNSCC), laryngeal cancer, lung cancer, gastric cancer, prostate cancer, esophageal squamous cell cancer, endometrial cancer, testicular seminoma cancer, hepatocellular cancer, renal clear cell cancer, and basal and squamous skin cell carcinoma.

In another aspect, the present invention is directed to a use of a compound as described herein in the method as described herein.

BRIEF DESCRIPTION OF THE DRAWINGS

The following Figures and Examples serve to illustrate the invention and are not intended to limit the scope of the invention as described in the appended claims. The term "Pacific Blue" or "PB", as used herein, corresponds to 3-acetoxy-6,8-difluoro-7-hydroxycumarin.

FIG. 10 (*b*) shows the fluorescent signals obtained from Compound 5 treated with homogenate of isolated mouse skin at 1 mg/mL total protein concentration. Signals of Compound 5 at 20 μM during a 1 h incubation at 37° C. with tissue homogenate are shown as relative fluorescence units (RFU) when excited at 405 nm and measured at 460 nm (Ex/Em respectively). Background controls for untreated homogenate and untreated Compound 5 at 20 μM are measured concurrently with all treated samples. Error bars represent SD, $n\geq3$.

Figure 13:
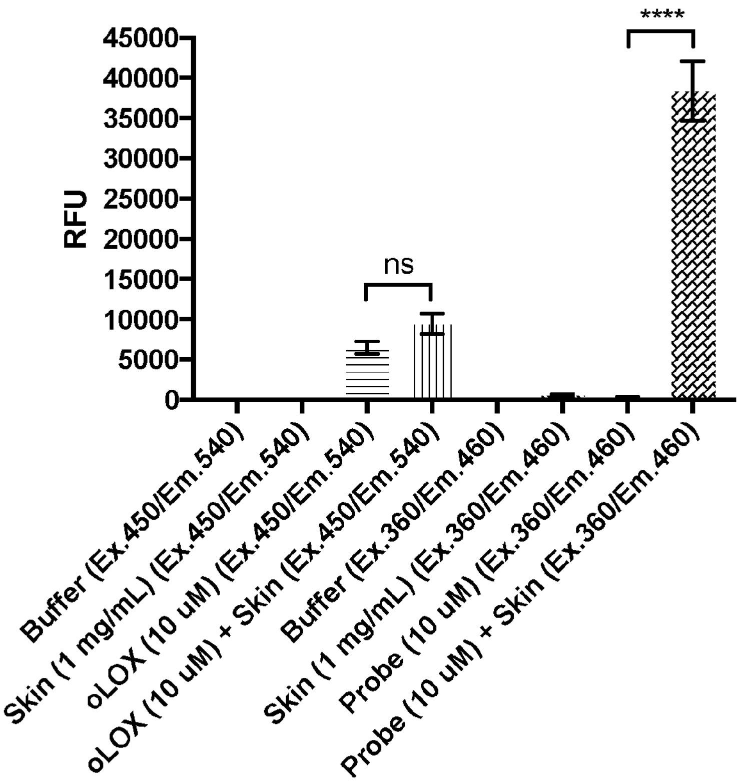
Figure 13:
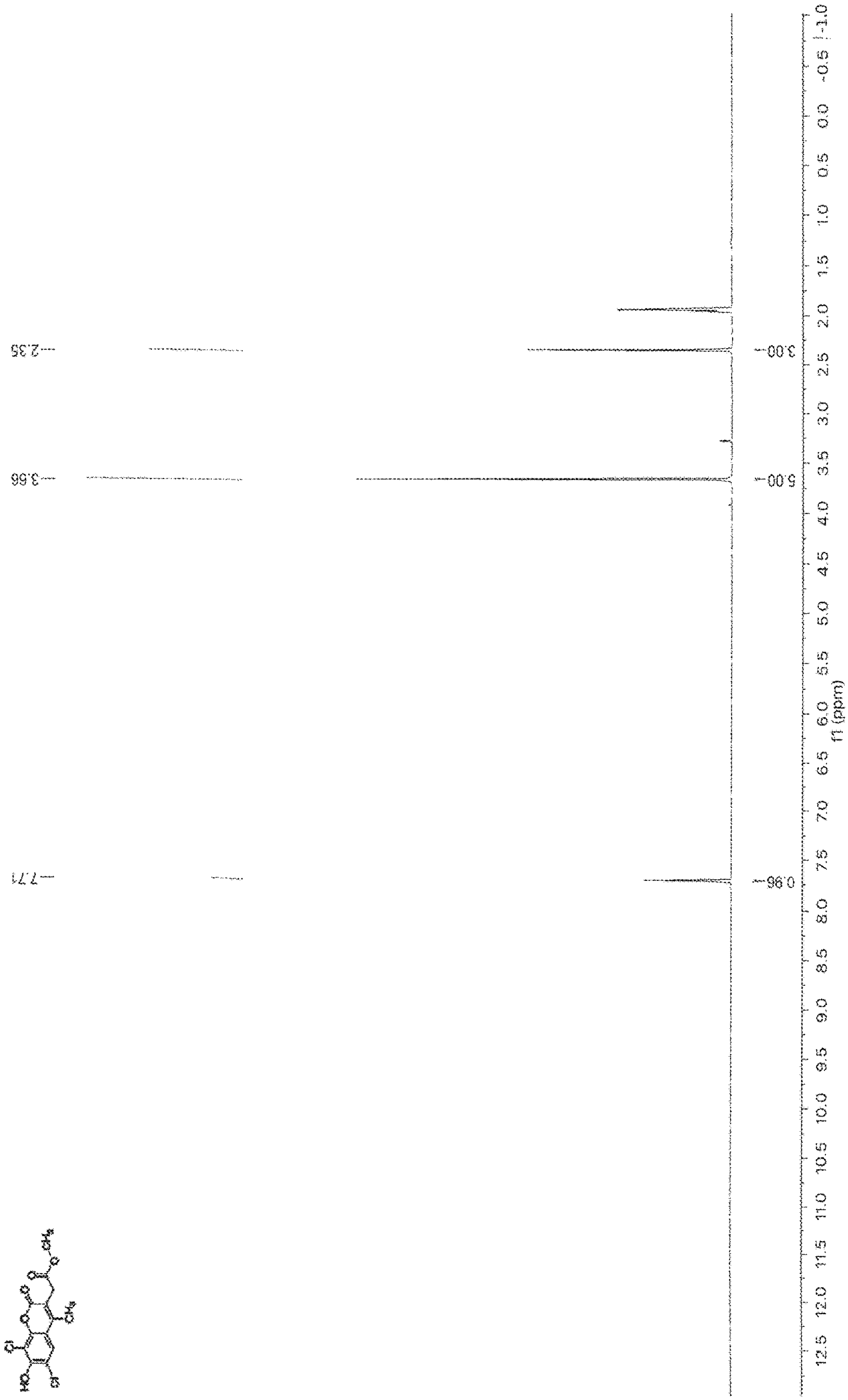

FIG. 13 (*a*) shows the fluorescent signal obtained from Compound 2 treated with mouse tissue homogenate of isolated skin in comparison to 3',6'-Bis(3-aminopropoxy)-3H-spiro[2-benzofuran-1,9'-xanthen]-3-one dihydrochloride (oLOX probe). Fluorescent signals generated by 10 μM Compound 2 and 10 μM oLOX after a 24 h incubation at 37° C. with tissue homogenate are shown as relative fluorescence units (RFU). Samples were excited and measured at the absorbance maximum and emission maximum for each system (oLOX Ex. 450 nm/Em. 540 nm, and Compound 2 Ex. 360 nm/Em. 460 nm). All controls are measured simultaneously with their respective treated samples under otherwise identical instrument settings. A significant increase in fluorescent signal was obtained for the probe Compound 2 when incubated with the homogenate (**, $p<0.0001$, one-way ANOVA), but not for oLOX (ns, $p=0.2696$, one-way ANOVA). Error bars represent SD, $n \geq 3$. FIG. 13** (*b*) shows the $^1H$ NMR spectrum of 3-carboxymethyl-6,8-dichloro-7-hydroxycoumarin in $CD_3CN$ (400 MHz).

Figure 14:
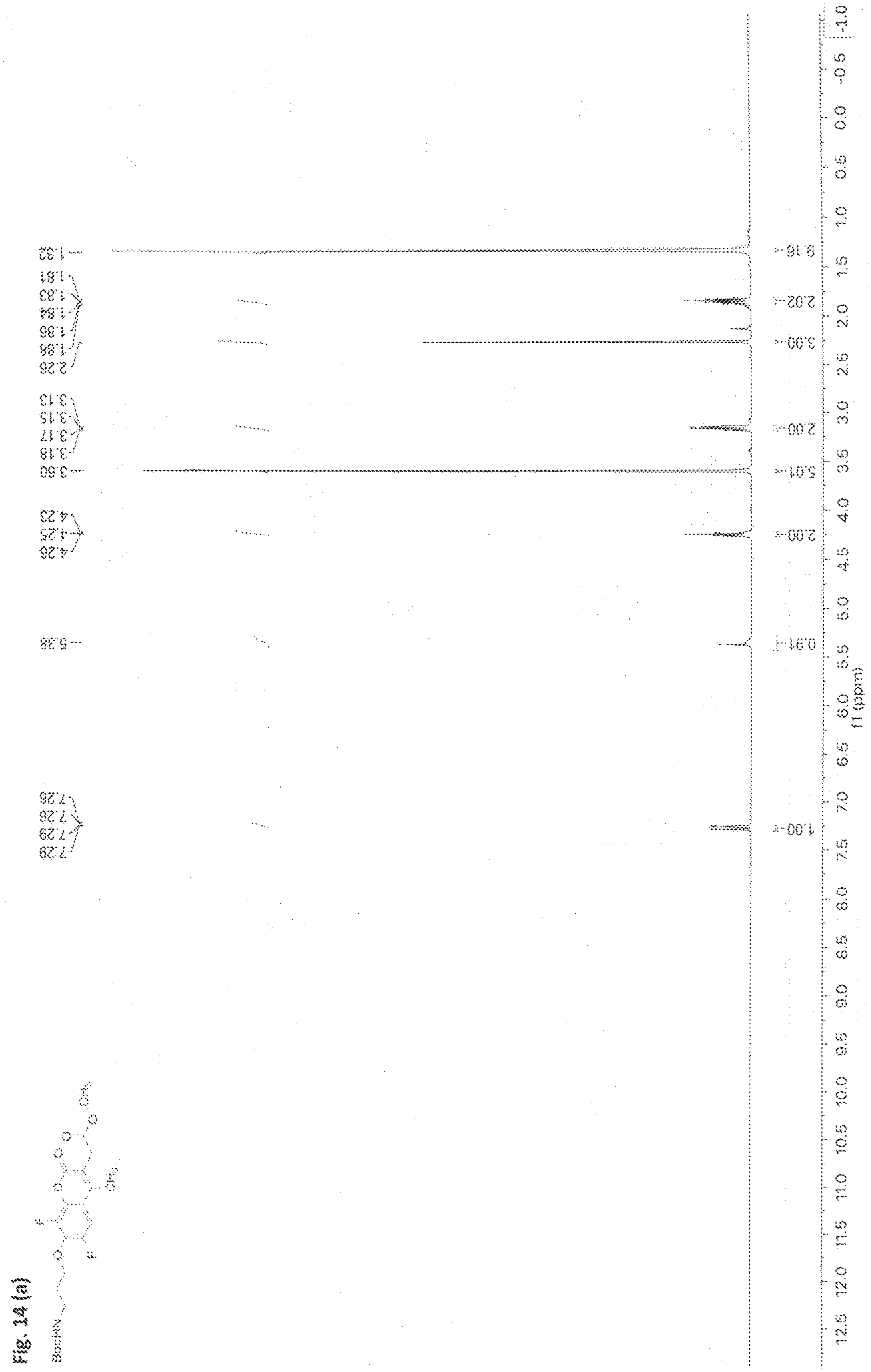
Figure 14:
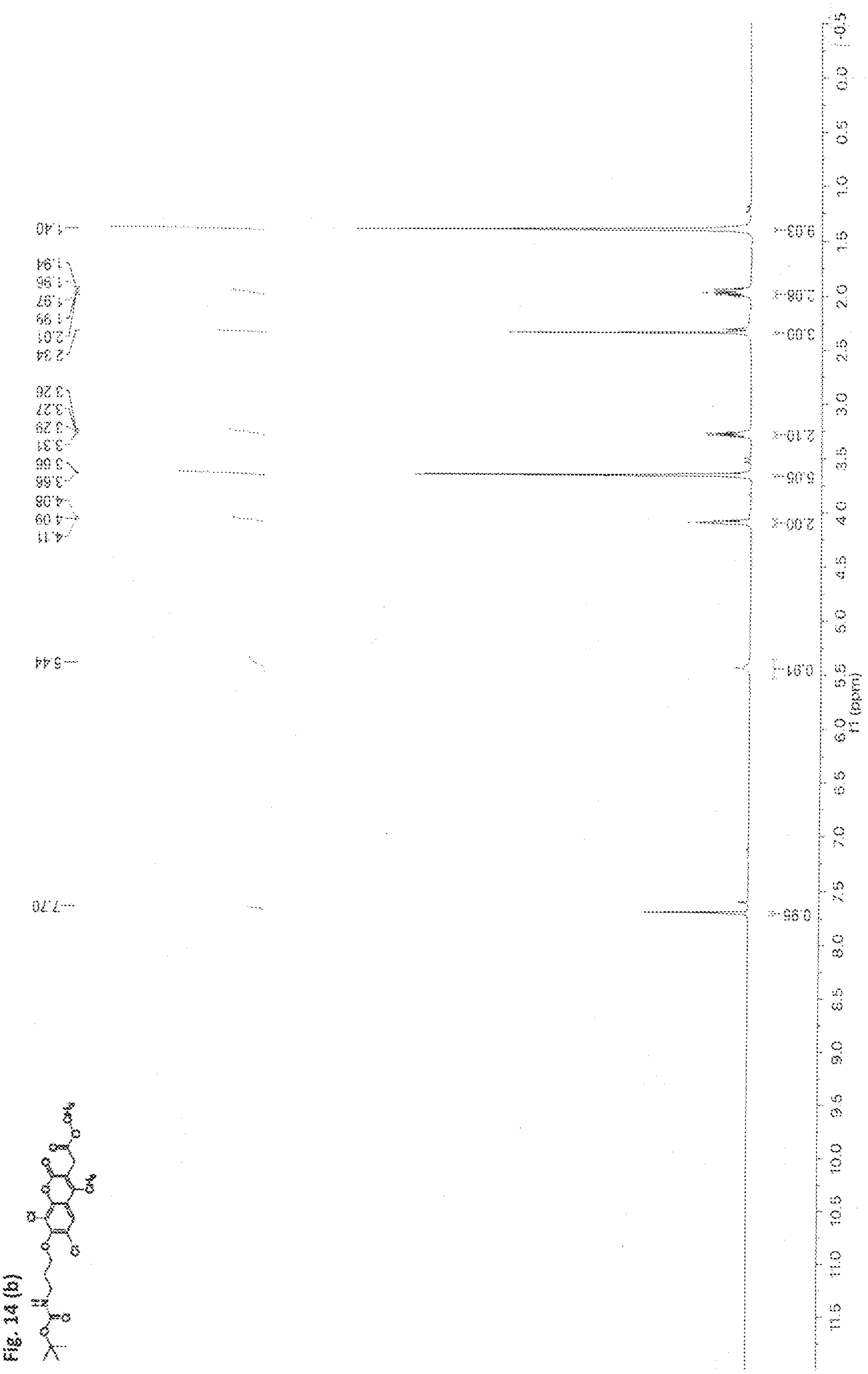

FIG. 14 (*a*) shows the $^1H$ NMR spectrum of 3-methylacetate-6,8-difluoro-7-(4-((tert-butoxycarbonyl)amino)propoxy)-coumarin in $CD_3CN$ (400 MHz). FIG. 14 (*b*) shows the $^1H$ NMR spectrum of 3-methylacetate-6,8-dichloro-7-(4-((tert-butoxycarbonyl)amino)propoxy)-coumarin in $CD_3CN$ (400 MHz).

Figure 15:
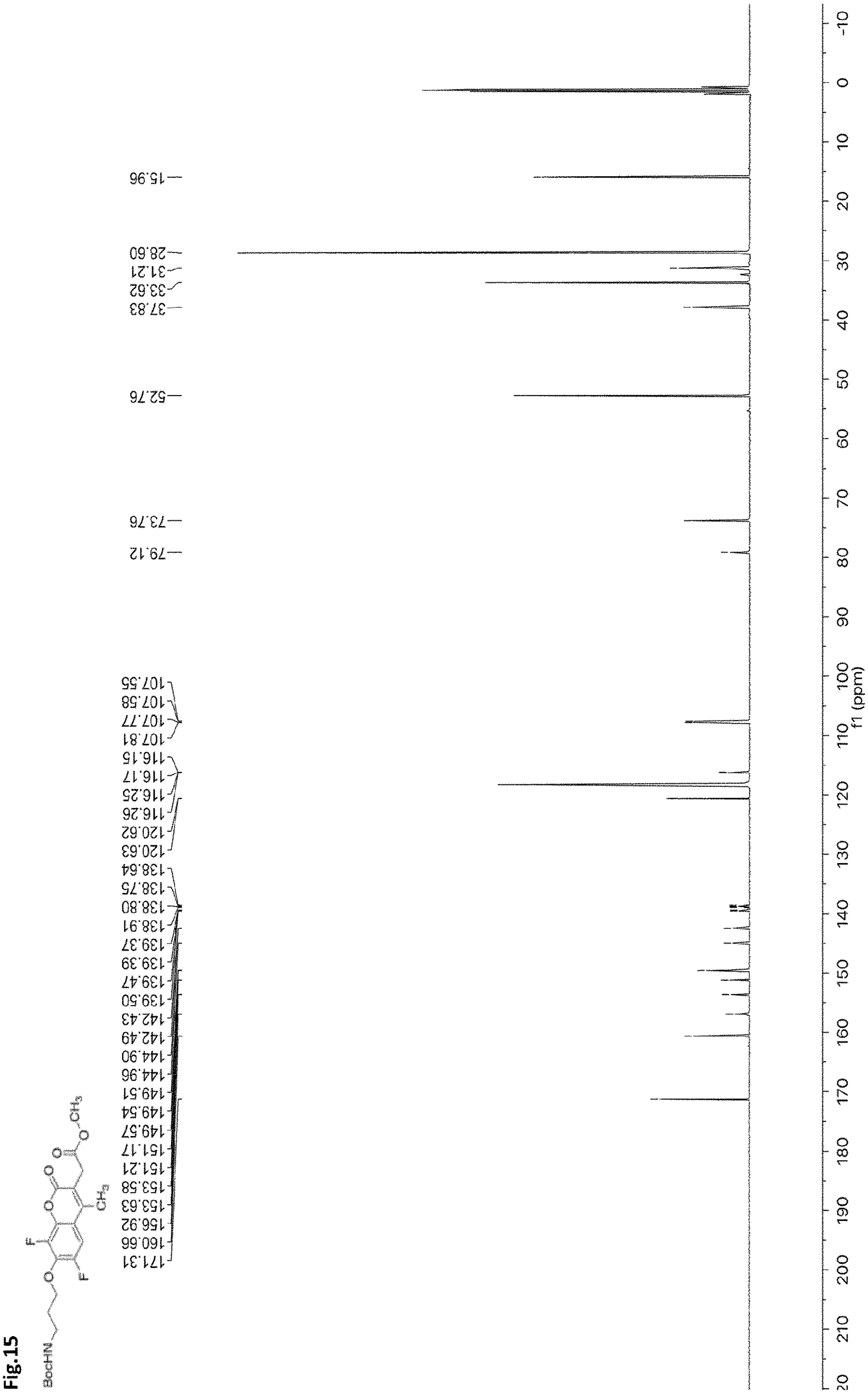

FIG. 15 shows the $^{13}C$ NMR spectrum of 3-methylacetate-6,8-difluoro-7-(4-((tert-butoxycarbonyl)amino)propoxy)-coumarin in $CD_3CN$ (101 MHz).

Figure 16:
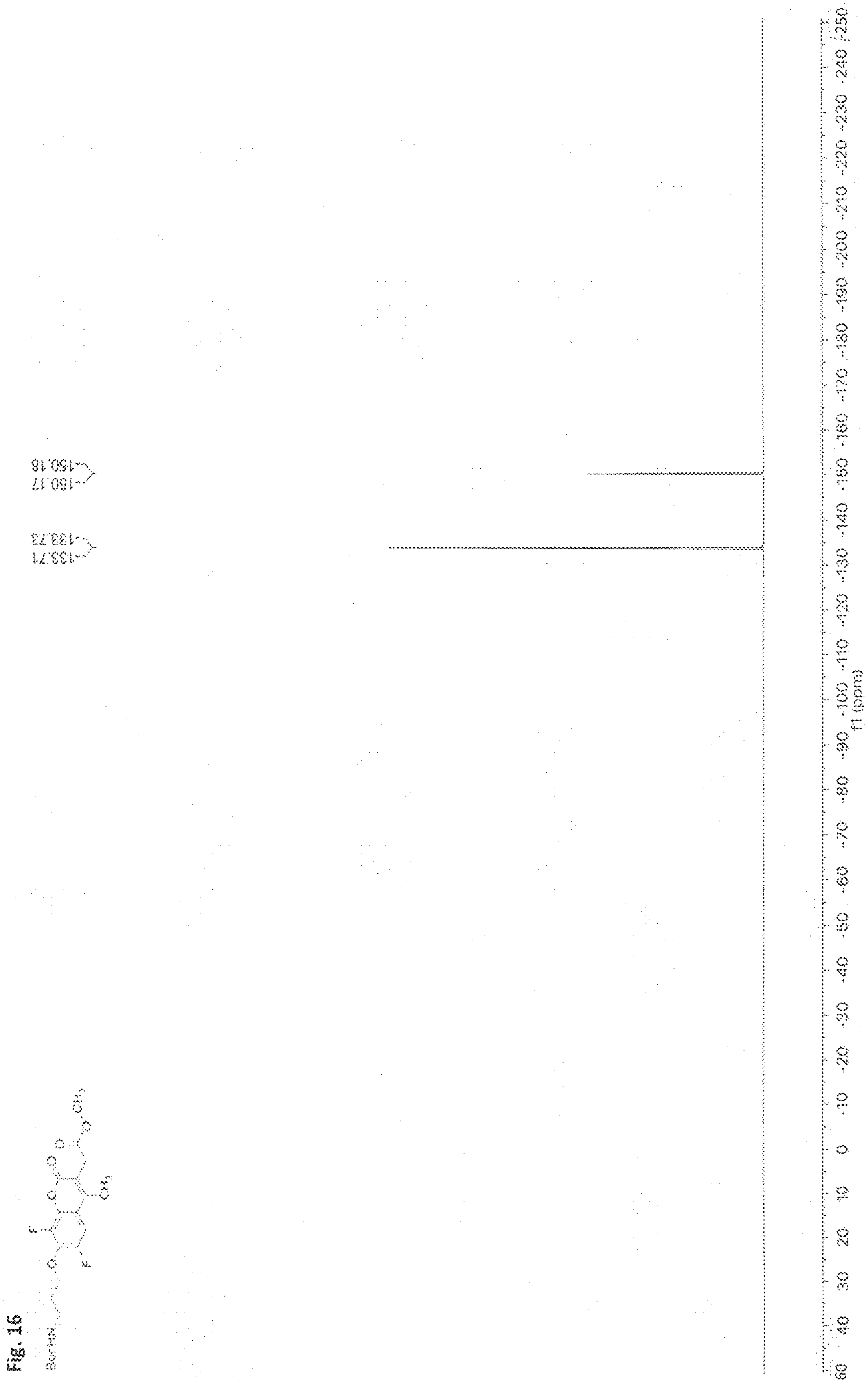

FIG. 16 shows the $^{19}F$ NMR H-F decoupled spectrum of 3-methylacetate-6,8-difluoro-7-(4-((tert-butoxycarbonyl)amino)propoxy)-coumarin in $CD_3CN$ (376 MHz).

Figure 17:
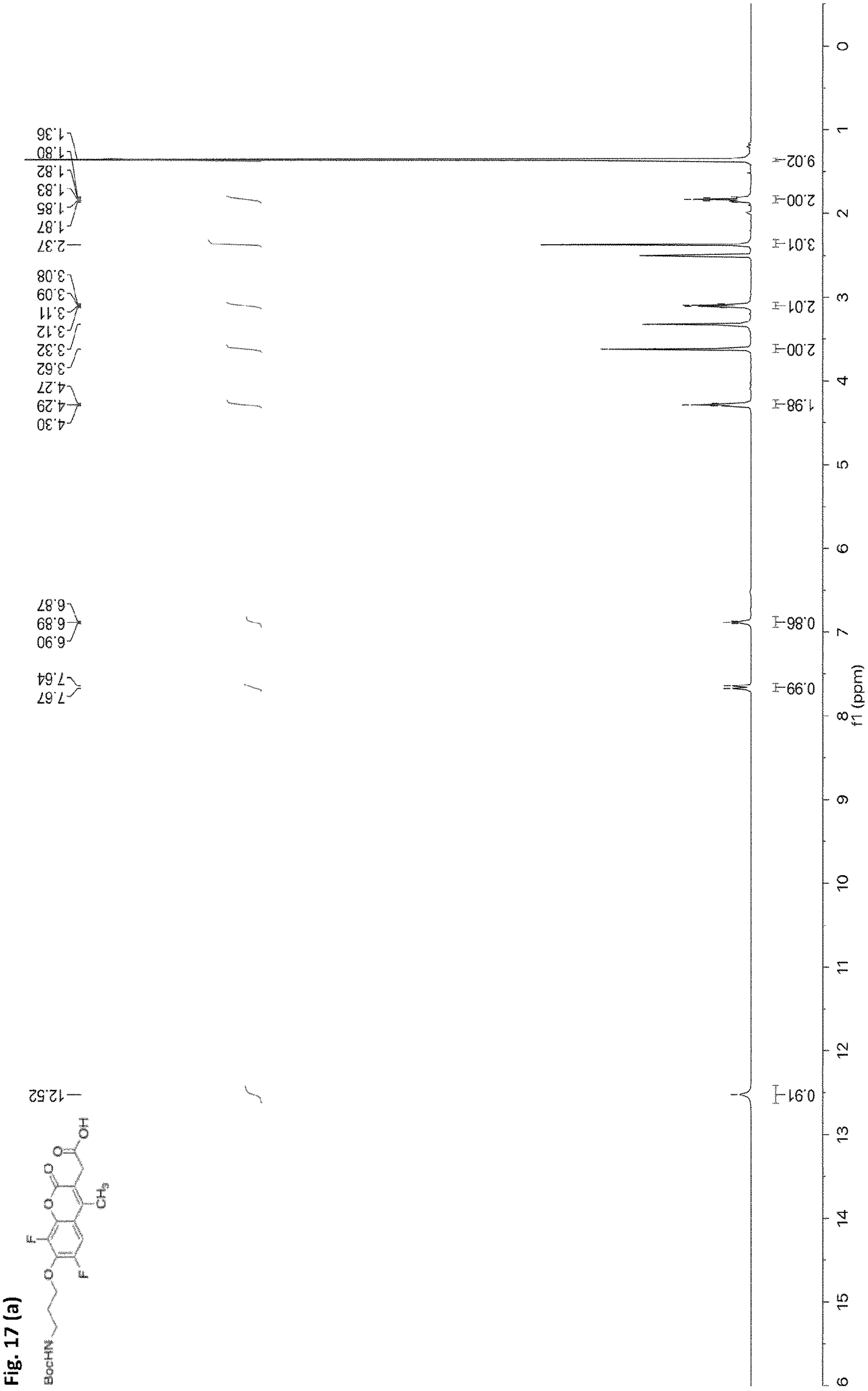
Figure 17B:
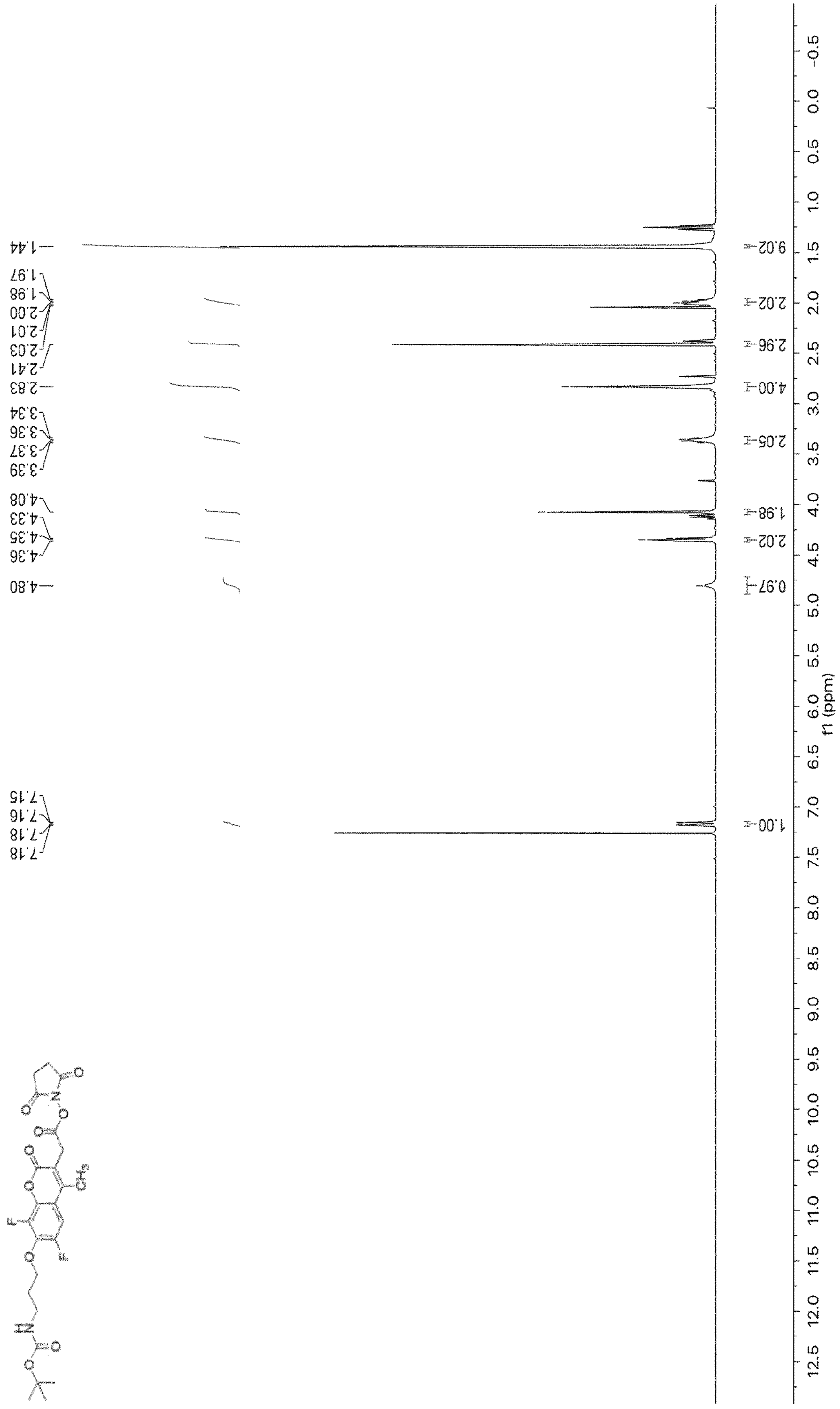

FIG. 17 (*a*) shows the $^1H$ NMR spectrum of Compound 1 in DMSO-$d_6$ (400 MHz). FIG. 17 (*b*) shows the $^1H$ NMR spectrum of MRA_3102 in $CDCl_3$ (400 MHz).

Figure 18:
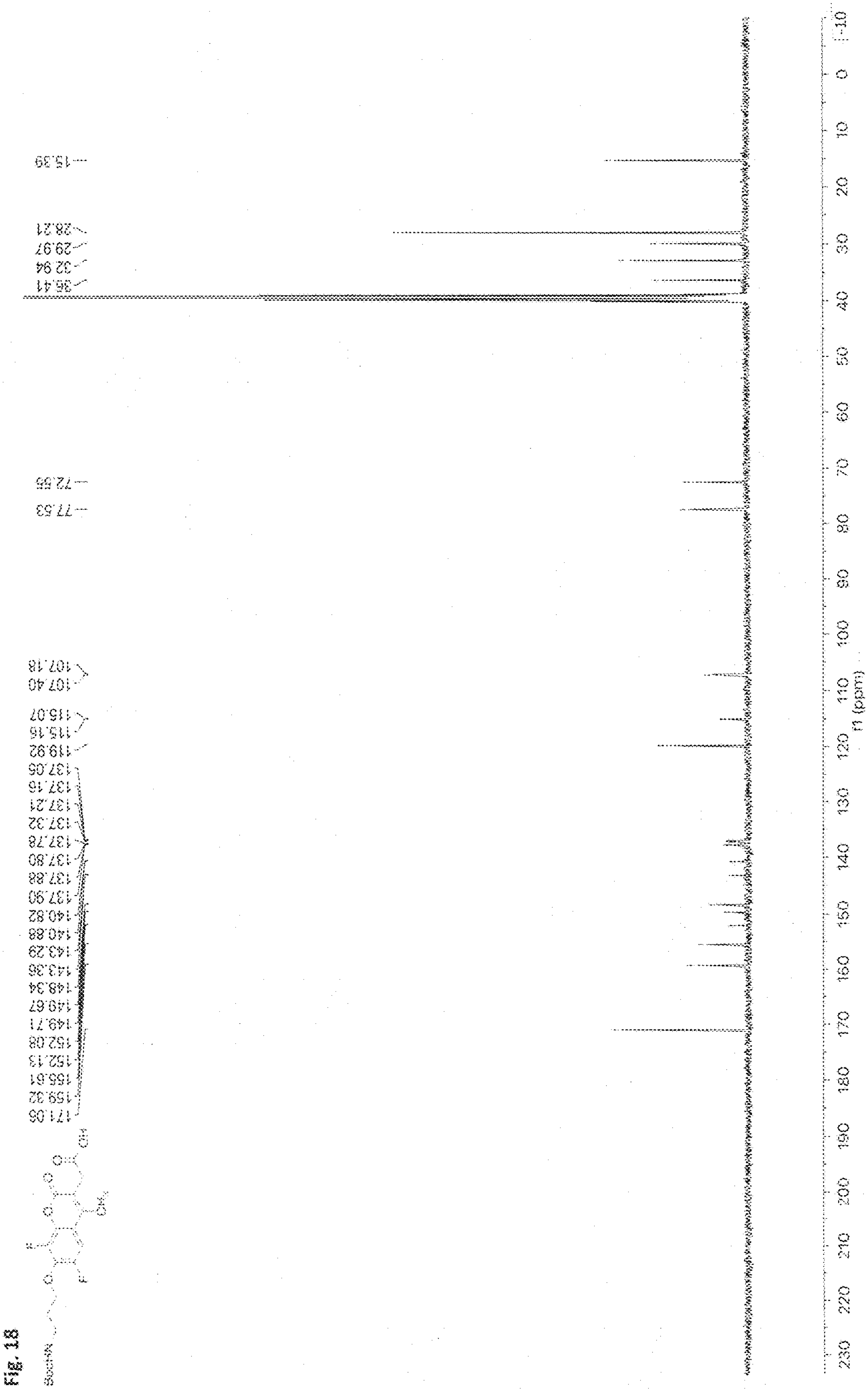

FIG. 18 shows the $^{13}C$ NMR spectrum of Compound 1 in DMSO-$d_6$ (101 MHz).

Figure 19:
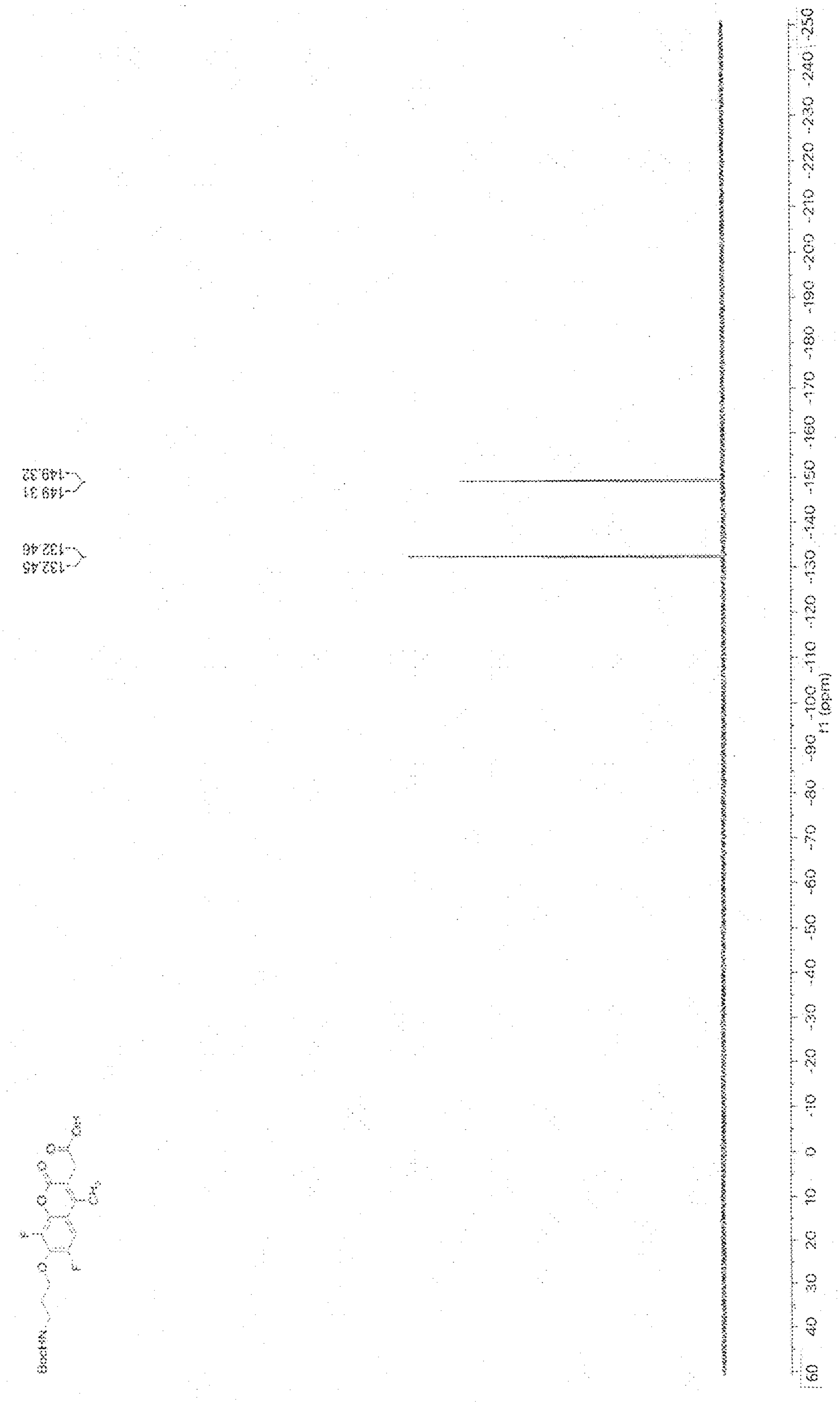

FIG. 19 shows the $^{19}F$ NMR F-H decoupled spectrum of Compound 1 in DMSO-$d_6$ (376 MHz).

Figure 20:
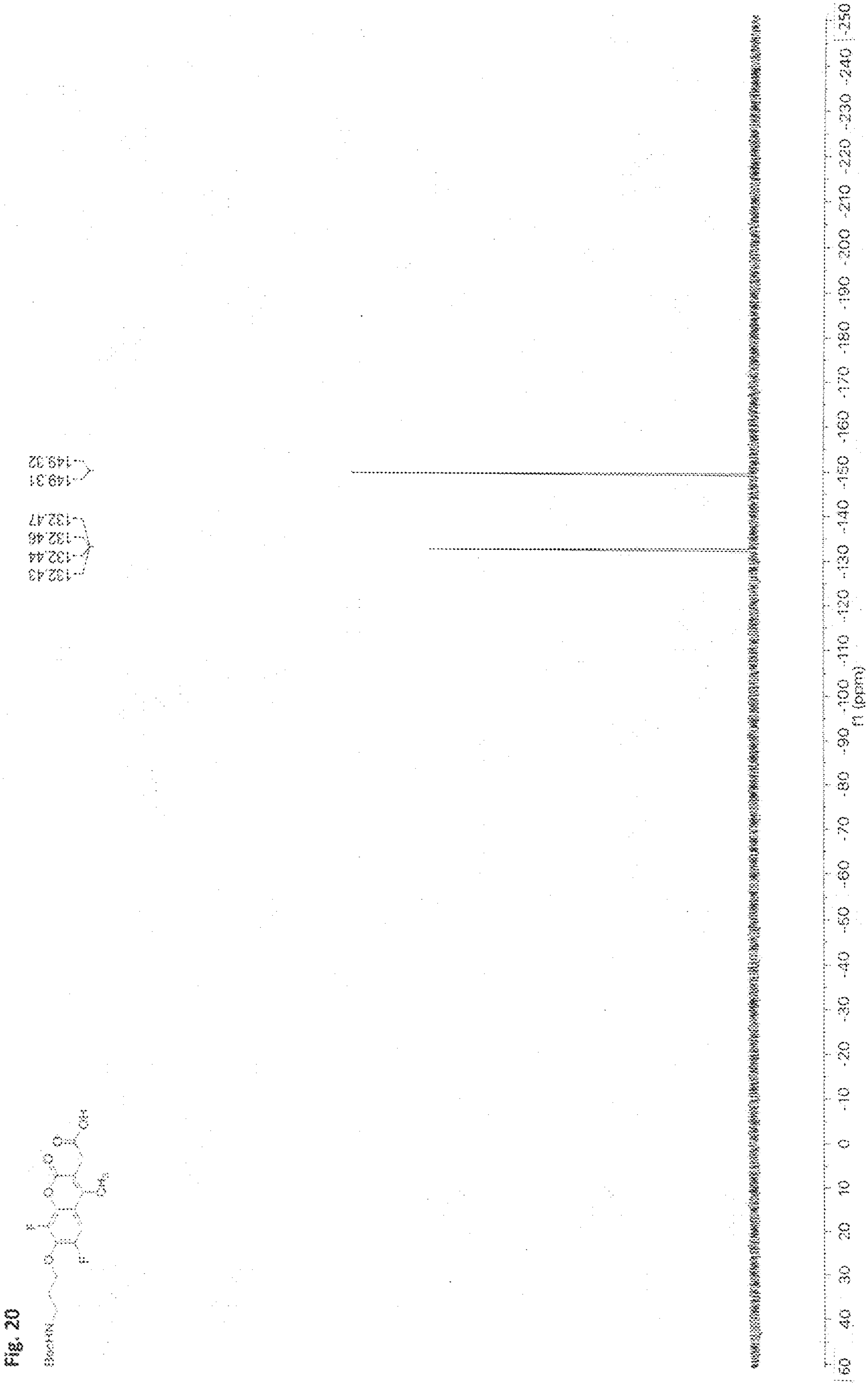

FIG. 20 shows the $^{19}F$ NMR F-H coupled spectrum of Compound 1 in DMSO-$d_6$ (376 MHz).

Figure 21:
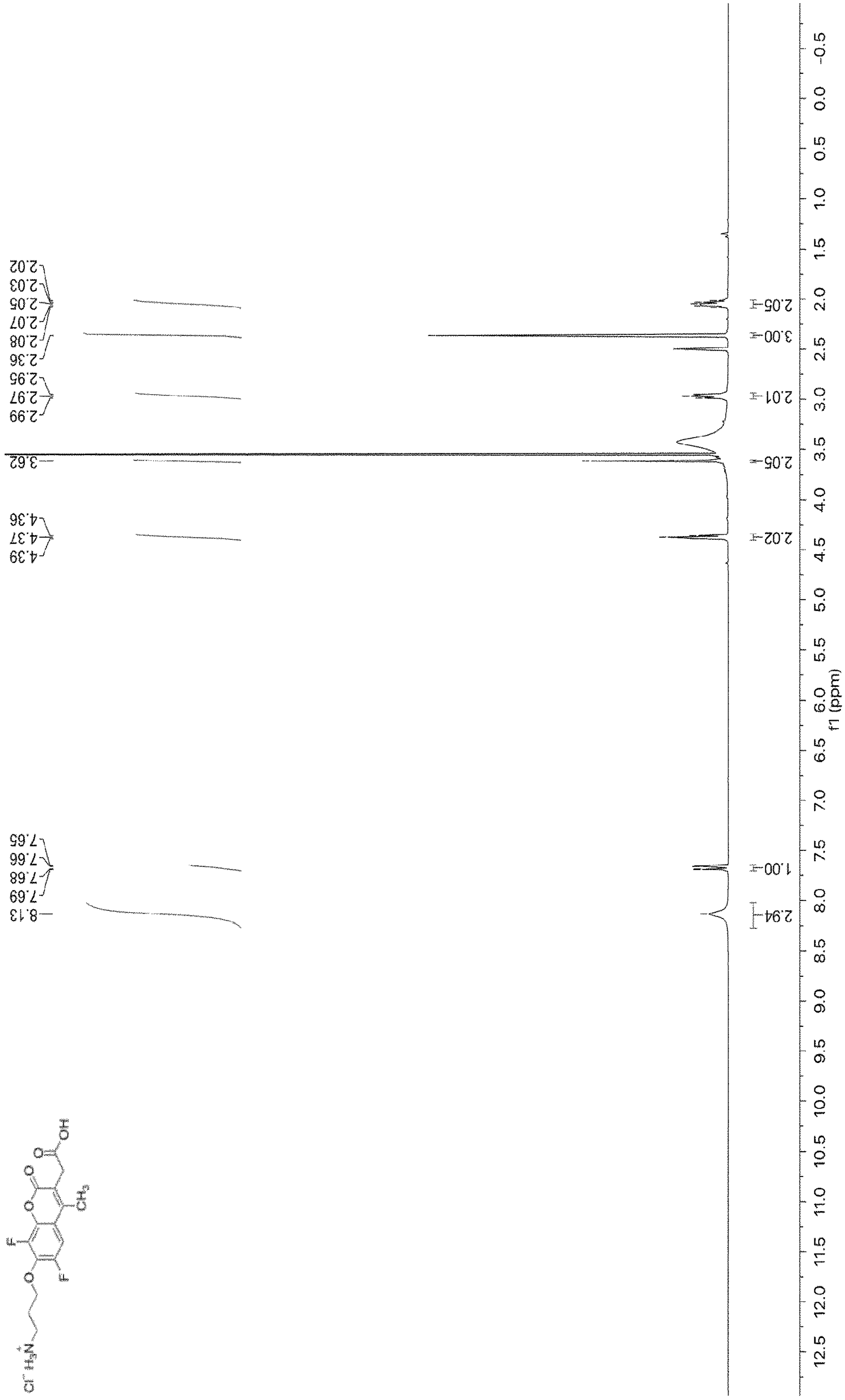
Figure 21:
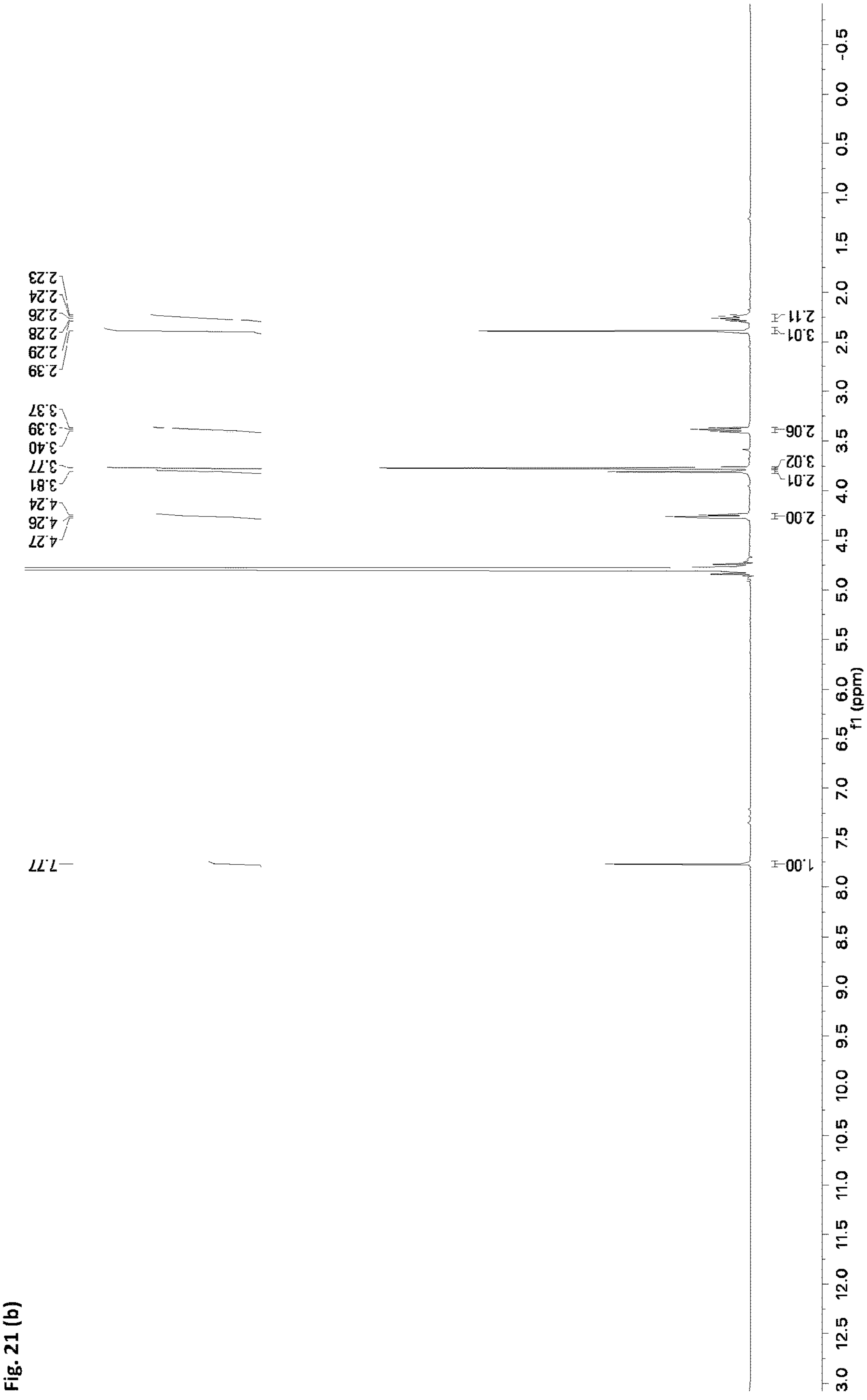

FIG. 21 (*a*) shows the $^1H$ NMR spectrum of Compound 2 in DMSO-$d_6$ (400 MHz). FIG. 21 (*b*) shows the $^1H$ NMR spectrum of 3-methylacetate-6,8-dichloro-7-(4-ammonium-propoxy)-coumarin chloride in $D_2O$ (400 MHz).

Figure 22:
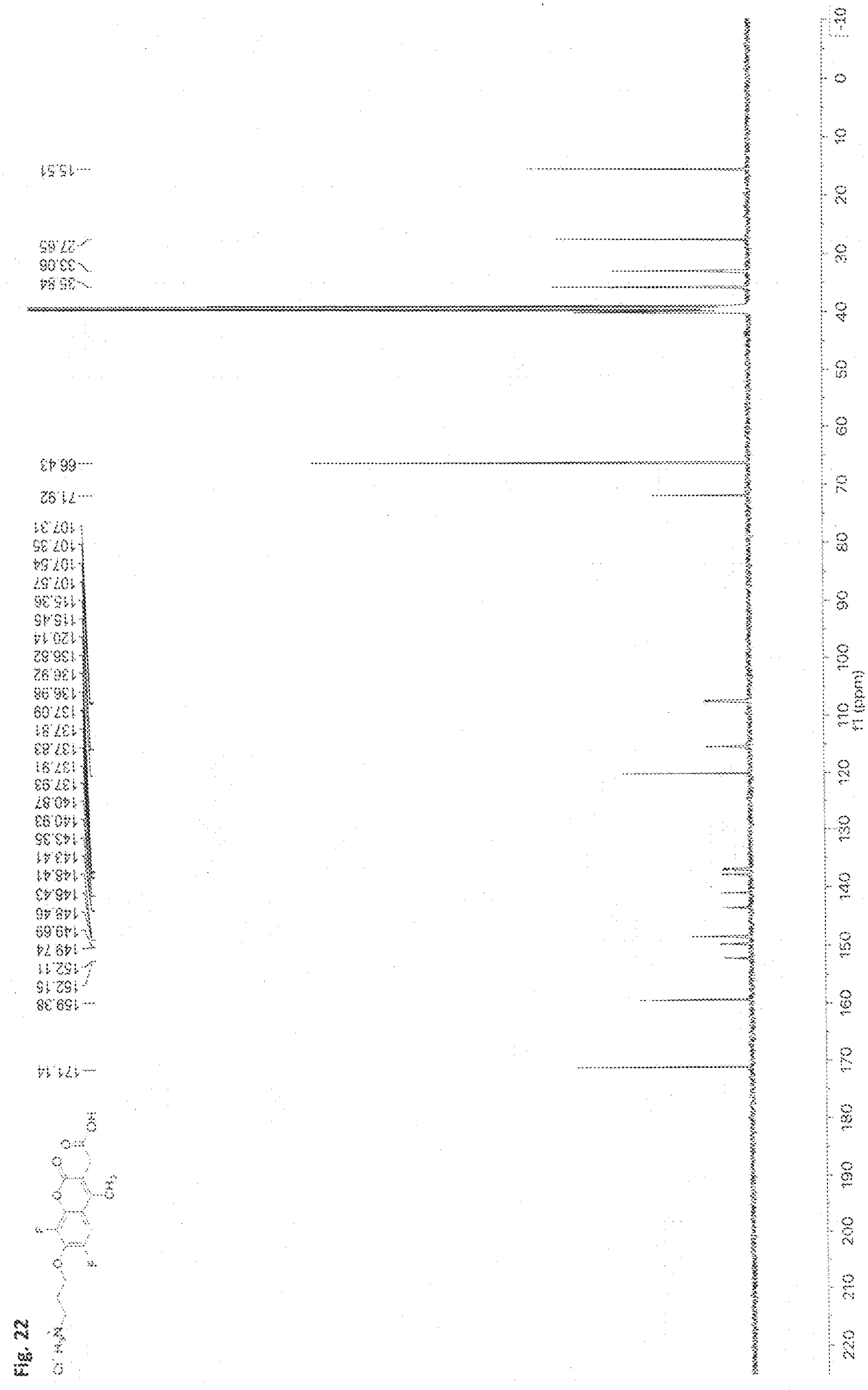

FIG. 22 shows the $^{13}C$ NMR spectrum of Compound 2 in d6-DMF (101 MHz).

Figure 23:
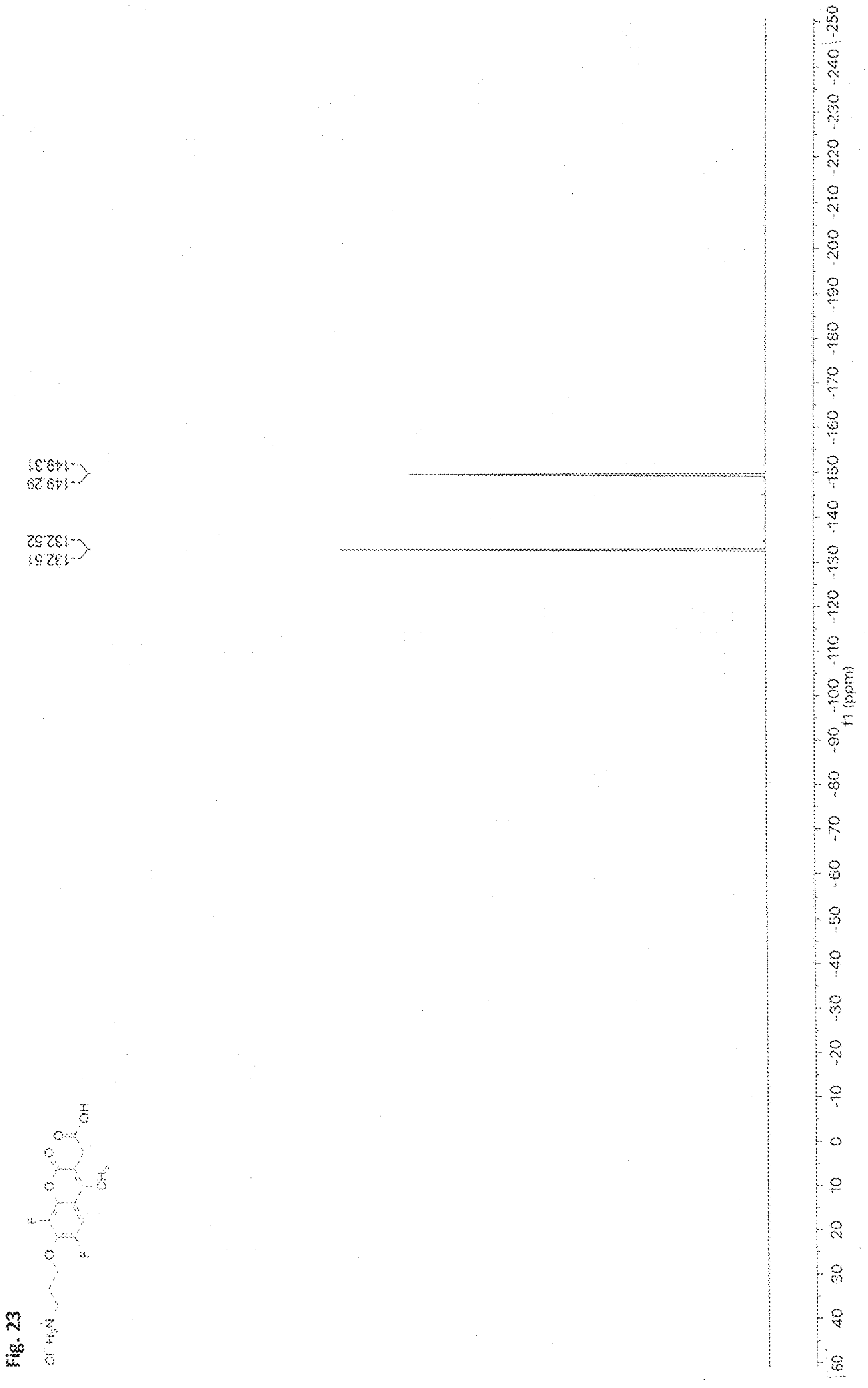

FIG. 23 shows the $^{19}F$ NMR F-H decoupled spectrum of Compound 2 in $CDCl_3$ (376 MHz).

Figure 24:
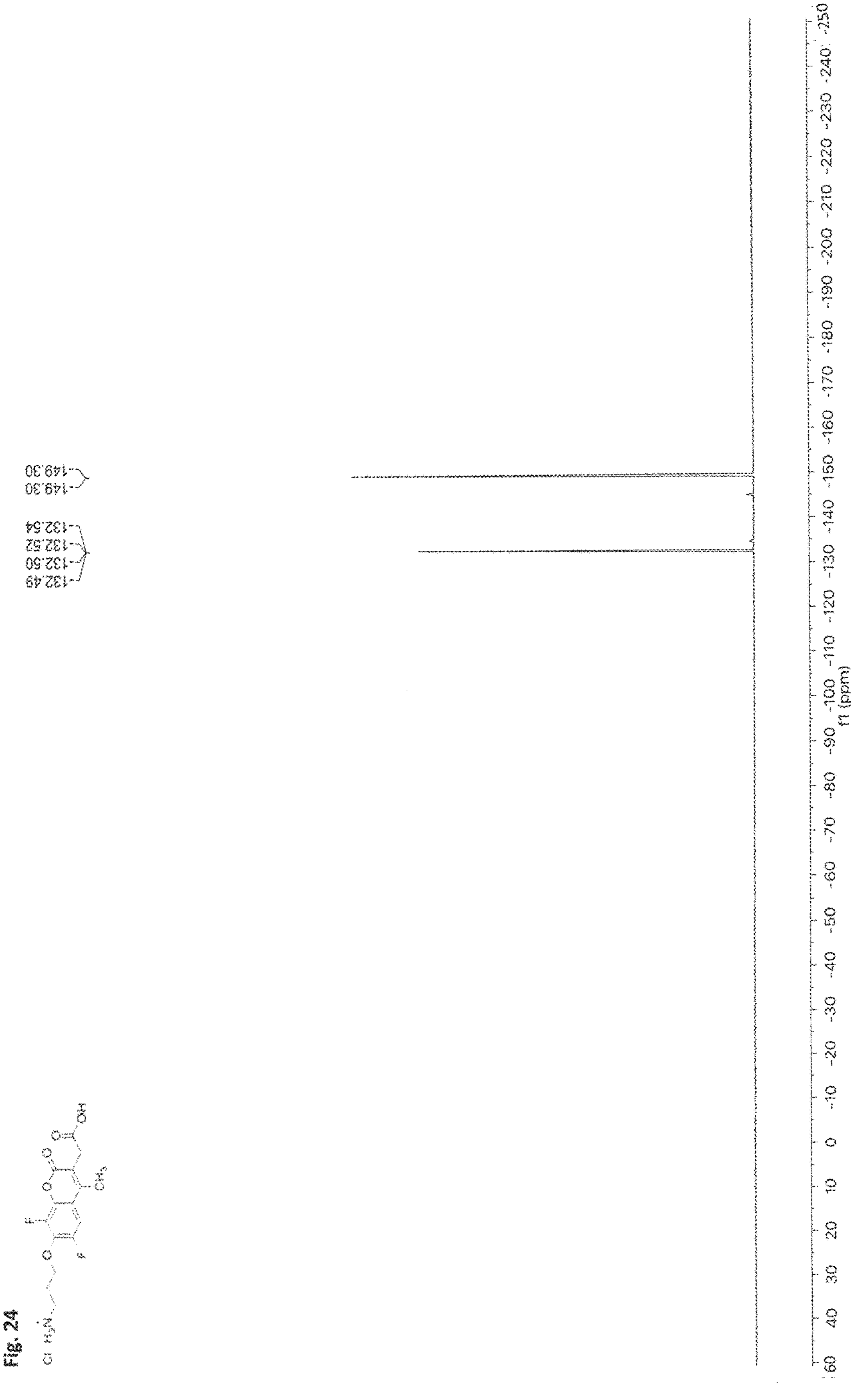

FIG. 24 shows the $^{19}F$ NMR F-H coupled spectrum of Compound 2 in $CDCl_3$ (376 MHz).

Figure 25:
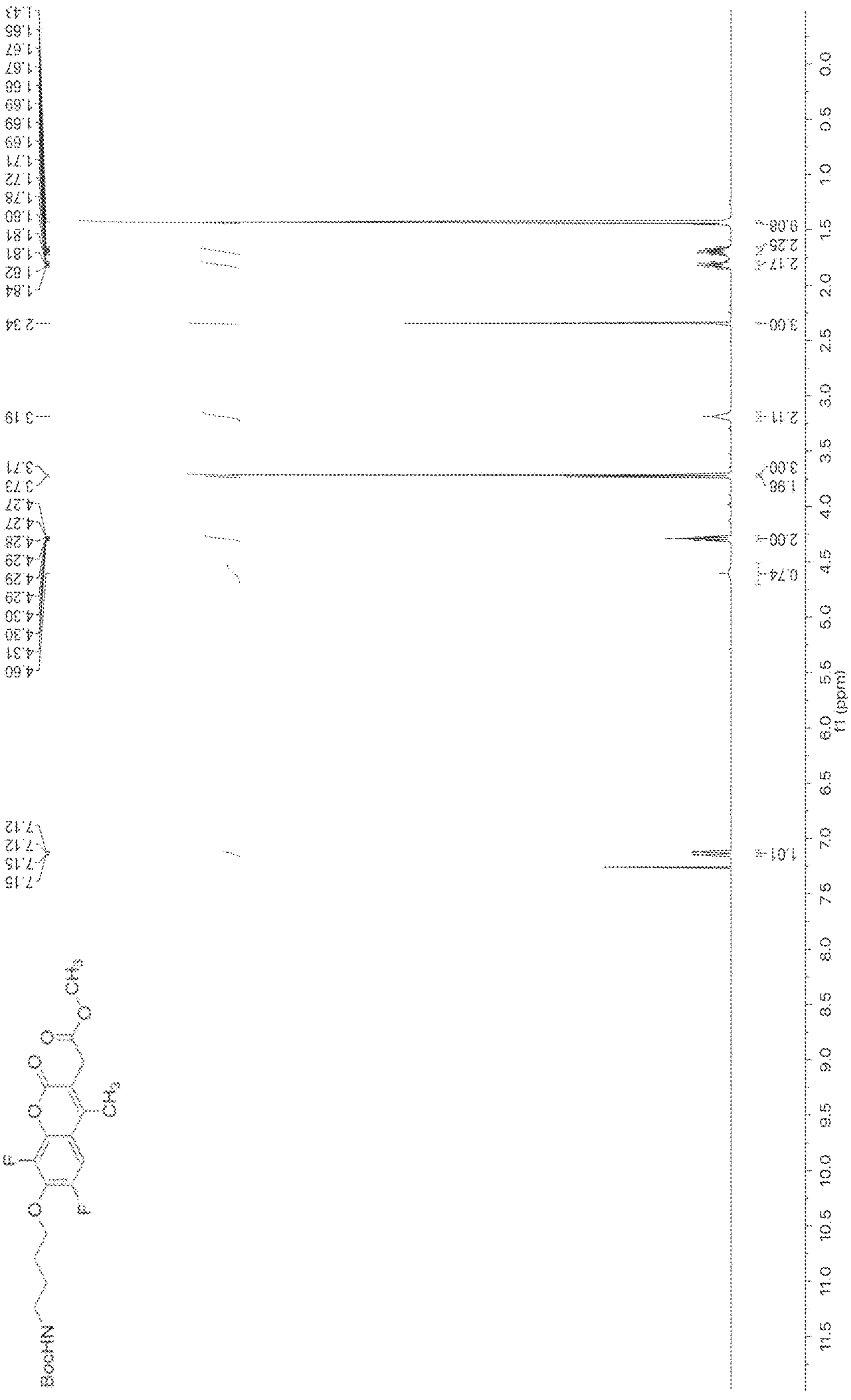

FIG. 25 shows the $^1H$ NMR spectrum of MRA_3068 in $CDCl_3$ (400 MHz).

Figure 26:
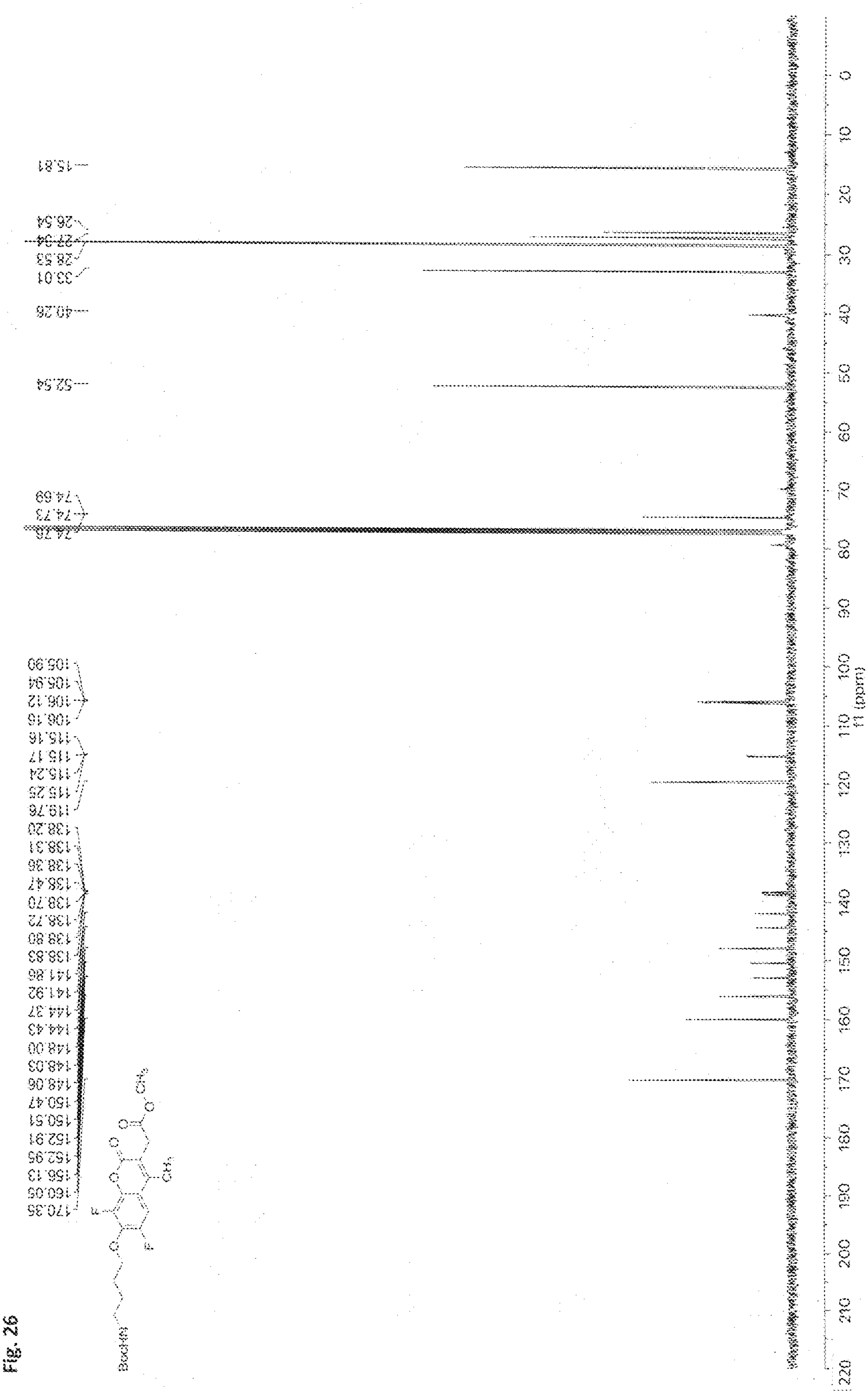

FIG. 26 shows the $^{13}C$ NMR spectrum of MRA_3068 in $CDCl_3$ (101 MHz).

Figure 27:
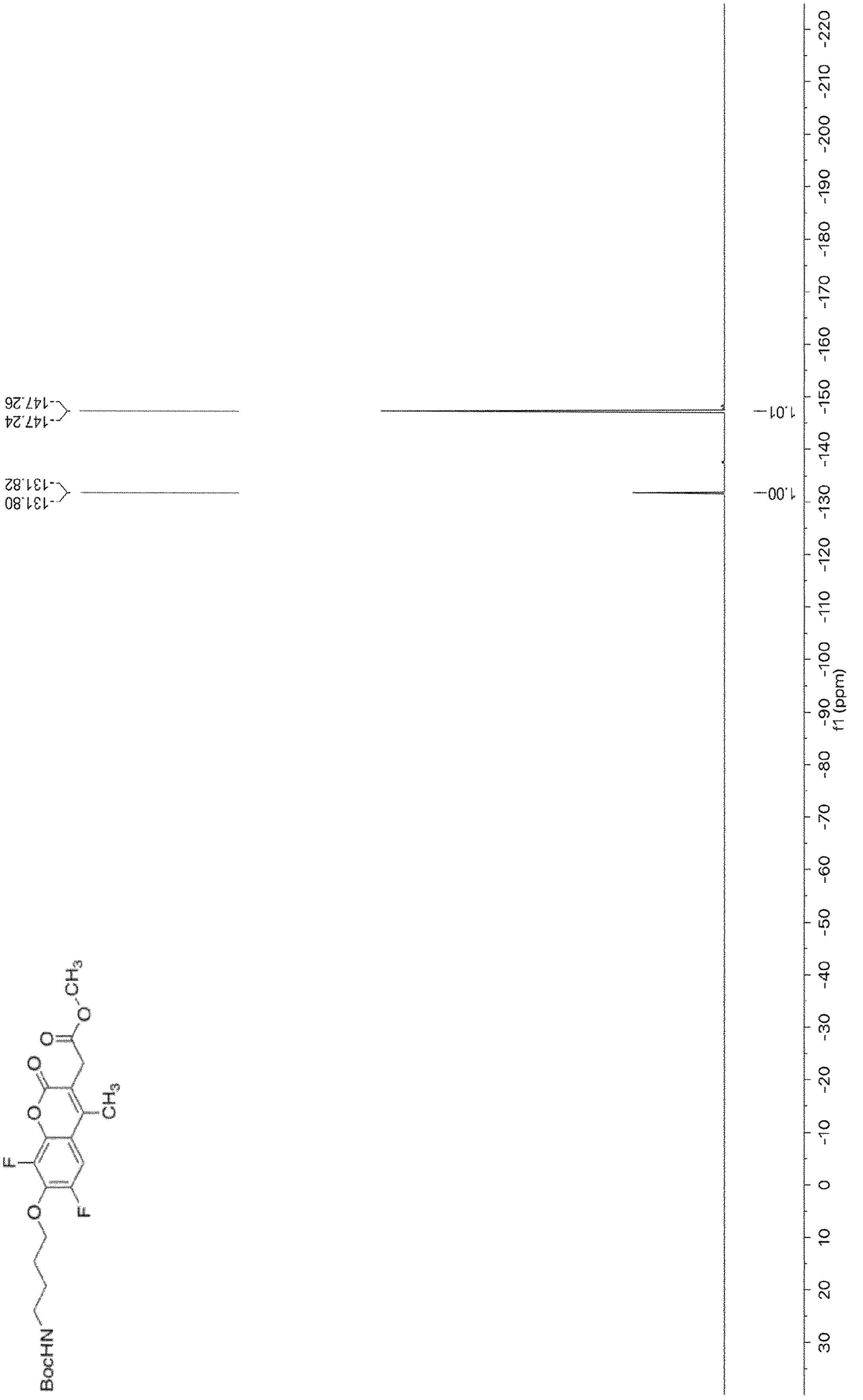

FIG. 27 shows the $^{19}F$ NMR (F-H decoupled) spectrum of MRA_3068 in $CDCl_3$ (376 MHz).

Figure 28:
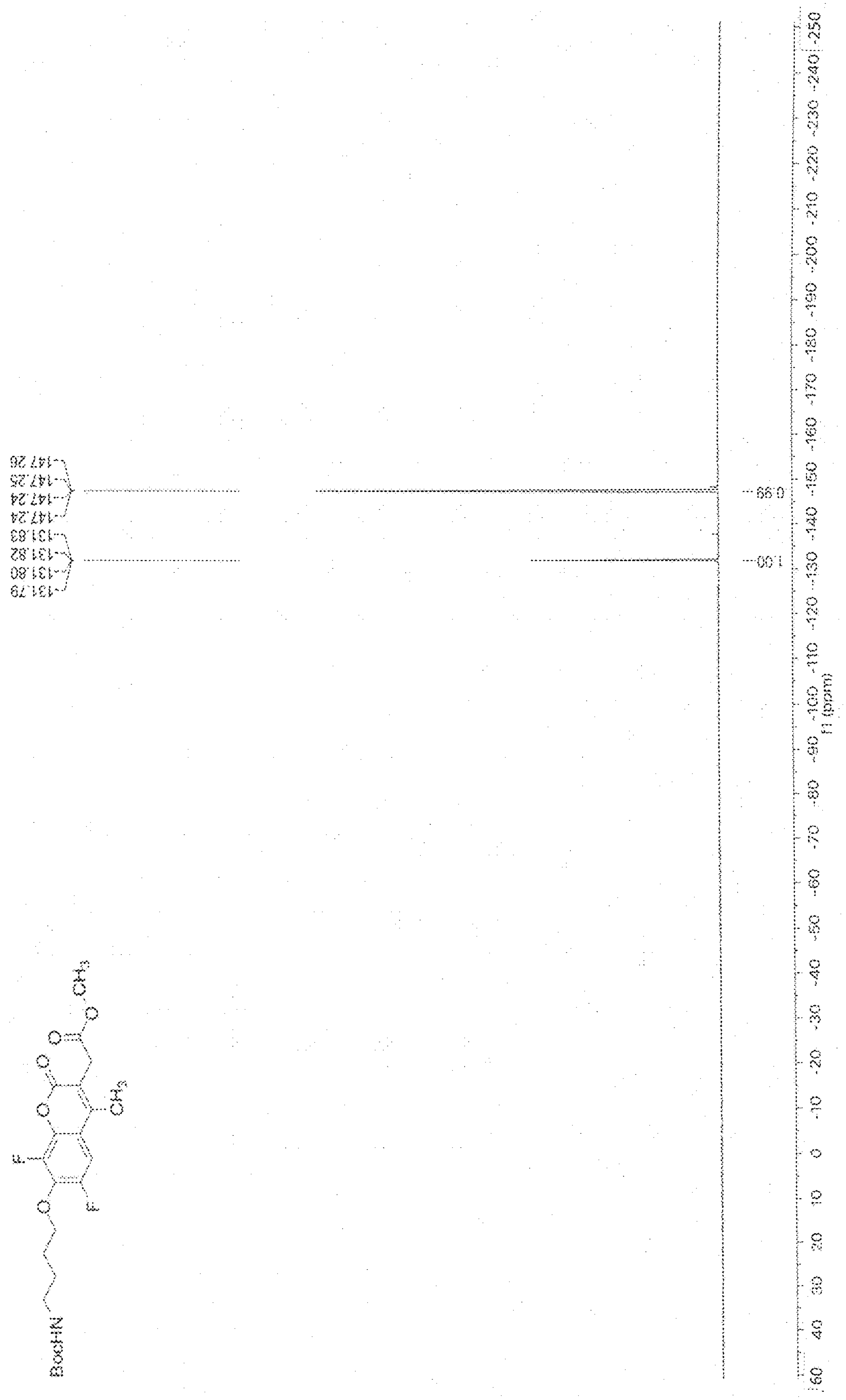

FIG. 28 shows the $^{19}F$ NMR spectrum of MRA_3068 in $CDCl_3$ (376 MHz).

Figure 29:
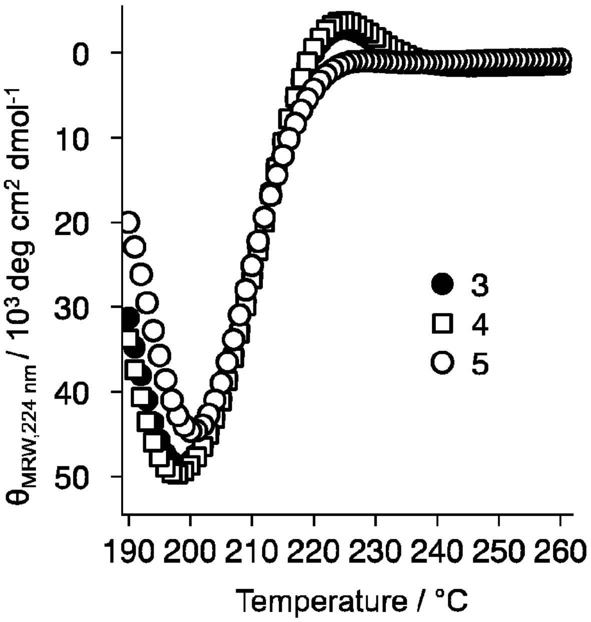

FIG. 29 shows the CD spectra of Compounds 3, 4 and 5.

Figure 30:
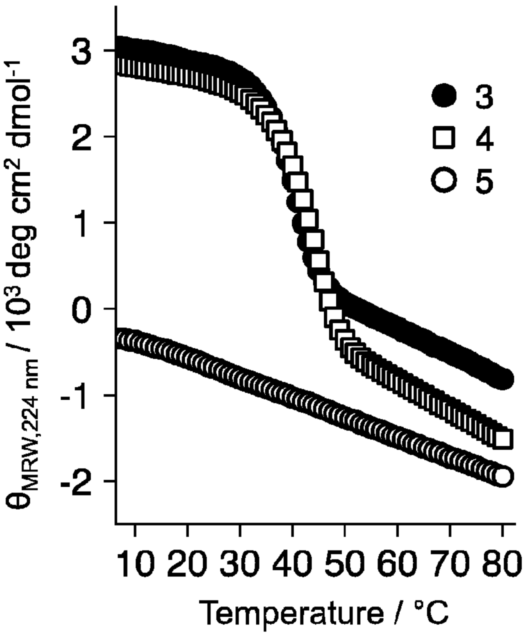

FIG. 30 shows the thermal denaturation curves of Compounds 3, 4 and 5.

Figure 31:
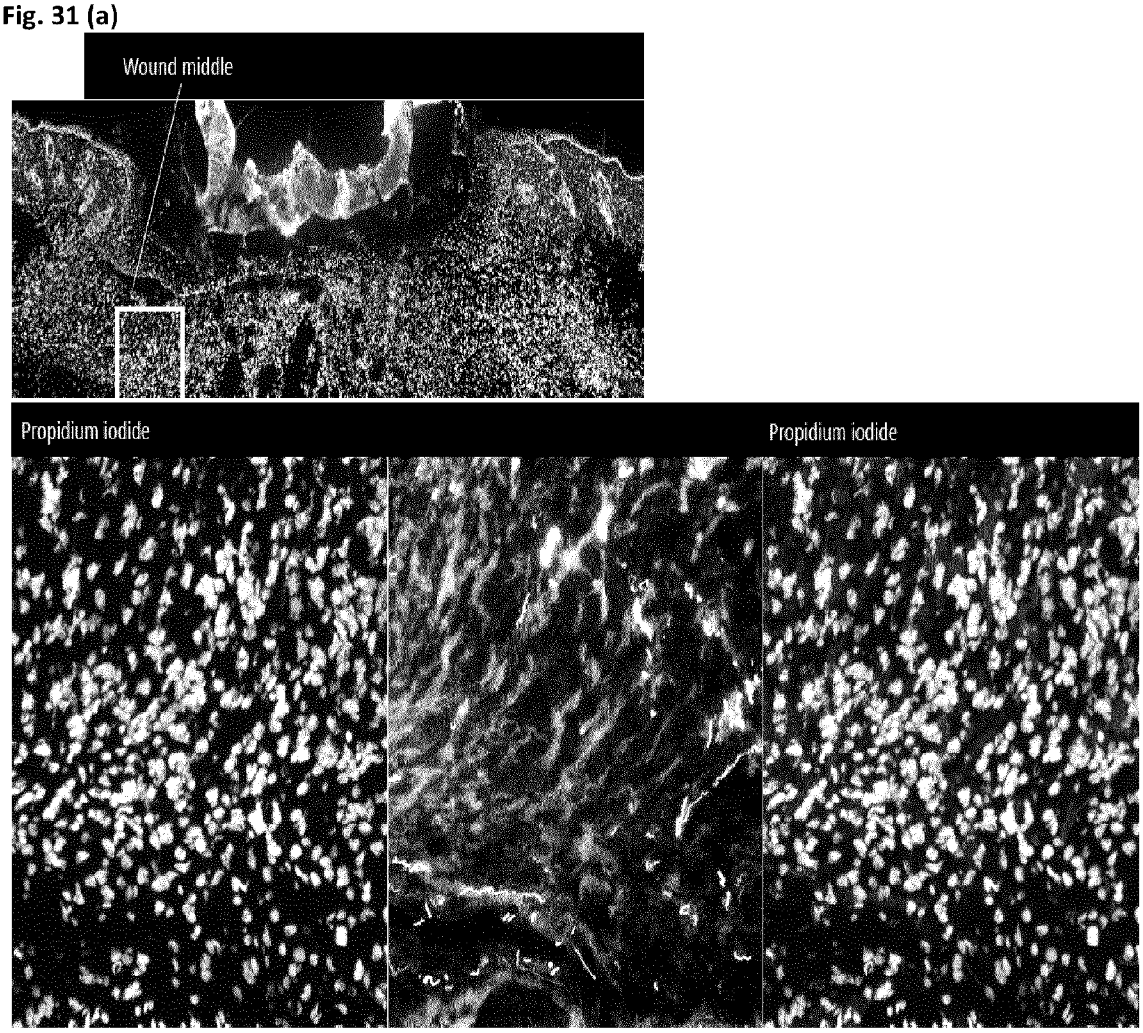
Figure 31:
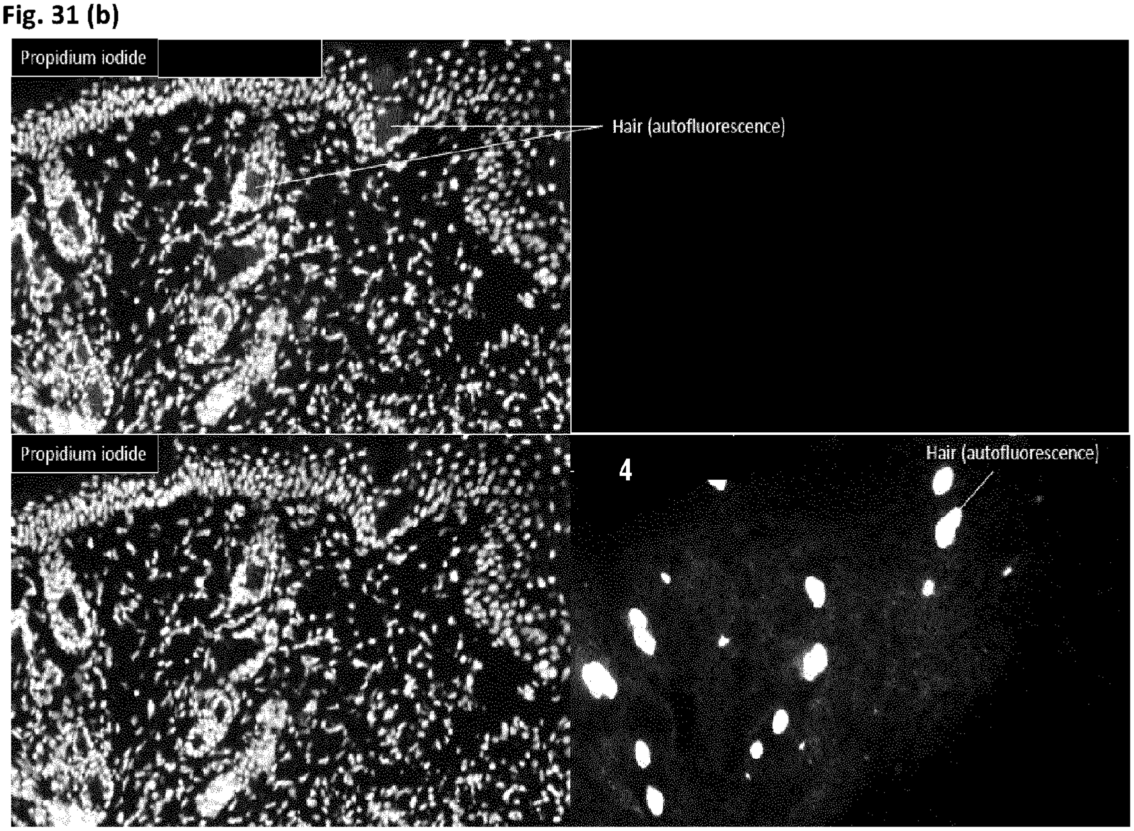
Figure 31:
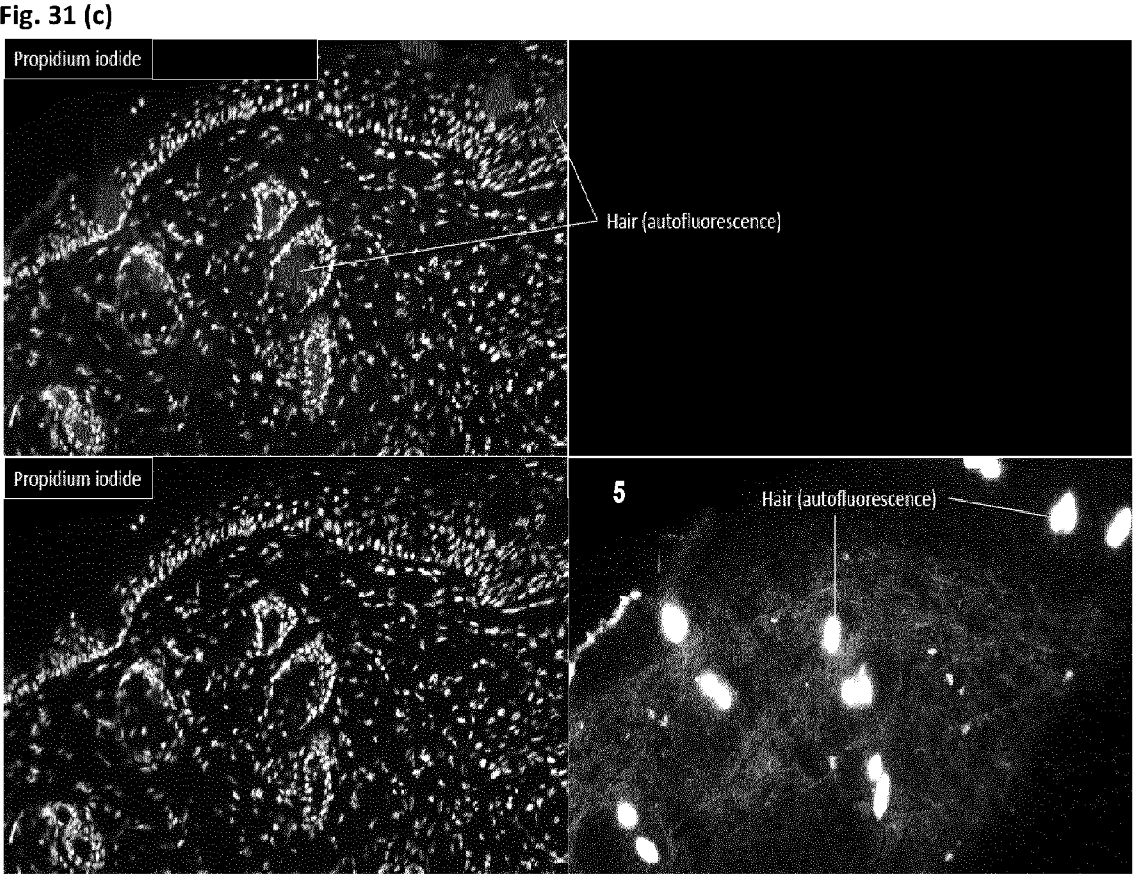

FIG. 31 (*a*), FIG. 31 (*b*), and FIG. 31 (*c*) show the analysis of skin tissue after in vivo administration of (a) Compound 3 (b) Compound 4 and (c) Compound 5 to mice. In these images of the cross section of a wound fluorescence can be clearly visualized at the locations where the peptide-bound probe has been unmasked by reacting in vivo with an amine-oxidase (blue color) in and around the sites of injection. In FIG. 31 (*a*), the top image shows the context of the lower three images. FIG. 31 (*a*) (center) proves that the compound localizes the probe to collagen and elastin at the sites of LOX-mediated crosslinking during new tissue growth and maturation in the wound within a living organism, and demonstrates that the compounds according to the present invention can be used in vivo for targeting and analysis of collagen crosslinking in the extracellular matrix, such as, e.g., that which occurs during fibrosis.

Figure 32:
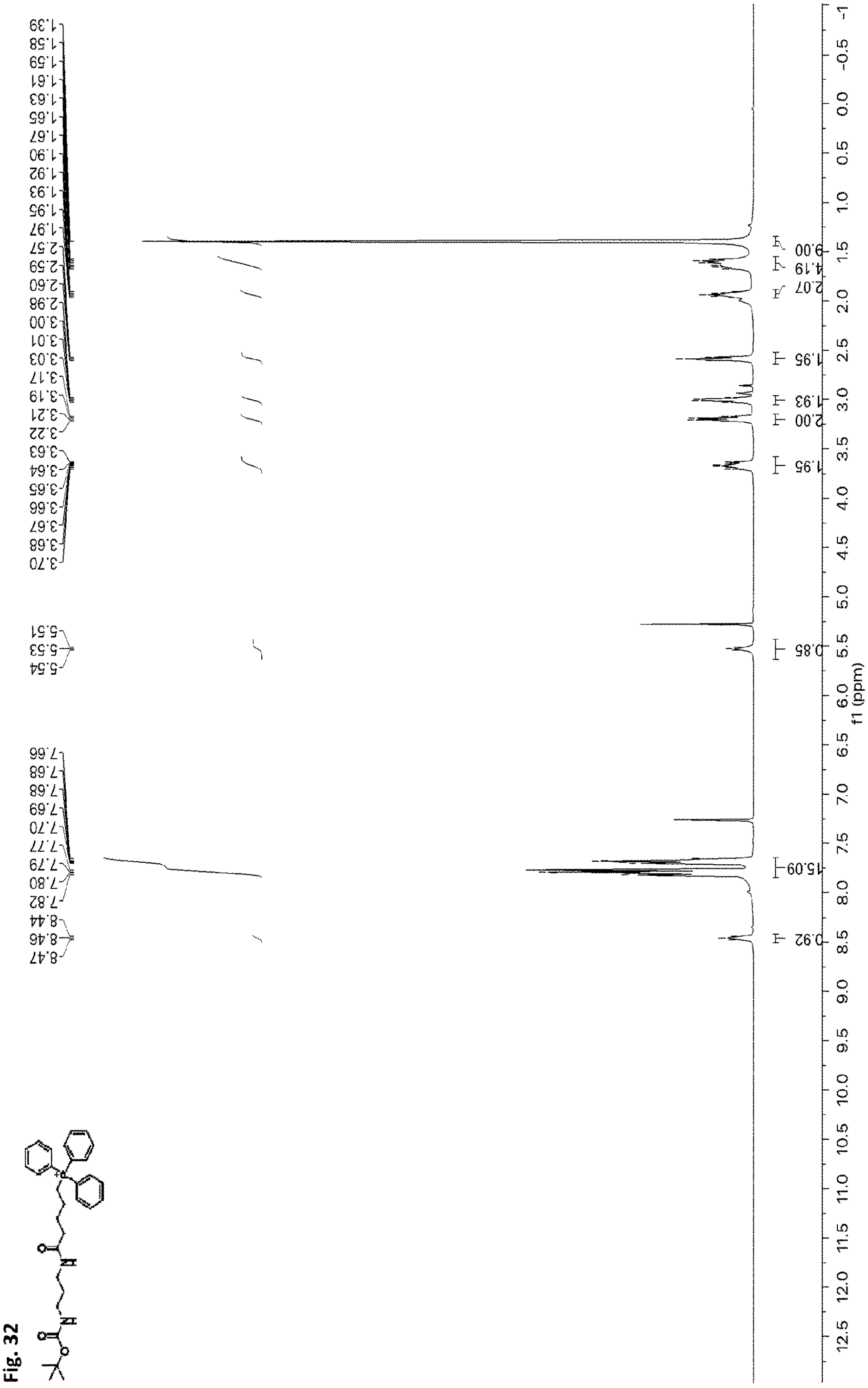

FIG. 32 shows the $^1H$ NMR spectrum of MRA_3100 in $CDCl_3$ (400 MHz).

Figure 33:
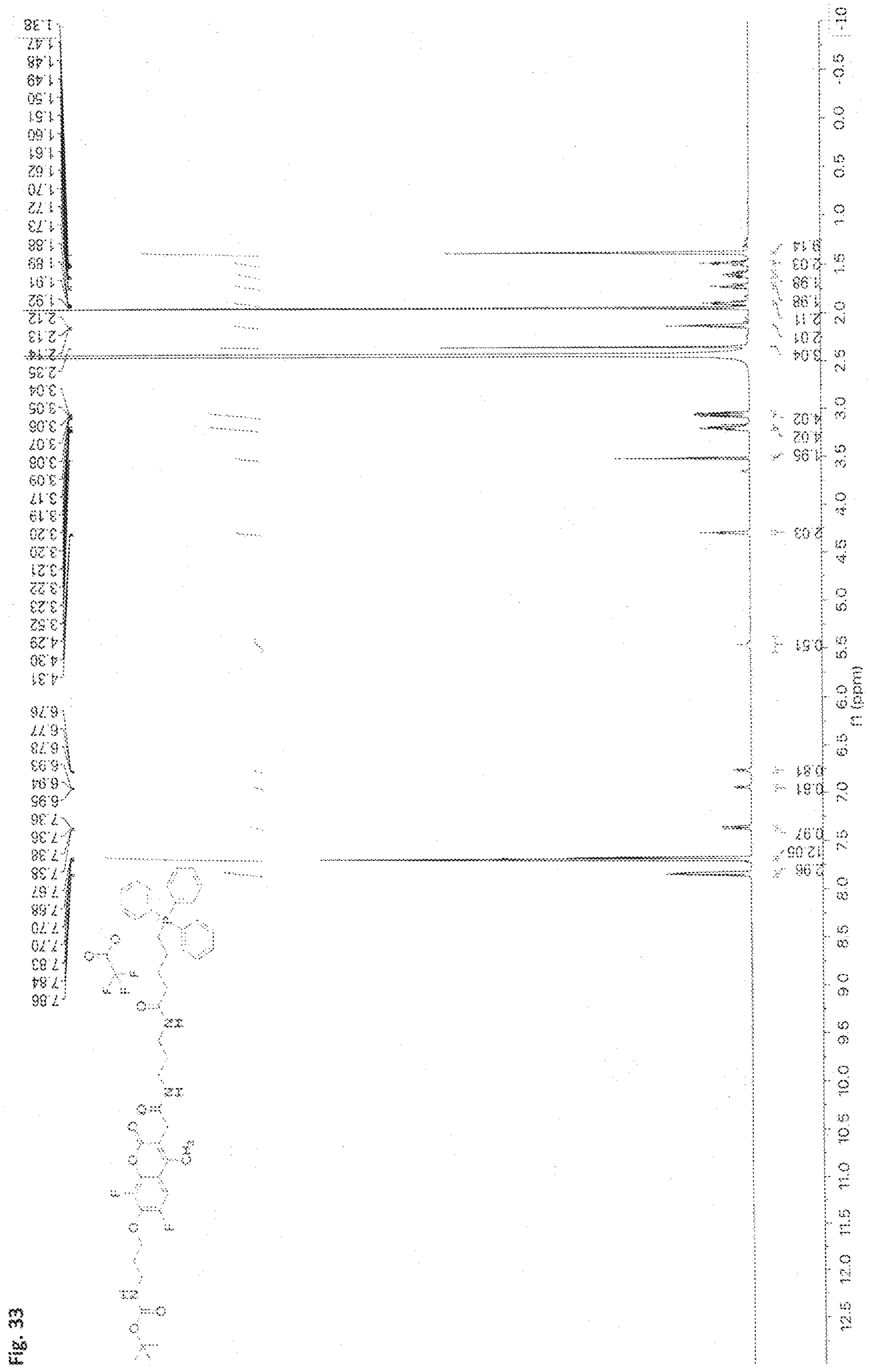

FIG. 33 shows the $^1H$ NMR spectrum of MRA_3103 in $CD_3CN$ (600 MHz).

Figure 34:
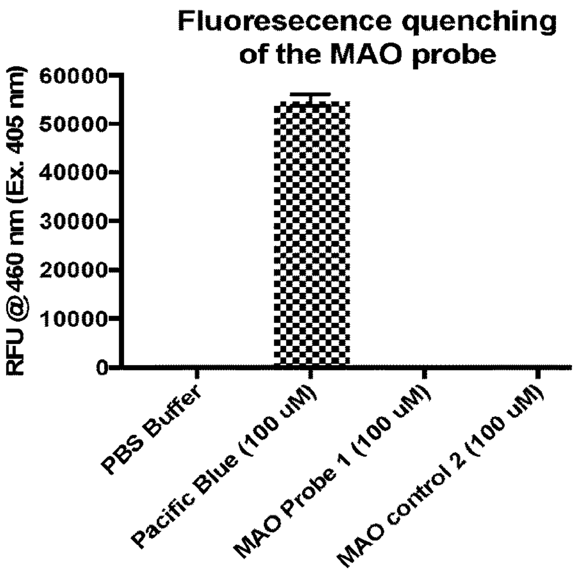
Figure 34:
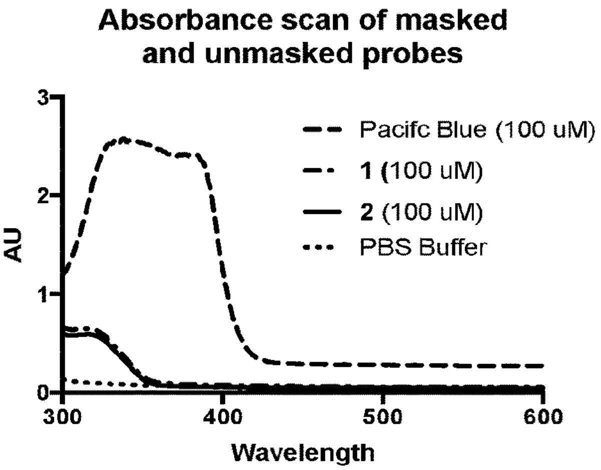
Figure 35:
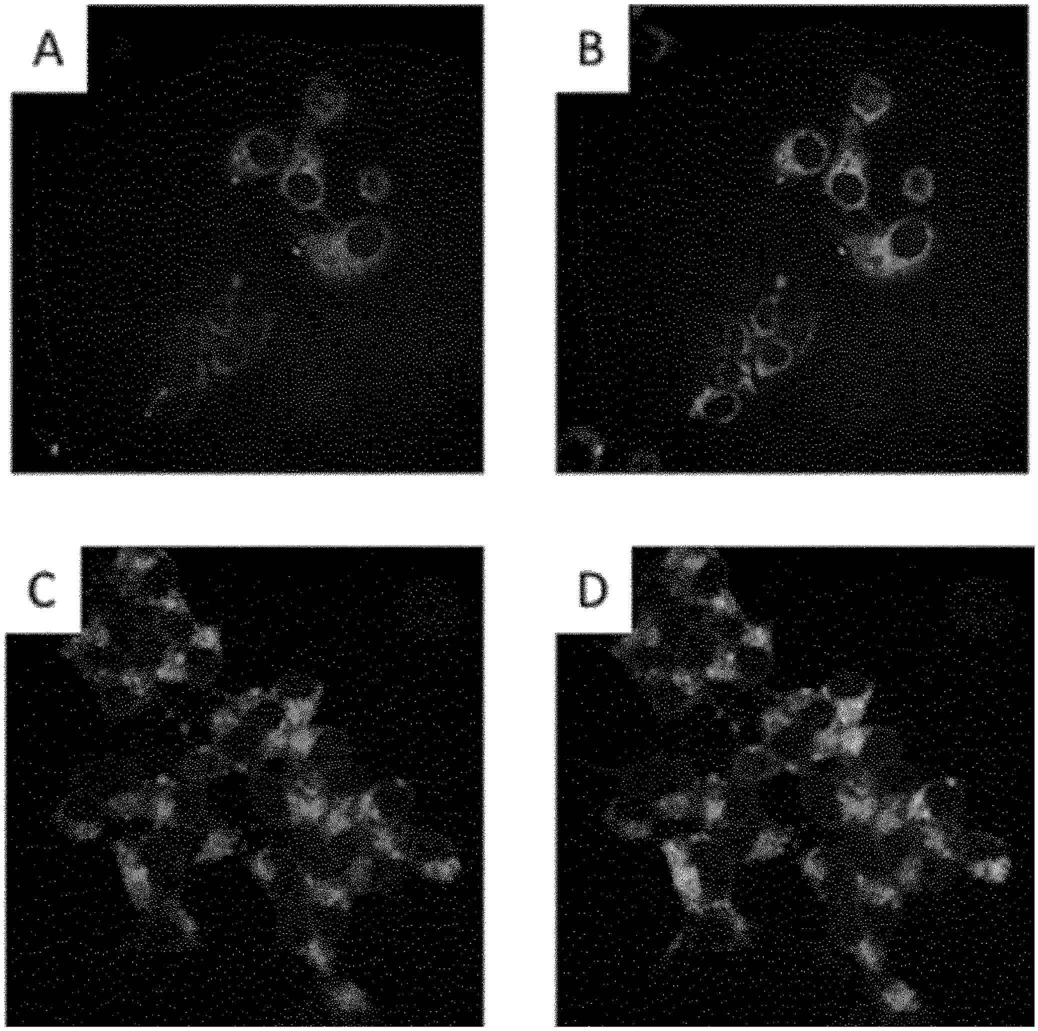
Figure 36:
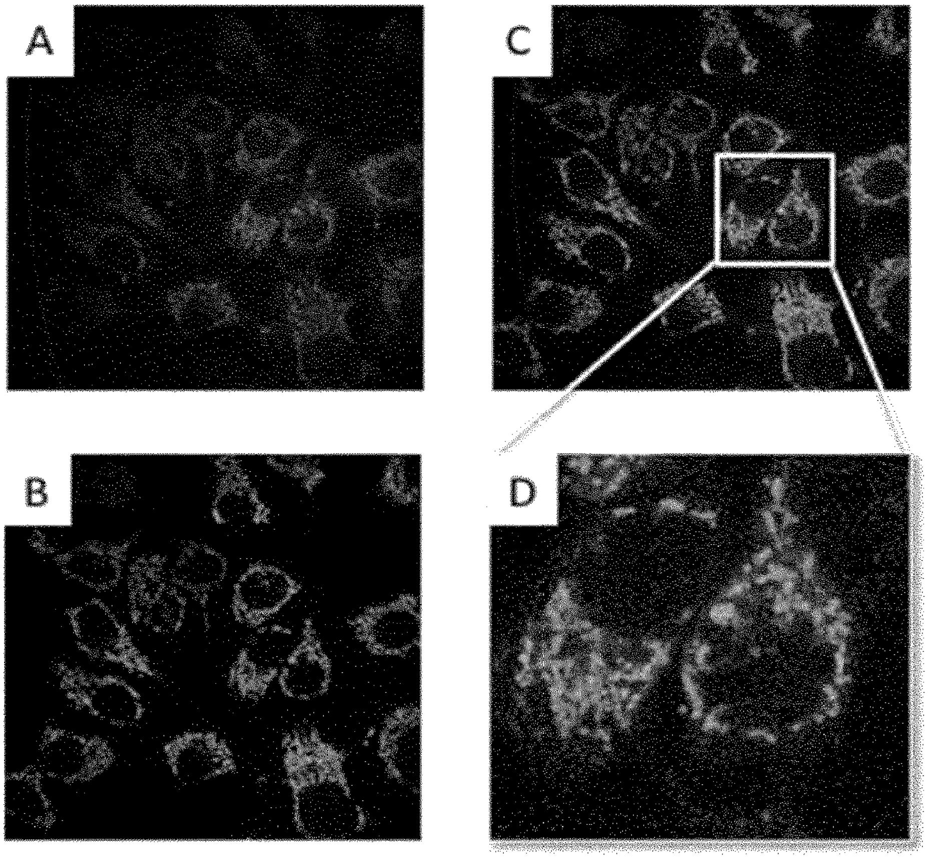
Figure 37:
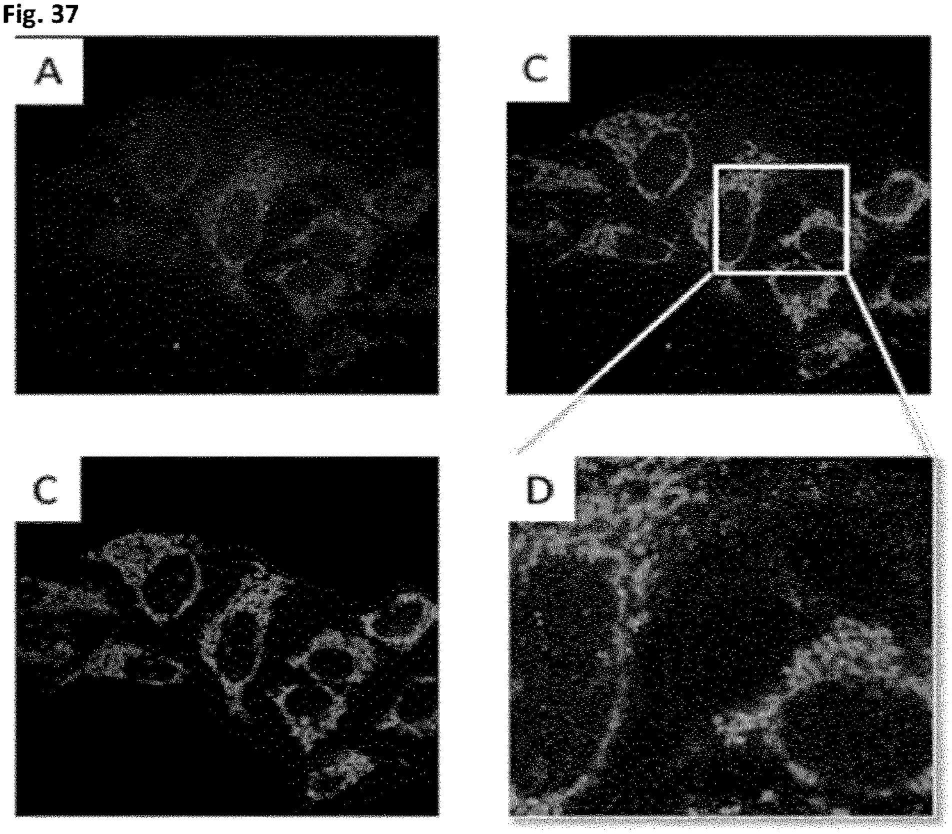

FIG. 34 (*a*) shows the fluorescence signals of MAO probes showing the efficiency of fluorescence quenching for probe 1 and for control 2 versus Pacific Blue'. Fluorescent signals are shown as relative fluorescence units (RFU) when excited at 405 nm and measured at 460 nm (Ex/Em respectively). Error bars represent SD, $n=3$. FIG. 34 (*b*) shows the absorbance scans from 300 to 600 nm of MAO probes showing the efficiency of quenching via the shift in absorbance maximum from 360 nm to approximately 315 nm as well as a decrease in absorbance for probe 1 and for control 2 versus Pacific Blue'. Transmittance is shown as absorbance units (AU).

FIG. 35A, FIG. 35B, FIG. 35C, and FIG. 35D show confocal microscopy images of cells following treatment with MAO probe. Top: MCF-7 cells were treated with MRA_3100 (10 mM) for 3 h, followed by staining with MitoTracker Red. (FIG. 35A) Blue channel (405 nm) shows activation and fluorescence of the probe, and (FIG. 35B) Overlay of the blue and red channels (405 nm and 561 nm) showing colocalization of the probe and dye in mitochondria. Bottom: SY5Y cells were treated with MRA_3100 (10 mM) for 3 h, followed by staining with MitoTracker Red. (FIG. 35C) Blue channel (405 nm) shows activation and fluorescence of the probe, and (FIG. 35D) Overlay of the blue and red channels (405 nm and 561 nm) showing colocalization of the probe and dye in mitochondria.

FIG. 36A, FIG. 36B, FIG. 36C, and FIG. 36D show confocal microscopy images of MCF-7 cells following treatment with peptide MAO probe (10 mM) for 1 h, followed by staining with MitoTracker Red. (FIG. 36A) Blue channel (405 nm) shows activation and fluorescence of the probe, (FIG. 36B) Red channel (561 nm) shows the location of mitochondria inside the cells, (FIG. 36C) Overlay of the blue and red channels (405 nm and 561 nm) showing colocalization of the probe and dye in mitochondria, and (FIG. 36D) Zoom from the inset of FIG. 36C.

FIG. 37A, FIG. 37B, FIG. 37C, and FIG. 37D show confocal microscopy images of MCF-7 cells following treatment with PB peptide (10 mM) for 1 h, followed by staining with MitoTracker Red. (FIG. 37A) Blue channel (405 nm) shows fluorescence of the probe, (FIG. 37B) Red channel (561 nm) shows the location of mitochondria inside the cells, (FIG. 37C) Overlay of the blue and red channels (405 nm and 561 nm) showing a lack colocalization between the probe and mitochondrially-located red dye, and (FIG. 37D) Zoom from the inset of FIG. 37C.

Figure 38:
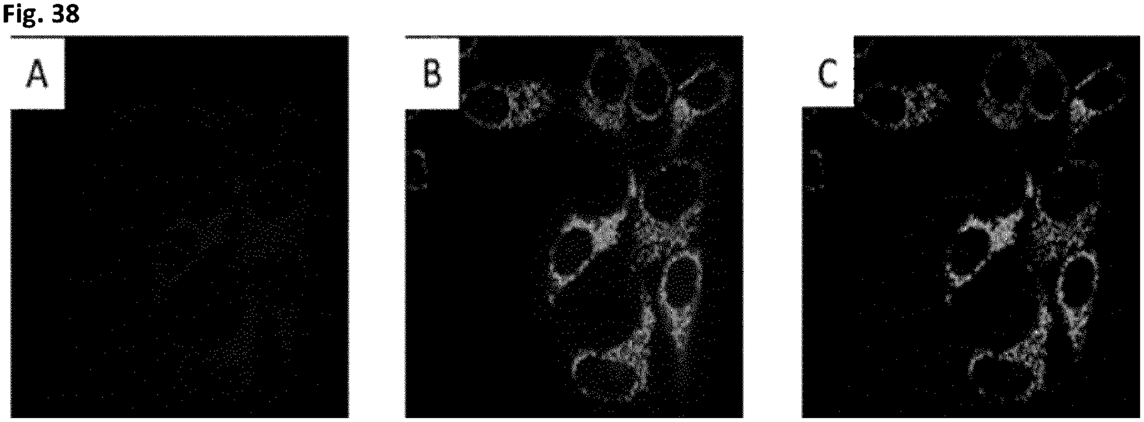

FIG. 38A. FIG. 38B, and FIG. 38C show confocal microscopy images of MCF-7 cells following treatment with peptide MAO probe (10 mM) for 1 h, followed by staining with MitoTracker Red. (FIG. 38A) Blue channel (405 nm) shows no fluorescence from the probe as it cannot be activated by MAO enzymes, (FIG. 38B) Red channel (561 nm) shows the location of mitochondria inside the cells, (FIG. 38C) Overlay of the blue and red channels (405 nm and 561 nm) show only the mitochondrially-located red dye.

Figure 39:
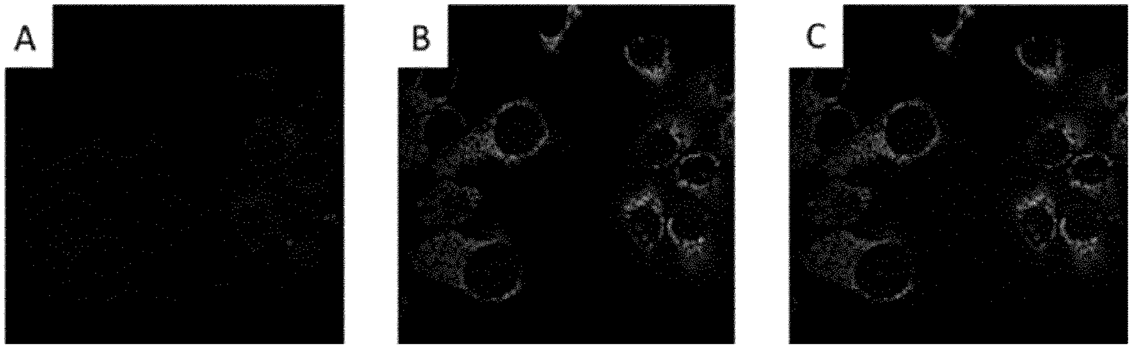

FIG. 39A, FIG. 39B, and FIG. 39C show confocal microscopy images of MCF-7 cells following a 1 h pretreatment with the MAO-B inhibitor (R)—N,α-Dimethyl-N-2-propynylphenethylamine (Selegiline), and subsequent treatment with the peptide MAO probe (10 mM) for 1 h, followed by staining with MitoTracker Red. (FIG. 39A) Blue channel (405 nm) shows very little fluorescence from the probe, (FIG. 39B) Red channel (561 nm) shows the location of mitochondria inside the cells, (FIG. 39C) Overlay of the blue and red channels (405 nm and 561 nm) show only poor colocalization between the probe and the mitochondrially-located red dye.

Figure 40:
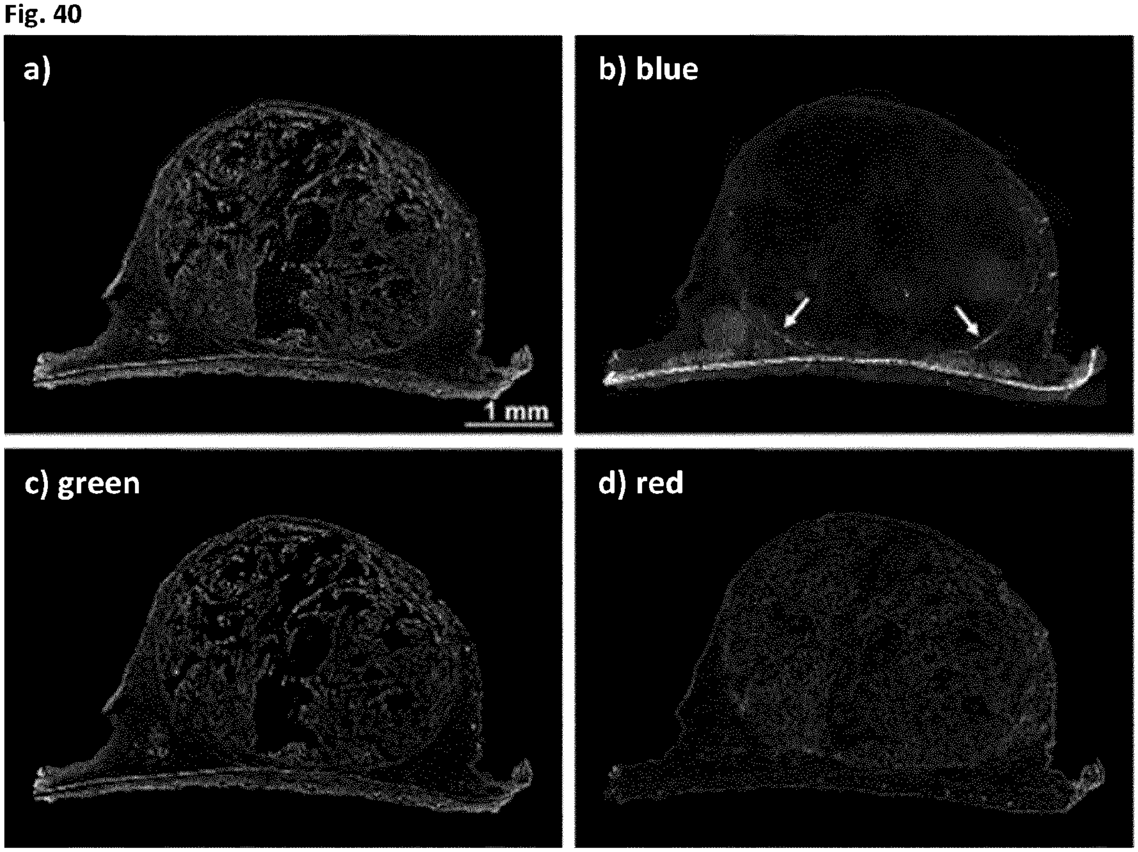

FIG. 40(*a*), FIG. 40(*b*), FIG. 40(*c*), and FIG. 40(*d*) show a collage of 10× images displaying the entire section (FIG. 40(*a*)) of an SSC13 ear tumor following FIG. 40(*b*) staining with Compound 3 (blue), FIG. 40(*c*) immunostaining for collagen I (green), and FIG. 40(*d*) nuclei staining with propidium iodide (red). Single channel images show black and white representation of fluorescence. Blue fluorescence of the probe is seen around the periphery of the tumor but is strongest near the side of attachment to the cartilage (arrows).

Figure 41:
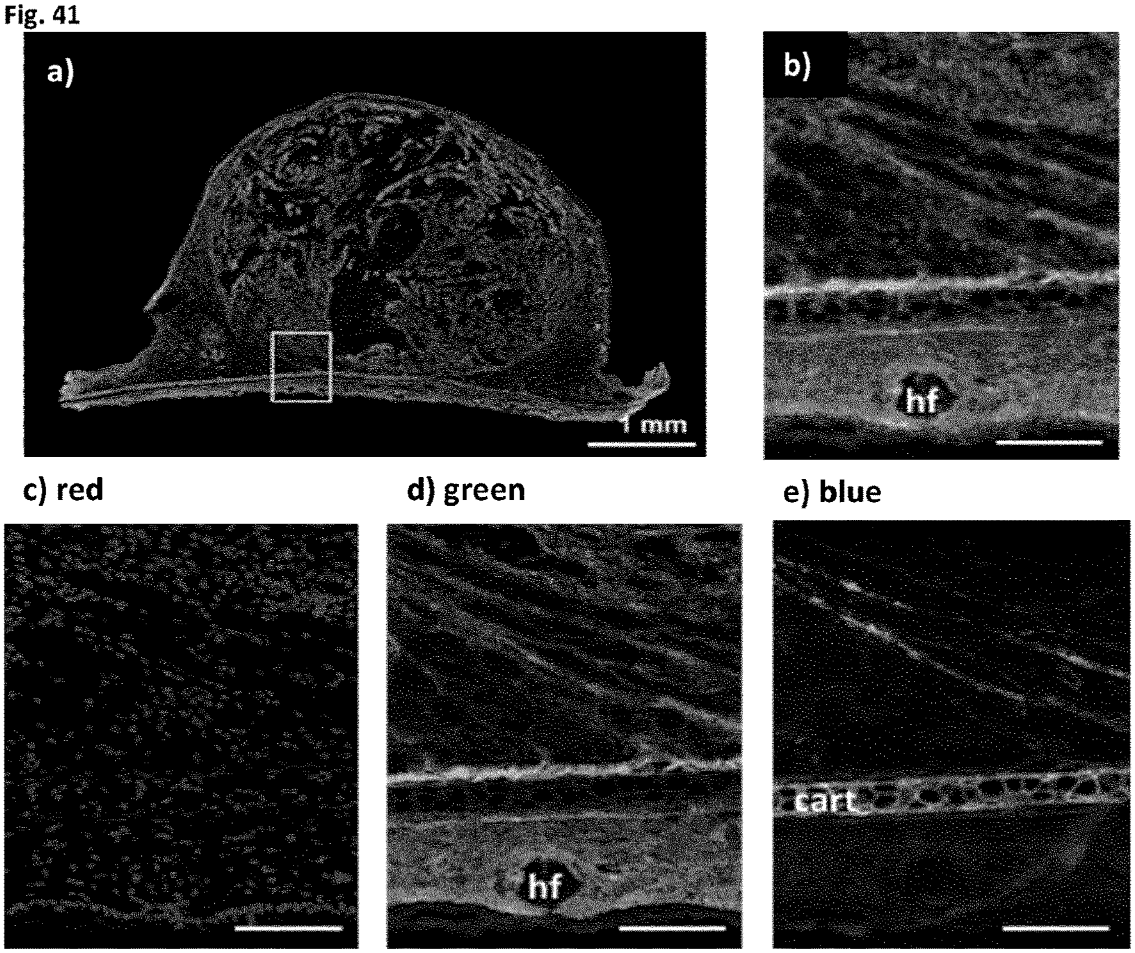

FIG. 41(*a*), FIG. 41(*b*), FIG. 41(*c*), FIG. 41(*d*), and FIG. 41(e) show the merged 20× image of an SSC13 ear tumor following staining (FIG. 41(*a*) and FIG. 41(*b*)), and single channel representation (FIG. 41 (*c*) to FIG. 41(*e*)). Nuclei staining with propidium iodide (FIG. 41(*c*), red), immunostaining for collagen I (FIG. 41(*d*), green), and blue fluorescence (FIG. 41(*e*)) from the probe seen around the periphery of the tumor is strongest near the side of attachment to the cartilage, but does not appear in the dermis on the opposite side of the cartilage. Cartilage (cart) fluorescence and hair follicles (hf) can also be observed. Scale bar=100 μm.

Figure 42:
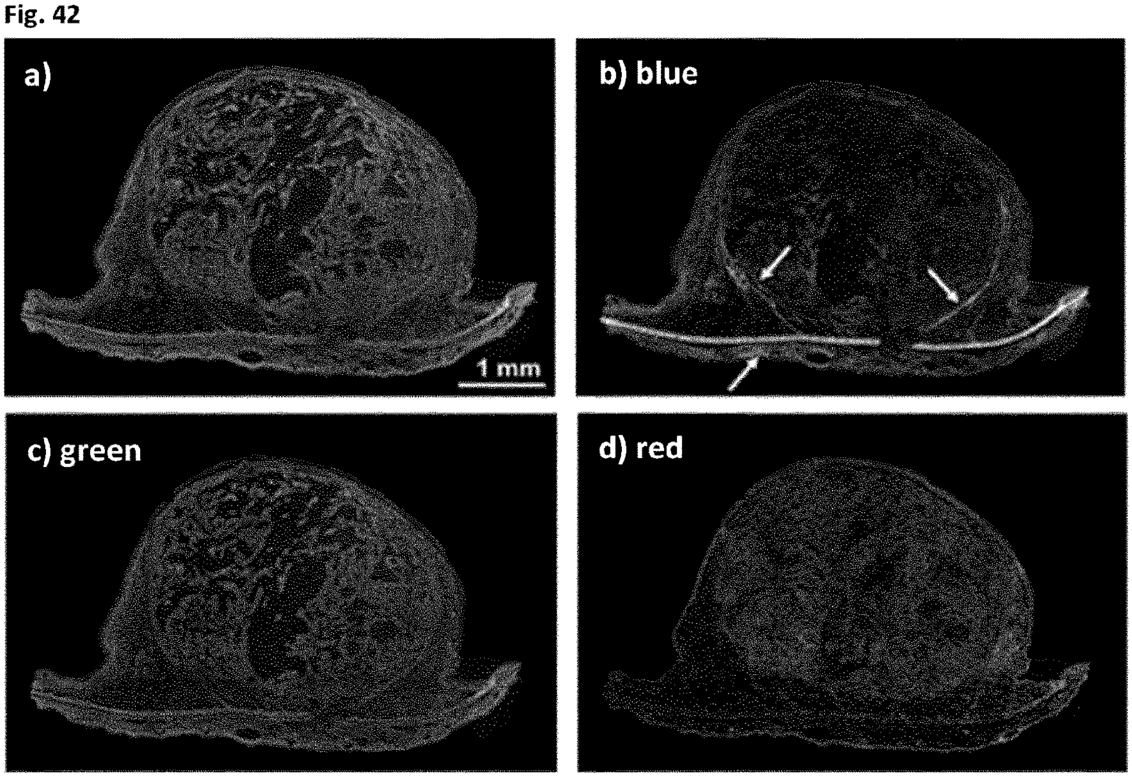

FIG. 42(*a*), FIG. 42(*b*), FIG. 42(*c*), and FIG. 42(*d*) show a collage of 10× images displaying the entire section of an SSC13 ear tumor (FIG. 42(*a*)) following staining with Compound 6 (FIG. 42(*b*), blue), immunostaining for collagen I (FIG. 42(*c*), green), and nuclei staining with propidium iodide (FIG. 42(*d*), red). Single channel images show black and white representation of fluorescence. Fluorescence of the probe in the blue channel (top right) can be seen around the periphery of the tumor (upper arrows) but is also clearly visible in "healthy" dermis on the opposite side of the cartilage (lower arrow).

Figure 43:
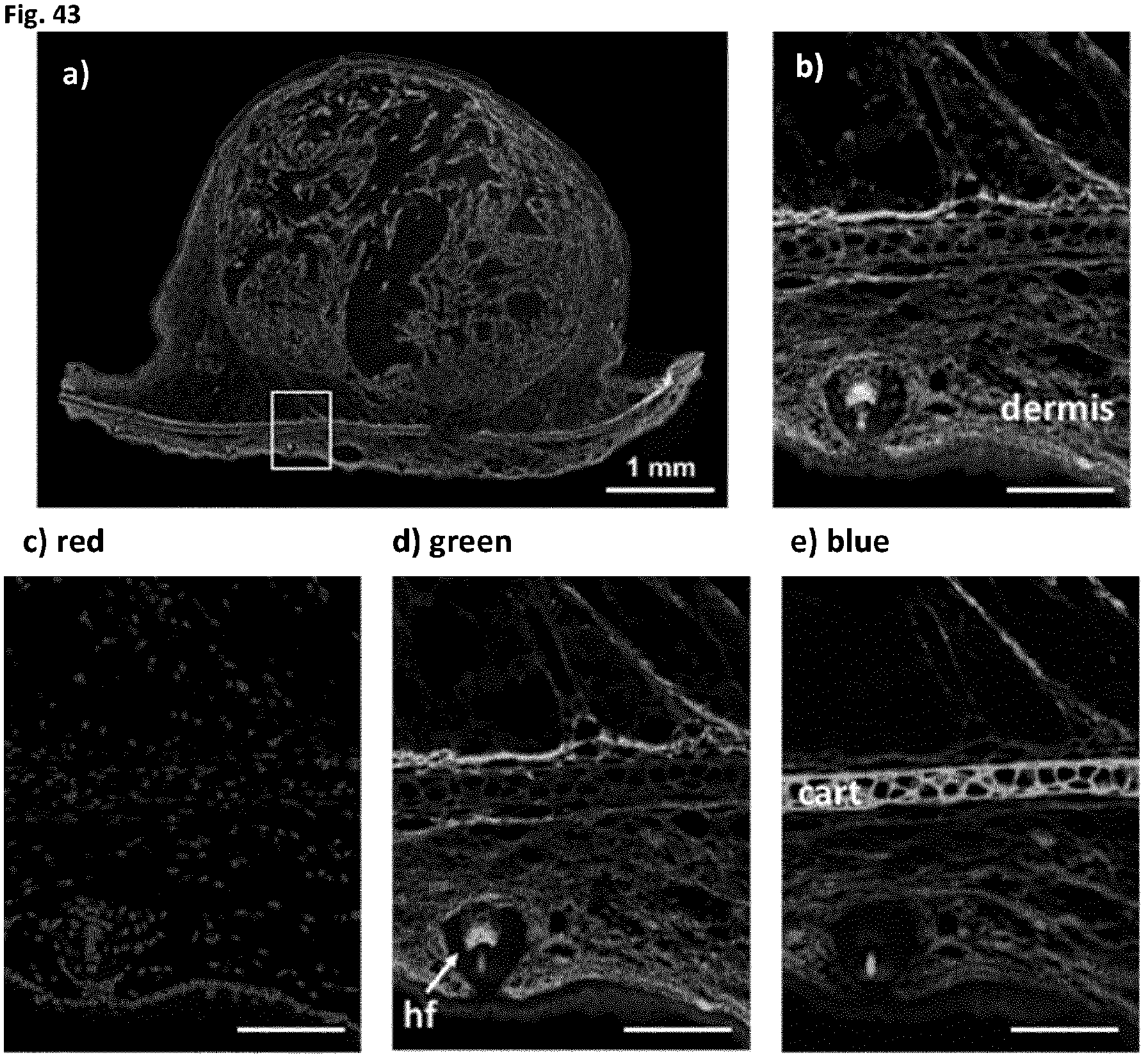

FIG. 43(*a*), FIG. 43(*b*), FIG. 43(*c*), FIG. 43(*d*), and FIG. 43(*e*) show the merged 20× image of an SSC13 ear tumor following staining with Compound 6 (FIG. 43(*a*) and FIG. 43(*b*)), and single channel images (FIG. 43(*c*) to FIG. 43(*e*)). Nuclei staining with propidium iodide (FIG. 43(*c*),red), immunostaining for collagen I (FIG. 43(*d*), green), and blue fluorescence (FIG. 43(*e*)) from Compound 6 can seen in the fibrotic tissue near the side of attachment to the cartilage, but is also abundant in the dermis outside of the tumor on the opposite side of the cartilage. Cartilage (cart) fluorescence and hair follicles (hf) can also be observed. 20× scale bar=100 μm.

Figure 44:
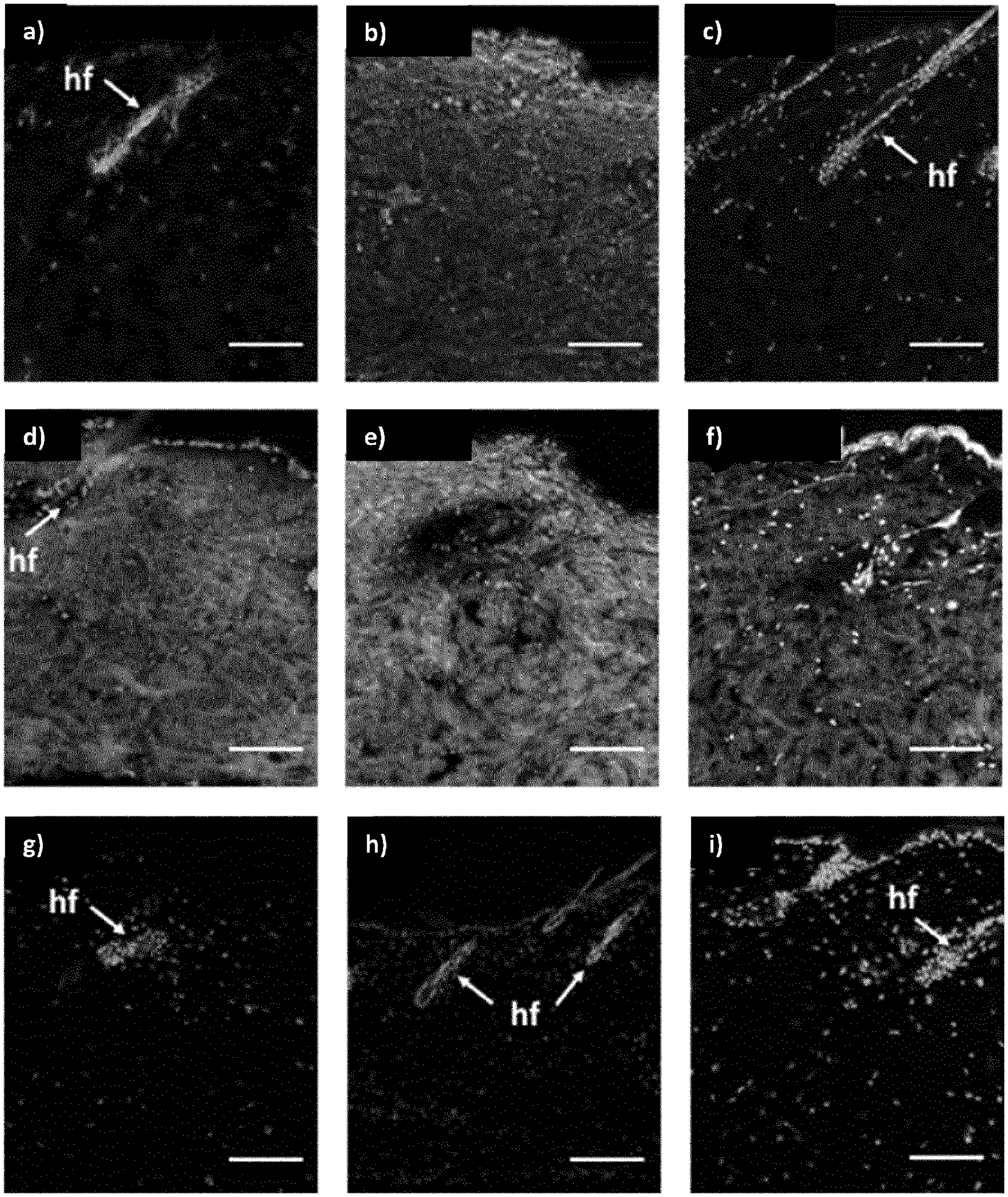

FIG. 44(*a*), FIG. 44(*b*), FIG. 44(*c*), FIG. 44(*d*), FIG. 44(*e*), FIG. 44(*f*), FIG. 44(*g*), FIG. 44(*h*), FIG. 44(*i*) show 10× images of healthy skin following staining with Compounds 3 (FIG. 44(*a*) to FIG. 44(*c*)), 6 (FIG. 44(*d*) to FIG. 44(*f*)), 4 (FIG. 44(*g*)), and 5 (FIG. 44(*h*)) and PBS (FIG. 44(*i*)). Nuclei staining with propidium iodide (red), immunostaining for collagen I (FIG. 44(*b*) and FIG. 44(*e*), green), or collagen III (FIG. 44(*c*) and FIG. 44(*f*), green), and blue fluorescence from Compound 6 can be seen throughout the dermis. Autofluorescence of the hair follicles (hf) can also be observed. 10× scale bar=100 μm.

DETAILED DESCRIPTION OF THE INVENTION

Example 1: General Experimental Aspects

Materials and reagents were of highest commercially available grade and used without further purification. They were purchased from Acros Organics (Switzerland), Sigma Aldrich (Switzerland), Fischer (Switzerland), Bachem (Switzerland), Chem-Impex (USA), and TCI (Germany). Water used for peptide preparation and purification was nanopure with resistivity of 18.2 MΩ*cm, prepared by a Sartorius Arium611VF (Switzerland) water purification system or bi-distilled, water was purchased from AppliChem Panreac (Switzerland). For small molecule synthesis, reactions were monitored by thin layer chromatography using Merck Millipore (Switzerland) silica gel 60 F254 glass-backed plates. Visualization of compounds was achieved by UV-Vis or via staining with $KMnO_4$. Flash chromatography and plug filtrations were performed using silica gel (60 Å pore size, and 230-400 mesh particle size, Sigma Aldrich (Switzerland)). Solvents for extraction and chromatography were of technical quality and distilled before usage. $^1H$ and $^{13}C$ NMR spectra were recorded on a Bruker DRX 400, a Bruker AV III 400 (400 MHz/100 MHz), or a Bruker AV III 600 (600 MHz/150 MHz). All spectra were recorded at 25° C., unless stated otherwise. Chemical shifts (δ) are reported in parts per million (ppm) relative to the signal of tetramethylsilane (TMS) or residual solvent. The signals were assigned with COSY, HSQC, HMBC, and NOESY spectra. Solid phase peptide synthesis (SPPS) was performed on Rink amide ChemMatrix resin from Biotage (Sweden), and automated peptide synthesis on a Syro I peptide synthesizer (MultiSynTech GmbH, Witten Germany). High-resolution mass spectrometry (HRMS) was performed by the Molecular and Biomolecular Analysis (MoBiAs) service of the D-CHAB at ETH Zurich using a Bruker Daltons maXis equipped with an ESI (electrospray ionization) source and a Q-TOF ion analyzer, or a Bruker Daltonics SOLARIX equipped with a MALDI (matrix-assisted laser desorption/ionization)/ESI source and a Q-TOF ion analyzer. α-Cyano-4-hydroxycinnamic acid (CHCA) was used as MALDI-MS matrix. Analytical reversed-phase high-performance liquid chromatography (RP HPLC) was performed on a Dionex UHPLC, Ultimate 3000 (Thermo Fisher Scientific, Waltham/USA). Preparative RP HPLC purification were carried out on a Dionex UHPLC, Ultimate 3000 (Thermo Fisher Scientific, Waltham/USA). Circular dichroism (CD) spectra were recorded on a Chirascan plus spectrometer (Applied Photophysics Ltd, Leatherhead/UK) with a Nitropack nitrogen generator (Parker Balston, Haverhill/USA) and a temperature controller TC 125 (Quantum Northwest). The solutions were measured in a quartz cell with a path length of 1.0 mm (Hellma 110-QS). Peptides were dried by lyophilization on a Christ Alpha 2-4 LD plus (Kuhnner A G, Birsfelden/CH) lyophilizer. Absorption and emission spectroscopy. UV-visible spectra were obtained with a Cary-500 Scan spectrophotometer. The spectra were measured in quartz cuvettes (ThorLabs, CV10Q3500, Newton, NJ USA). Samples were irradiated with an LED transilluminator (Roithner Lasertechnik, LED405-06V, Vienna, Austria) emitting at a wavelength as stated with an incident intensity of ca. 2 mW cm$^{-2}$, measured with a power-meter (ThorLabs, PM100D, Newton, NJ USA) equipped with a Si photodiode detector (ThorLabs, S120VC, Newton, NJ USA). Fluorescence spectroscopy was measured in a Fluorolog 3 fluorimeter (Horiba Jobin-Yvon, Germany) fluorimeter with a cuvette sample changer for quartz cuvettes (ThorLabs, CV10Q3500F-E, Newton, NJ USA). All measurements were conducted at 25° C. in 50 mM PBS pH 7.4 buffer solution under red light for ambient illumination to avoid photoactivation. Quantum yields were determined in PBS and as applicable correlated with known reference for Pacific Blue ($\Phi_F$=0.884 meas. versus $\Phi_F$=0.89). Ex vivo Fluorescence measurements were taken using a Tecan Spark 10M Multi-Mode Microplate Reader (Tecan, Mannedorf, Switzerland) at ambient temperature with a filter for excitation/emission (e.g. 405/460 nm respectively) unless stated otherwise, and values are expressed in relative fluorescent units (RFUs) for each experiment. All experiments were performed in triplicate. Graphical presentation and statistical analysis were performed using Graphpad Prism 7 software, (GraphPad Software, Inc., San Diego, USA.) with statistical significance determined as $p<0.05$ by ordinary one-way ANOVA with multiple comparisons.

Figure 1:
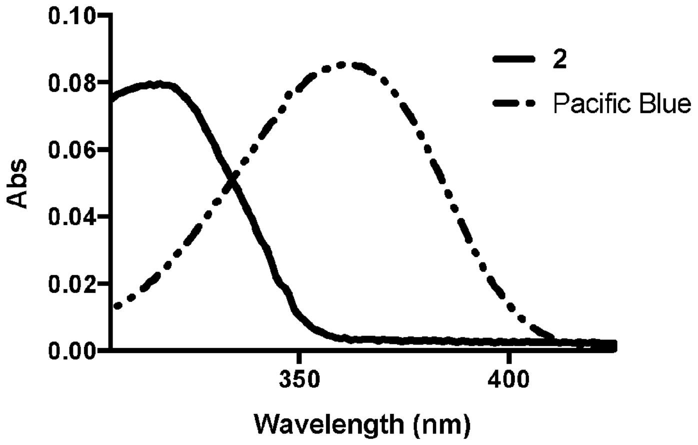
FIG. 1 shows the absorbance scan (excitation) of Compound 2 and 3-Acetoxy-6,8-difluoro-7-hydroxycumarin (Pacific Blue).
Figure 2:
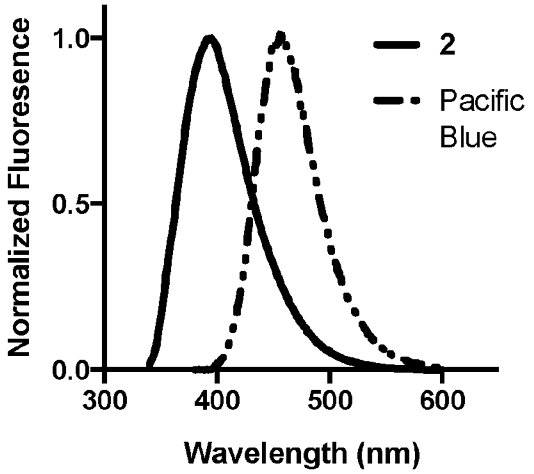
FIG. 2 shows the fluorescent emission scans of Compound 2 and 3-Acetoxy-6,8-difluoro-7-hydroxycumarin (Pacific Blue). Samples were excited at their respective absorbance maximum (Compound 2 at 313 nm, and Pacific Blue at 360 nm) and the emission is monitored from 333 nm or 380 nm to 600 nm.
Figure 3:
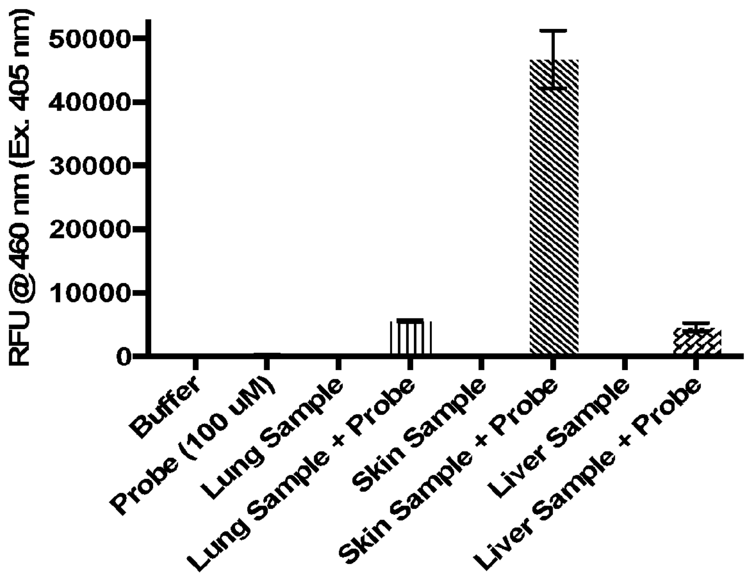
FIG. 3 shows the fluorescent signal obtained from Compound 2 treated with mouse tissue homogenate of isolated lung, skin, and liver samples. Fluorescent signals generated by 100 μM of Compound 2 during an 18 h incubation at 37° C. with tissue homogenates are shown as relative fluorescence units (RFU) when excited at 405 nm and measured at 460 nm (Ex/Em respectively). Background controls for buffer, untreated Compound 2 at 100 μM, and untreated homogenate samples are measured concurrently with treated samples (100 μM of Compound 2). The most significant increase in fluorescent signal was obtained for skin tissue type ($p<0.0001$, one-way ANOVA). Error bars represent SD, $n\geq3$.
Figure 4A:
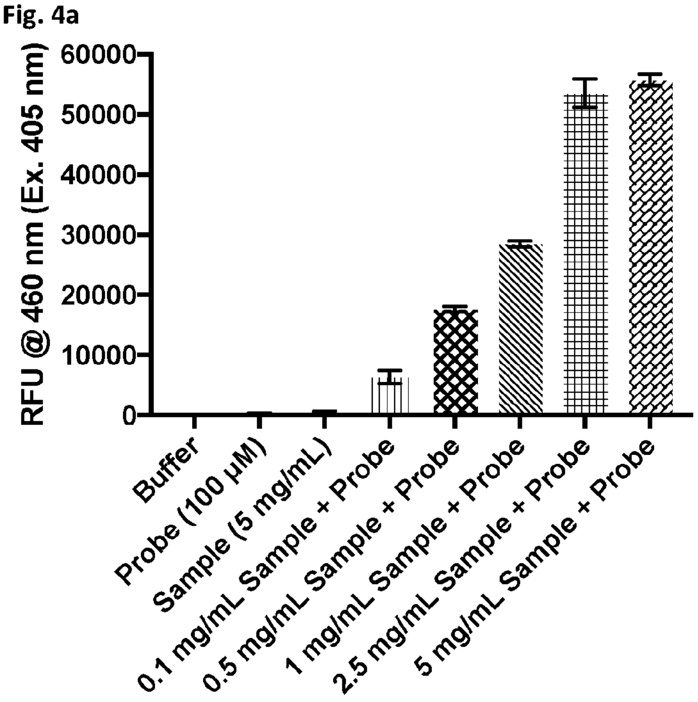
FIG. 4*a* shows the fluorescent signals obtained from a masked fluorescent probe cleaved by an amine oxidase according to Example 2.
Figure 4B:
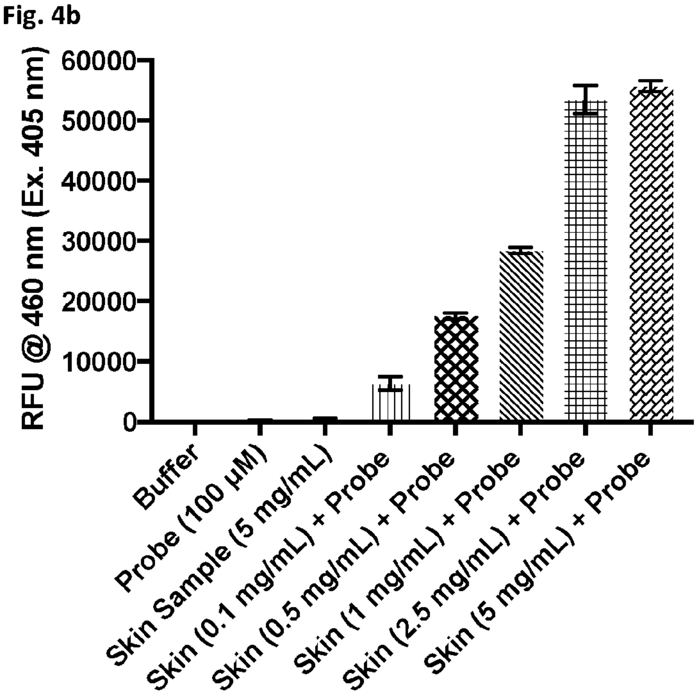
FIG. 4*b* shows the fluorescent signal obtained from Compound 2 treated with mouse tissue homogenate of isolated skin. Signals generated by Compound 2 at 100 μM during a 1 h incubation at 37° C. with tissue homogenate are shown as relative fluorescence units (RFU) when excited at 405 nm and measured at 460 nm (Ex/Em respectively). Background controls for buffer, untreated Compound 2 at 100 μM, and untreated homogenate samples are measured concurrently with all samples treated with 100 μM of Compound 2. Error bars represent SD, $n\geq3$.
Figure 4:
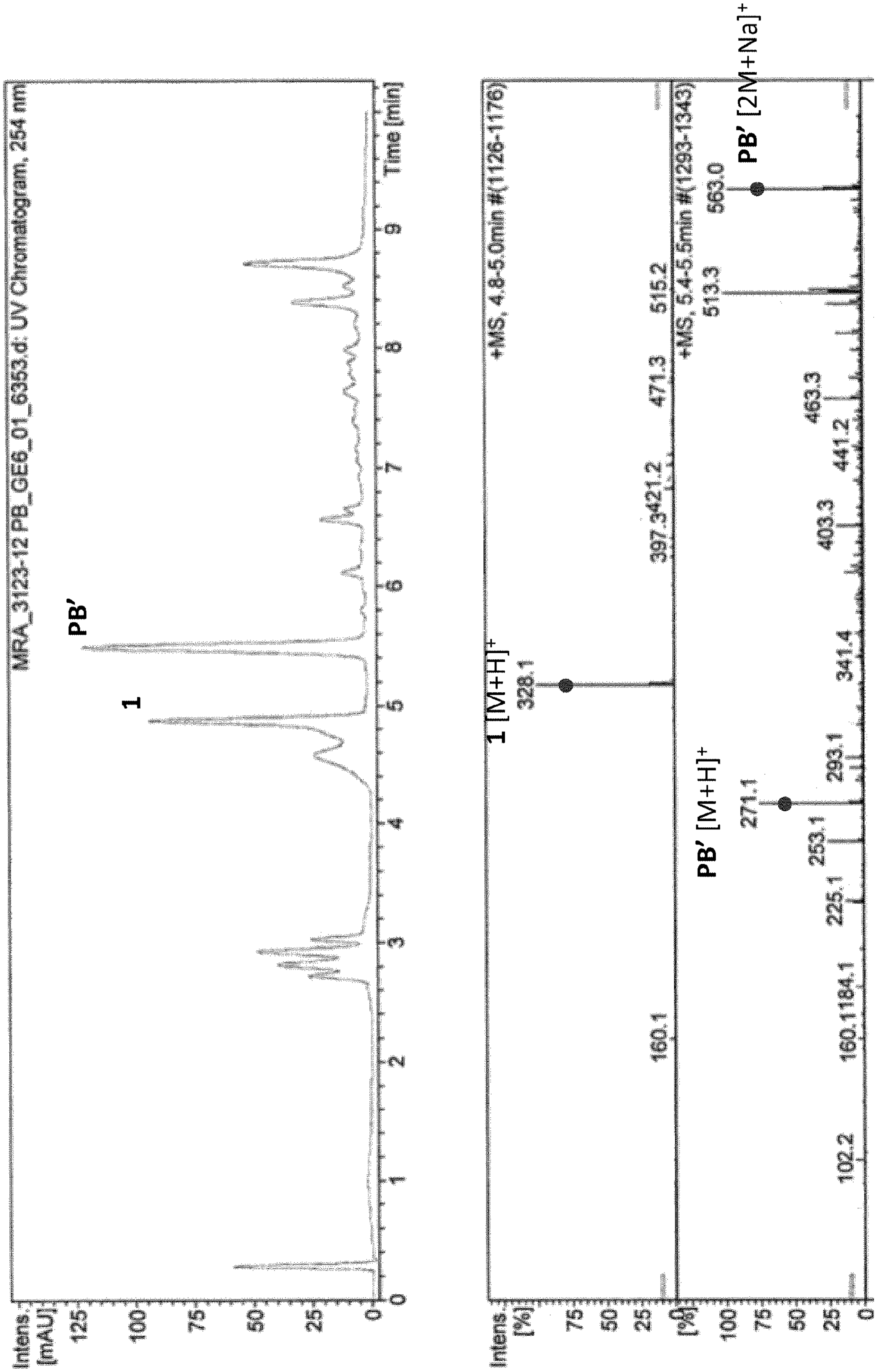
FIG. 4(*c*) shows the HPLC-MS trace showing the enzymatic conversion of Compound 1 to PB and loss of propylamine ($C_3H_7N$, [M]=57) via acrolein elimination after 18 h incubation using UV detection at 254 nm. Reverse phase HPLC, gradient 10%-90% $CH_3CN$ in $H_2O$ containing 1% $CH_3CN$ and 0.1% TFA over 10 min, (1) $t_R$=4.9 min and $[M+H]^+$=328.1; (PB) $t_R$=5.4 min, and $[M+H]^+$=271.1 and $[2M+Na]^+$=563.0.
Figure 5:
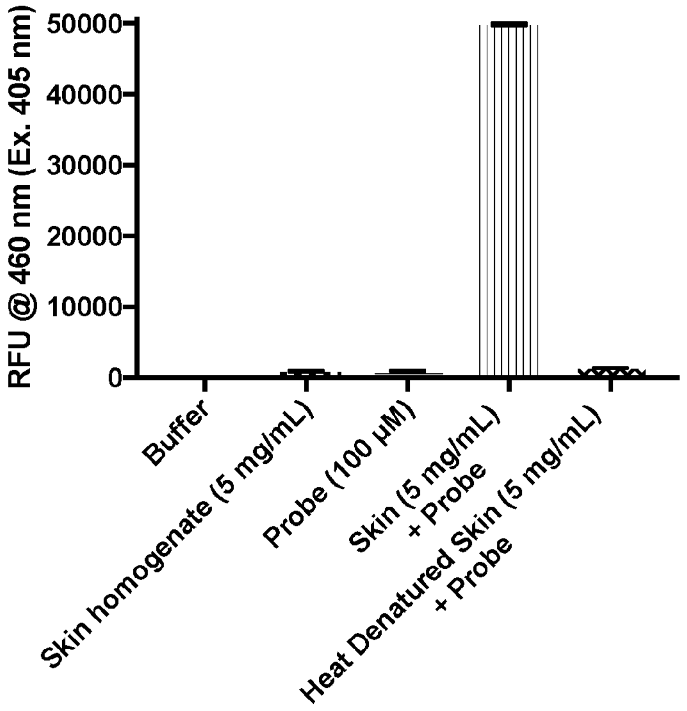
FIG. 5 shows the fluorescent signal obtained from Compound 2 treated with mouse tissue homogenate of isolated skin with and without heat denaturation (1.5 h at 90° C.). Fluorescent signals generated by Compound 2 at 100 μM during a 1 h incubation at 37° C. with tissue homogenate after treatment are shown as relative fluorescence units (RFU) when excited at 405 nm and measured at 460 nm (Ex/Em respectively). Background controls for buffer, untreated Compound 2 at 100 μM, and untreated samples are measured concurrently with all treated samples. A significant decrease in fluorescent signal was obtained for Compound 2 when incubated with the heat-denatured homogenate ($p<0.0001$, one-way ANOVA). Error bars represent SD, $n\geq3$.
Figure 6:
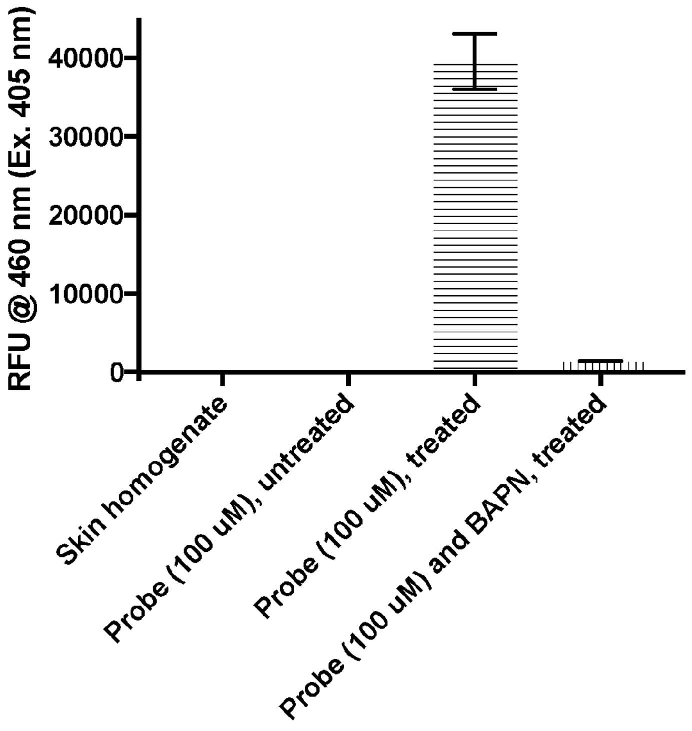
FIG. 6 shows the fluorescent signal obtained from Compound 2 treated with mouse tissue homogenate from isolated skin with and without the addition of a lysyl-oxidase inhibitor, BAPN. Skin homogenate was pretreated with 100 μM BAPN and incubated for 2 h at 37° C. prior to the addition of Compound 2. Fluorescent signals generated by 100 μM Compound 2 during a 1 h incubation at 37° C. with tissue homogenate after treatment are shown as relative fluorescence units (RFU) when excited at 405 nm and measured at 460 nm (Ex/Em respectively). All samples and controls are measured concurrently with all treated samples (Compound 2 at 100 μM). A significant decrease in fluorescent signal was obtained for Compound 2 when incubated with the BAPN-inhibited homogenate ($p<0.0001$, one-way ANOVA). Error bars represent SD, $n\geq3$.
Figure 7:
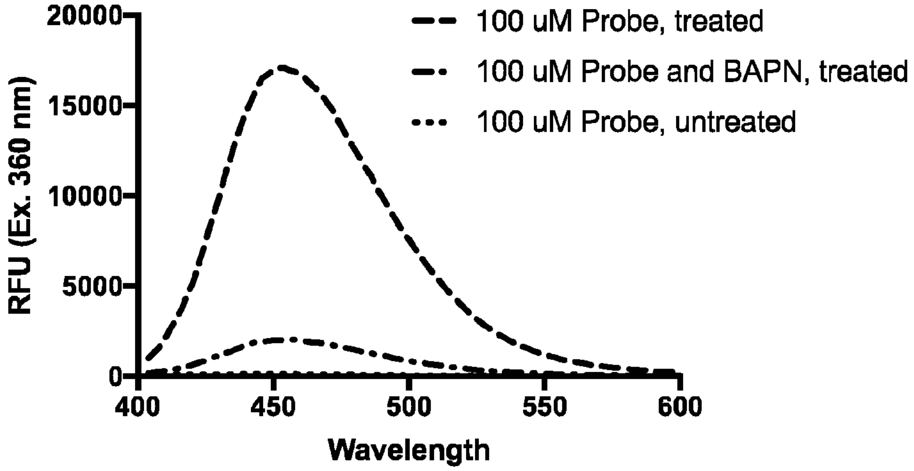
FIG. 7 shows the fluorescent emission scans of experiment from FIG. 6 obtained from Compound 2 alone, and from Compound 2 treated with mouse tissue homogenate of isolated skin with and without the addition of a lysyl-oxidase inhibitor, BAPN. Skin homogenate was pretreated with 100 μM BAPN and incubated for 2 h at 37° C. prior to the addition of Compound 2. Fluorescent signals generated by 100 μM Compound 2 during a 1 h incubation at 37° C. with tissue homogenate after treatment are shown as relative fluorescence units (RFU) when excited at 360 nm and measured from 400 to 600 nm (Ex/Em respectively). All samples and controls were measured concurrently with all treated samples. Traces represent average values of replicates (n=3).
Figure 8:
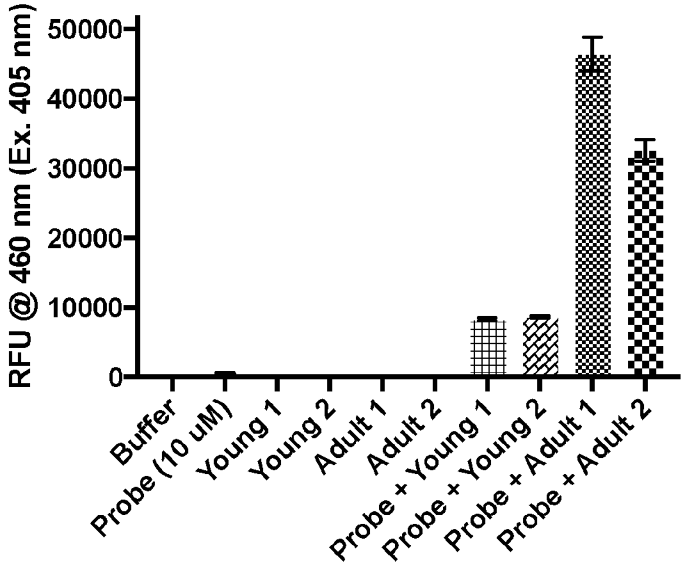
FIG. 8 shows the fluorescent signals obtained with mouse tissue homogenate of isolated skin from specimens representing two different age groups. Skin homogenates from 6 d and 9 wk mice were treated with Compound 2 at 10 μM and incubated for 18 h at 37° C. before measurements. Fluorescent signals generated are shown as relative fluorescence units (RFU) when excited at 405 nm and measured at 460 nm (Ex/Em respectively). All samples and controls are measured in concurrent assays as treated samples (10 μM Probe). Error bars represent SD, $n\geq3$.
Figure 9:
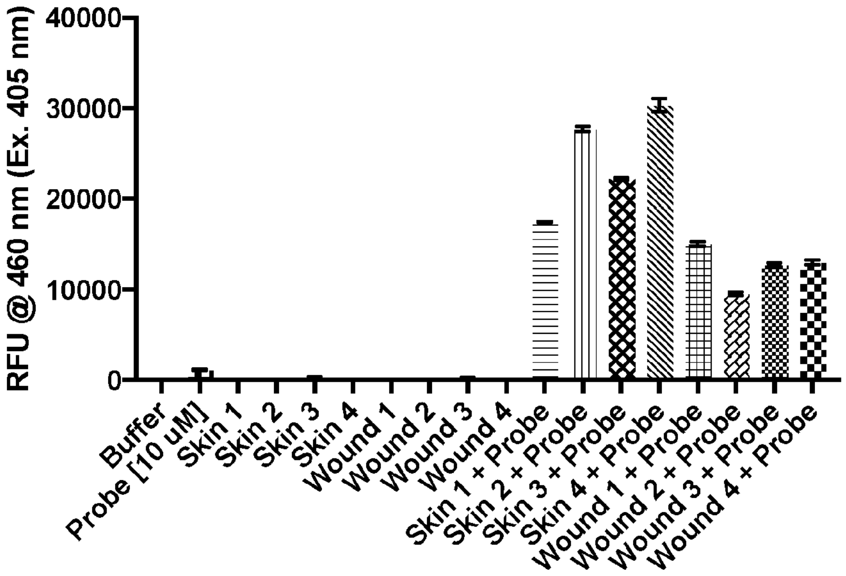
FIG. 9 shows the fluorescent signals obtained with mouse tissue homogenate of isolated skin of wounded or unwounded tissues. Wounds were created 5d prior to sample collection and activity assay. Skin homogenates were treated with Compound 2 at 10 μM and incubated for 18 h at 37° C. before measurements. Fluorescent signals generated are shown as relative fluorescence units (RFU) when excited at 405 nm and measured at 460 nm (Ex/Em respectively). All samples and controls are measured simultaneously with the treated samples (10 μM Compound 2). Error bars represent SD, $n\geq3$.
Figure 10:
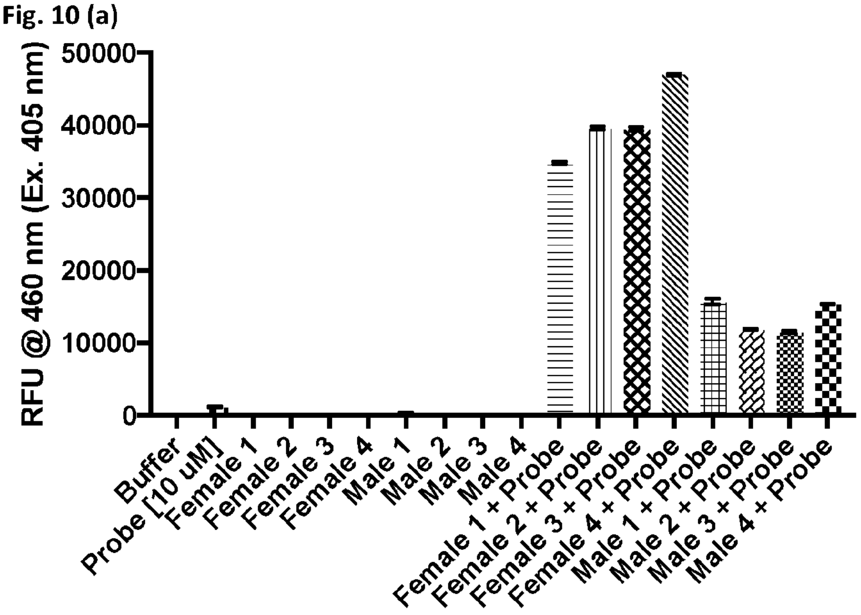
FIG. 10 (*a*) shows the fluorescent signals obtained with tissue homogenate of isolated skin of male and female mice. Skin homogenates were treated with 10 μM of Compound 2 and incubated for 18 h at 37° C. before measurements. Fluorescent signals generated are shown as relative fluorescence units (RFU) when excited at 405 nm and measured at 460 nm (Ex/Em respectively). All samples and controls are measured in concurrent assays with the treated samples (10 μM Compound 2). Error bars represent SD, $n\geq3$.
Figure 10:
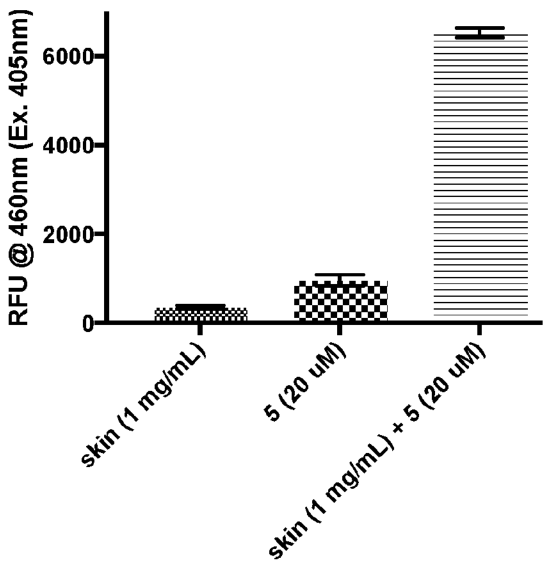
Figure 11:
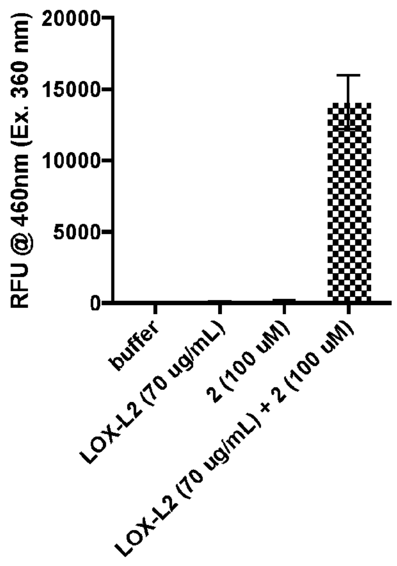
FIG. 11 shows the fluorescent signal obtained from Compound 2 treated with recombinant human lysyl oxidase-like 2 (LOX-L2). Fluorescent signals were measured after a 24 h incubation at 37° C. and normalized to background signals of empty wells. Values are shown as relative fluorescence units (RFU) when excited at 360 nm and measured at 460 nm (Ex/Em respectively). All samples including buffer, untreated Compound 2 at 100 μM, and LOX-L2 were treated and measured concurrently with treated samples (100 μM of Compound 2). Error bars represent SD, $n\geq3$.
Figure 12:
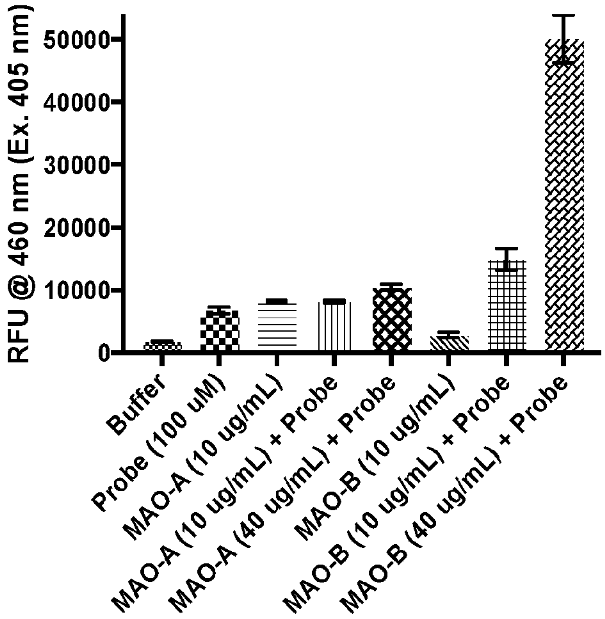
FIGS. 12 (*a*) and 12 (*b*) show the fluorescent signal obtained from Compound 2 treated with recombinant human monoamine oxidase A (MAO-A) and B (MAO-B). Fluorescent signal generated during a 2 h incubation at 37° C. is shown as relative fluorescence units (RFU) when excited at 405 nm and measured at 460 nm (Ex/Em respectively). Background controls for buffer, untreated Compound 2 at 100 μM, and MAO-A and MAO-B are measured simultaneously with treated samples (100 μM of Compound 2). A significant increase in fluorescent signal compared to controls after 2 h incubation was obtained for Compound 2 when incubated with MAO-B ($p<0.0001$, one-way ANOVA). Error bars represent SD, $n \geq 3$.
Figure 12:
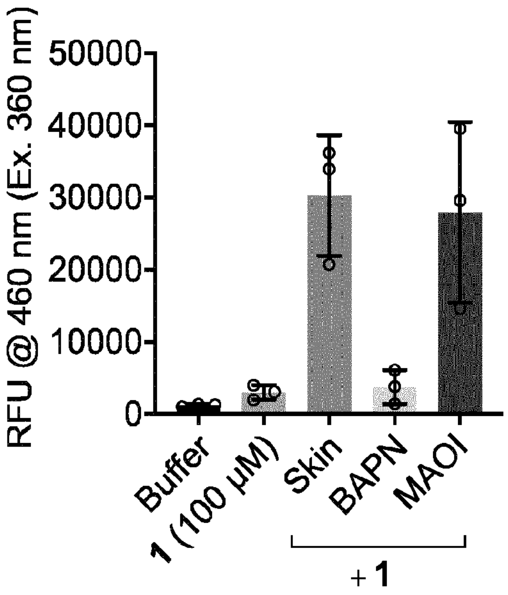

Example 2: General and Exemplary Experimental Protocol for Determining Amine-Oxidase Activity Fluorescence experiments for determining amine oxidase activity of a given enzyme are conducted using a fluorescence plate reader and a standard 96-well black polystyrene plate with a clear flat bottom. To the plate 150 μL of the following solutions are added to individual wells, e.g. with at least three replicates: buffer (e.g. 25 mM at pH 7.5), a solution in buffer of the amine-oxidase reactive probe, e.g. Compound 2, (e.g. at 100 μM), a buffered solution of the sample containing an amine-oxidase at the desired concentration(s) (e.g. 40 μg/mL), and a buffered solution of the sample containing amine-oxidases with addition of the probe, e.g. Compound 2, (e.g. at 100 μM). The plate is incubated in the dark at 37° C. for a period of time between 15 min and 24 hours before measurements are taken. Fluorescence is measured by exciting the unmasked probe at the absorbance maximum (e.g. 360 nm) or at 405 nm, and measuring the fluorescence at the emission maximum of the probe, for example at 460 nm. Enzyme activity is observed as fluorescence measured relative to the untreated controls, for example as expressed in relative fluorescent units (RFUs). The probe activation, and thus amine oxidase activity can be displayed in a diagram (see FIG. 4*a*). Any change, optionally any statistically relevant change, in fluorescence relative to the untreated controls is indicative of amine oxidase activity.

Example 3: Synthesis of 3-Carboxymethyl-6,8-difluoro-7-hydroxycoumarin ("Pacific Blue" Ester)

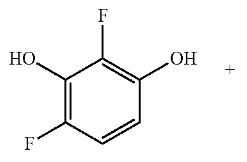

-continued

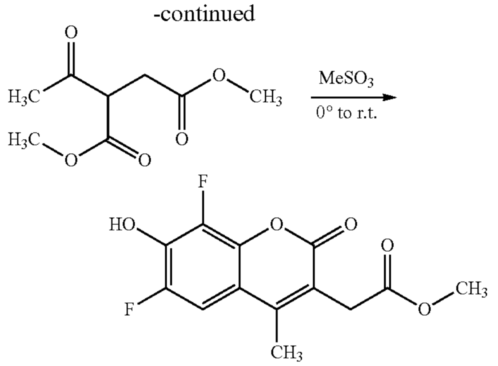

Pacific Blue (ester) was prepared as previously reported in Chang, D.; Kim, K. T.; Lindberg, E.; Winssinger, N., *Bioconj. Chem.* 2018, 29, 158-163 via Pechmann condensation of 2,4-difluororesorcinol with dimethyl acetylsuccinate. $^1$H NMR (400 MHz, DMF-$d_7$) δ 7.61 (dd, J=11.8, 2.2 Hz, 1H), 3.79 (s, 2H), 3.71 (s, 3H), 2.48 (s, 3H).

Example 3a: Synthesis of 3-Carboxymethyl-6,8-dichloro-7-hydroxycoumarin

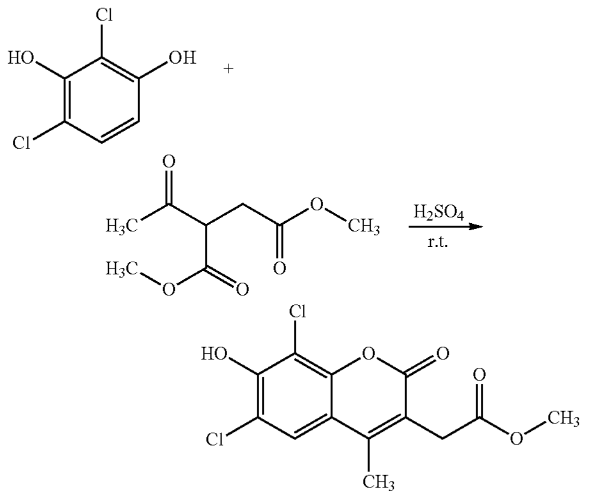

2,4-dichlororesorcinol (1.68 g, 9.4 mmol) was dissolved in dimethyl acetylsuccinate (1.77 g, 9.5 mmol) by trituration. Concentrated $H_2SO_4$ (1.5 mL) was added, and the solution was stirred at r.t. for 24 h. The resulting viscous liquid was homogenized with the addition of methanol (1-2 mL) and then poured over crushed ice (100 mL). The precipitate was collected by filtration, and recrystallized from methanol/water to yield 3-carboxymethyl-6,8-dichloro-7-hydroxycoumarin as a purple crystalline solid. $^1$H NMR (400 MHz, $CD_3CN$) δ 7.71 (s, 1H), 3.66 (s, 5H), 2.35 (s, 3H). $^{13}$C NMR (101 MHz, $CD_3CN$) δ 171.54, 161.19, 152.23, 149.77, 149.10, 125.08, 118.93, 115.46, 109.76, 52.75, 33.51, 15.88. HRMS (ESI): m/z calcd. for $C_{13}H_{10}Cl_2NaO_5$: 338.9797 [M+Na]$^+$; found: 338.9795.

Example 4: 3-methylacetate-6,8-difluoro-7-(4-((tert-butoxycarbonyl)amino)propoxy)-coumarin

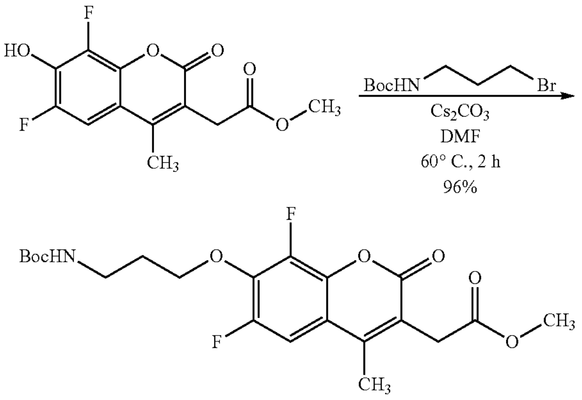

Pacific Blue (5.4 mmol, 1.56 g) and 3-(tert-butoxycarbonylamino)-propyl bromide (11 mmol, 2.6 g) were dissolved in 18 mL of anhydrous DMF. $C_5CO_3$ (8.1 mmol, 2.64 g) was added, and the resulting solution was heated to 60° C. for 2 hours. The solution was cooled to room temperature, and the reaction was quenched with 200 mL of an aqueous ammonium chloride solution, extracted with EtOAc (3×50 mL), dried over $Na_2SO_4$(s), and concentrated under reduced pressure. The crude mixture was purified by chromatography on silica gel (1-5% gradient of MeOH in dichloromethane), and concentrated under reduced pressure to produce 3-methylacetate-6,8-difluoro-7-(4-((tert-butoxycarbonyl)amino)propoxy)-coumarin ("Boc-PB-LOX-OMe") as a clear oil (2.3 g, 96%). $^1$H NMR (400 MHz, $CD_3CN$) δ 7.27 (dd, J=12.0, 2.2 Hz, 1H), 5.38 (s, 1H), 4.25 (t, J=6.2 Hz, 2H), 3.60 (s, 5H), 3.16 (q, J=6.6 Hz, 2H), 2.26 (s, 3H), 1.84 (p, J=6.4 Hz, 2H), 1.32 (s, 9H). $^{13}$C NMR (101 MHz, $CD_3CN$) δ 171.31, 160.66, 156.92, 152.40 (dd, J=243.1, 4.6 Hz), 149.54 (t, J=2.8 Hz), 143.70 (dd, J=249.3, 6.3 Hz), 139.43 (dd, J=10.3, 2.5 Hz), 138.78 (dd, J=16.0, 10.9 Hz), 120.63 (d, J=0.8 Hz), 116.21 (dd, J=9.2, 1.3 Hz), 107.68 (dd, J=22.9, 3.6 Hz), 79.12, 73.76, 52.76, 37.83, 33.62, 31.21, 28.60, 15.96. $^{19}$F NMR, F-H decoupled (377 MHz, $CD_3CN$) δ −133.72 (d, J=5.4 Hz), −150.18 (d, J=5.4 Hz). $^{19}$F NMR (377 MHz, $CD_3CN$) δ −133.72 (dd, J=11.9, 5.4 Hz), −150.18 (d, J=5.4 Hz). HRMS (ESI): m/z calcd. for $C_{21}H_{25}F_2NNaO_7$: 464.1491 [M+Na]$^+$; found: 464.1494.

Example 4a: Synthesis of 3-methylacetate-6,8-dichloro-7-(4-((tert-butoxycarbonyl)amino)propoxy)-coumarin

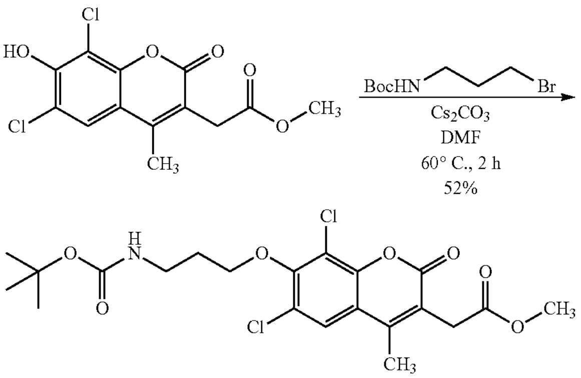

3-Carboxymethyl-6,8-dichloro-7-hydroxycoumarin (0.71 mmol, 227 mg) and 3-(tert-butoxycarbonylamino)-propyl bromide (1.45 mmol, 347 mg) were dissolved in 2.4 mL of anhydrous DMF. $C_sCO_3$ (1.07 mmol, 349 mg) was added, and the resulting solution was stirred and heated to 60° C. for 2 hours. The solution was cooled to room temperature, and the reaction was quenched with 100 mL of an aqueous ammonium chloride solution, extracted with EtOAc (3×50 mL), dried over $Na_2SO_4$(s), and concentrated under reduced pressure. The crude mixture was purified by chromatography on silica gel (1-5% gradient of MeOH in dichloromethane), and concentrated under reduced pressure to produce 3-methylacetate-6,8-dichloro-7-(4-((tert-butoxycarbonyl)amino)propoxy)-coumarin as a white solid (175 mg, 52%). $^1$H NMR (400 MHz, $CD_3CN$) δ 7.70 (s, 1H), 5.44 (s, 1H), 4.09 (t, J=6.2 Hz, 2H), 3.66 (s, 2H), 3.66 (s, 3H), 3.28 (q, J=6.6 Hz, 2H), 2.34 (s, 3H), 2.01-1.94 (m, 2H), 1.40 (s, 9H). $^{13}$C NMR (101 MHz, $CD_3CN$) δ 171.27, 160.85, 156.93, 154.33, 149.34, 148.90, 125.42, 125.26, 120.79, 118.99, 117.72, 73.13, 52.78, 38.20, 33.62, 33.50, 31.19, 28.63, 15.99. HRMS (ESI): m/z calcd. for $C_{21}H_{25}Cl_2NNaO_7$: 496.0900 [M+Na]$^+$; found: 496.0901.

Example 4b: Synthesis of 3-methylacetate-6,8-dichloro-7-(4-ammoniumpropoxy)-coumarin Chloride

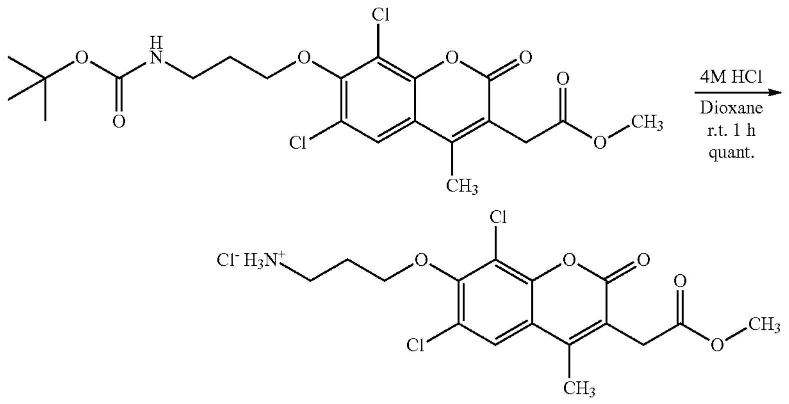

3-methylacetate-6,8-dichloro-7-(4-((tert-butoxycarbonyl) amino)propoxy)-coumarin (0.042 mmol, 20 mg) was dissolved in 250 μL of 4N HCl in dioxane at ambient temperature and stirred for 1 hour. Solvent was then removed from the resulting slurry by evaporation with a gentle stream of compressed air, and the white solid was dried overnight under high vacuum to produce the HCl salt 3-methylacetate-6,8-dichloro-7-(4-ammoniumpropoxy)-coumarin chloride as a white solid (17 mg, quant.). $^{1}$H NMR (400 MHz, Deuterium Oxide) δ 7.77 (s, 1H), 4.26 (t, J=5.7 Hz, 2H), 3.81 (s, 2H), 3.77 (s, 3H), 3.39 (t, J=7.5 Hz, 2H), 2.39 (s, 3H), 2.26 (dt, J=12.7, 6.1 Hz, 2H). $^{13}$C NMR (126 MHz, $D_2O$) δ 173.01, 162.07, 152.47, 151.06, 146.91, 124.69, 124.52, 118.74, 117.94, 116.36, 71.80, 52.88, 37.41, 32.71, 27.32, 15.10.

Example 5: 3-carboxy-6,8-difluoro-7-(4-((tert-butoxycarbonyl)amino)propoxy)-coumarin (Compound 1)

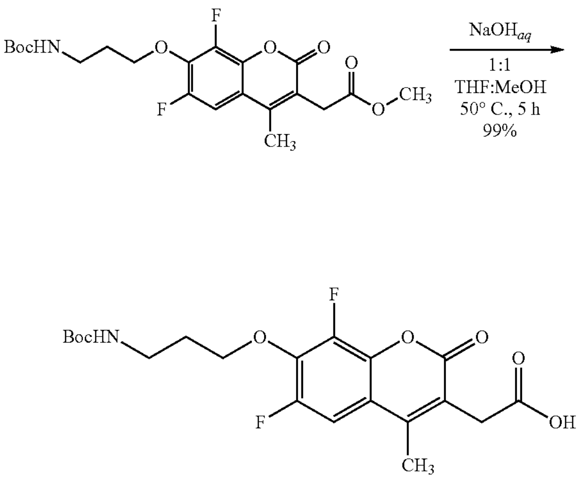

Boc-PB-LOX-OMe (5.2 mmol, 2.3 g) was dissolved in 8 mL of 1:1 THF:MeOH, and NaOH (15.6 mmol, 624 mg) was added as an aqueous solution in 1 mL of $H_2O$, and the resulting solution was heated to 50° C. for 5 hours. Upon completion as observed by thin layer chromatography, ($R_f$=0.1 for 5% MeOH in DCM), the solution was cooled to room temperature, and the reaction was carefully acidified to pH 2 with 1M HCl, and immediately extracted with EtOAc (3×50 mL), dried over $Na_2SO_4$(s), and concentrated under reduced pressure to give Compound 1 as a white solid (2.2 g, 99%). $^{1}$H NMR (400 MHz, DMSO-$d_6$) δ 12.53 (s, 1H), 7.66 (d, J=12.5 Hz, 1H), 6.89 (t, J=5.7 Hz, 1H), 4.29 (t, J=6.3 Hz, 2H), 3.63 (s, 2H), 3.11 (q, J=6.5 Hz, 2H), 2.38 (s, 3H), 1.84 (p, J=6.6 Hz, 2H), 1.37 (s, 9H). $^{13}$C NMR (101 MHz, DMSO) δ 171.06, 159.32, 155.61, 152.13, 152.08, 149.71, 149.67, 148.34, 143.36, 143.29, 140.88, 140.82, 137.90, 137.88, 137.80, 137.78, 137.32, 137.21, 137.16, 137.05, 119.92, 115.16, 115.07, 107.40, 107.18, 77.53, 72.55, 36.41, 32.94, 29.97, 28.21, 15.39. $^{19}$F NMR, F-H decoupled (376 MHz, DMSO-$d_6$) δ −132.45 (d, J=5.0 Hz), −149.31 (d, J=5.1 Hz). $^{19}$F NMR (376 MHz, DMSO-$d_6$) δ −132.45 (dd, J=11.9, 4.9 Hz), −149.31 (d, J=4.7 Hz). HRMS (ESI): m/z calcd. for $C_{20}H_{23}F_2NNaO_7$: 450.1335 $[M+Na]^+$; found: 450.1340.

Example 5a: Synthesis of MRA_3102

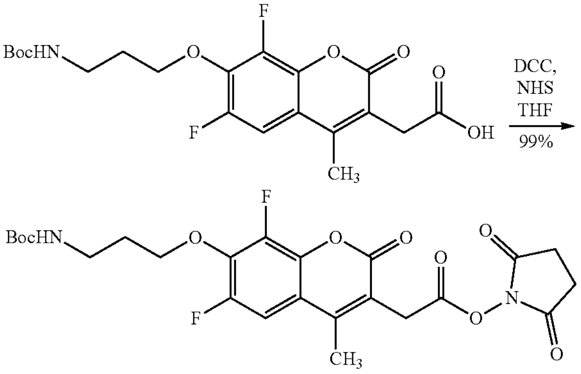

MRA_3102. 2 (0.68 mmol, 300 mg) was dissolved in 3.4 mL of THF, and N-hydroxysuccinimide (0.68 mmol, 78 mg) was added. The resulting solution was cooled in an ice batch, and DCC was added (0.68 mmol, 140.2 mg). The reaction mixture was stirred on ice for 30 minutes, and then allowed to come warm to ambient temperature overnight. DCU was filtered, and the solution was concentrated by rotary evaporation. The crude residue was resuspended in EtOAc, and filtered, and again concentrated by rotary evaporation, and this process was repeated 2× until no more precipitate could be observed in solution. The crude NHS-ester was then concentrated under reduced pressure to produce MRA_3102 as a white solid (353 mg, 99%). $^{1}$H NMR (400 MHz, $CDCl_3$) δ 7.17 (dd, J=11.2, 2.2 Hz, 1H), 4.80 (s, 1H), 4.35 (t, J=6.0 Hz, 2H), 4.08 (s, 2H), 3.36 (q, J=6.2 Hz, 2H), 2.83 (s, 4H), 2.41 (s, 3H), 2.00 (p, J=6.4 Hz, 2H), 1.44 (s, 9H). $^{13}$C NMR (101 MHz, $CDCl_3$) δ 168.81, 165.57, 159.57, 156.18, 151.73 (dd, J=246.0, 4.2 Hz), 149.64 (t, J=2.7 Hz), 143.15 (dd, J=253.2, 5.7 Hz), 138.97 (dd, J=10.3, 2.6 Hz), 138.70 (dd, J=15.6, 10.7 Hz), 119.85 (d, J=13.4 Hz), 117.63, 114.98 (d, J=8.8 Hz), 106.25 (dd, J=22.4, 3.7 Hz), 77.36, 73.09, 37.66, 30.41, 30.08, 28.52, 25.70, 16.06. $^{19}$F NMR, F-H decoupled (376 MHz, $CDCl_3$) δ −131.48 (d, J=5.8 Hz), −146.94 (d, J=5.8 Hz). $^{19}$F NMR (376 MHz, $CDCl_3$) δ −131.48 (dd, J=10.4, 5.5 Hz), −146.94 (d, J=4.8 Hz).

Example 6: 3-carboxy-6,8-difluoro-7-(4-((tert-butoxycarbonyl)amino)propoxy)-coumarin (Compound 2)

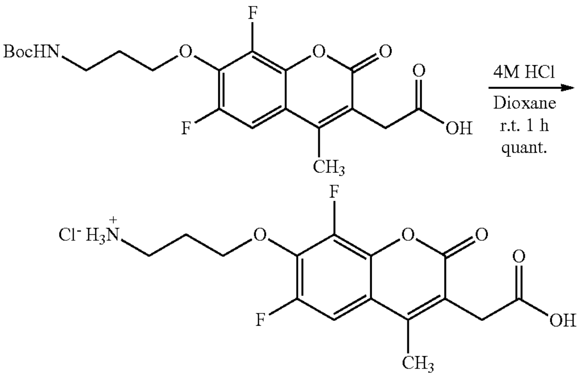

Compound 1 (0.047 mmol, 20 mg) was dissolved in 250 µL of 4N HCl in dioxane at ambient temperature and stirred for 1 hour. Solvent was then removed from the resulting slurry by evaporation with a gentle stream of compressed air, and the white solid was dried overnight under high vacuum to produce the HCl salt of Compound 2 as a white solid (17 mg, quant.). $^{1}$H NMR (400 MHz, DMSO-$d_6$) δ 8.13 (s, 3H), 7.67 (dd, J=12.1, 2.1 Hz, 1H), 4.37 (t, J=6.1 Hz, 2H), 3.62 (s, 2H), 2.97 (t, J=7.5 Hz, 2H), 2.36 (s, 3H), 2.05 (p, J=6.4 Hz, 2H). $^{13}$C NMR (101 MHz, DMSO-$d_6$) δ 171.14, 159.38, 150.92 (dd, J=242.9, 4.2 Hz), 148.43 (t, J=2.5 Hz), 142.14 (dd, J=249.1, 6.2 Hz), 137.87 (dd, J=10.1, 2.3 Hz), 136.95 (dd, J=16.3, 11.0 Hz), 120.14, 115.41 (d, J=9.3 Hz), 107.44 (dd, J=22.5, 3.4 Hz), 71.92, 66.43, 35.84, 33.06, 27.65, 15.51. $^{19}$F NMR, F-H decoupled (376 MHz, DMSO-$d_6$) δ −132.51 (d, J=4.9 Hz), −149.30 (d, J=4.9 Hz). $^{19}$F NMR (376 MHz, DMSO-$d_6$) δ −132.51 (dd, J=12.0, 4.9 Hz), −149.30 (d, J=5.1 Hz). HRMS (ESI): m/z calcd. for $C_{15}H_{16}F_2NO_5$: 328.0991 [M+H]$^+$; found: 328.0989.

Example 7: 3-methylacetate-6,8-difluoro-7-(4-((tert-butoxycarbonyl)amino)butoxy)-coumarin (MRA 3068)

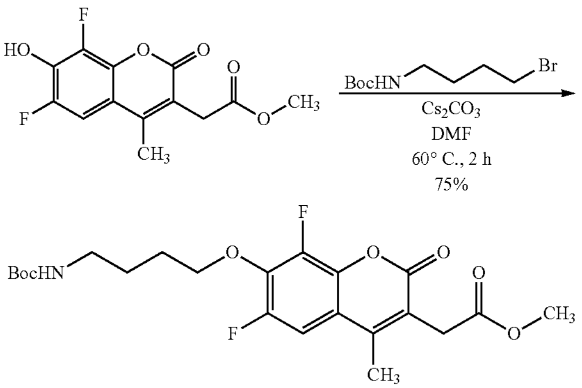

3-Carboxymethyl-6,8-difluoro-7-hydroxycoumarin (Pacific Blue) (1 mmol, 284 mg) and 3-(tert-butoxycarbonylamino)-butyl bromide (2 mmol, 504 mg) were dissolved in 2 mL of anhydrous DMF. $C_sCO_3$ (1.5 mmol, 489 mg) was added, and the resulting solution was heated to 60° C. for 2 hours. The solution was cooled to room temperature, and the reaction was quenched with 100 mL of an aqueous ammonium chloride solution, extracted with EtOAc (3×50 mL), dried over $Na_2SO_4$(s), and concentrated under reduced pressure. The crude mixture was purified by chromatography on silica gel (1-5% gradient of MeOH in dichloromethane), and concentrated under reduced pressure to produce MRA_3068 as a white solid (341 mg, 75%). $^{1}$H NMR (400 MHz, $CDCl_3$) δ 7.13 (dd, J=11.4, 2.3 Hz, 1H), 4.60 (s, 1H), 4.29 (tt, J=6.2, 1.0 Hz, 2H), 3.73 (s, 2H), 3.71 (s, 3H), 3.19 (s, 2H), 2.34 (s, 3H), 1.86-1.78 (m, 2H), 1.73-1.65 (m, 2H), 1.43 (s, 9H). $^{13}$C NMR (101 MHz, $CDCl_3$) δ 170.35, 160.05, 156.13, 151.71 (dd, J=245.5, 4.5 Hz), 148.03 (t, J=2.7 Hz), 143.14 (dd, J=253.0, 6.0 Hz), 138.76 (dd, J=10.5, 2.5 Hz), 138.33 (dd, J=15.7, 10.7 Hz), 119.76, 115.20 (dd, J=8.8, 1.0 Hz), 106.03 (dd, J=22.4, 3.7 Hz), 74.73 (t, J=3.5 Hz), 52.54, 33.01, 28.53, 27.34, 26.54, 15.81. $^{19}$F NMR, F-H decoupled (376 MHz, $CDCl_3$) δ −131.81 (d, J=5.6 Hz), −147.25 (d, J=5.8 Hz). $^{19}$F NMR (376 MHz, $CDCl_3$) δ −131.81 (dd, J=11.4, 5.7 Hz), −147.25 (dd, J=5.7, 2.0 Hz). HRMS (ESI): m/z calcd. for $C_{22}H_{31}F_2N_2O_7$: 473.2094 [M+NH$_4$]$^+$; found: 473.2087.

Example 8: 3-Carboxy-6,8-difluoro-7-(4-((tert-butoxycarbonyl)amino)butoxy)-coumarin (MRA_3069)

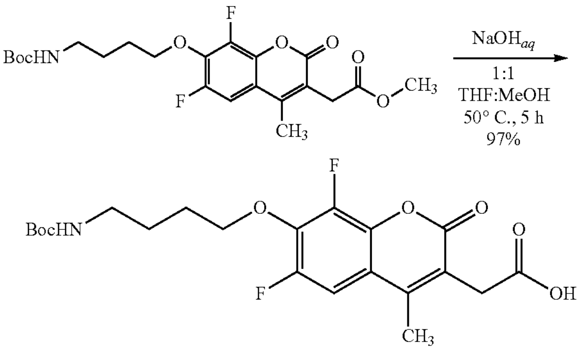

MRA_3068 (0.5 mmol, 241 mg) was dissolved in 1.3 mL of 1:1 THF:MeOH, and NaOH (1.6 mmol, 64 mg) was added as an aqueous solution in 0.6 mL of $H_2O$, and the resulting solution was heated to 50° C. for 5 hours. Upon consumption of starting material as observed by thin layer chromatography, ($R_f$=0.1 for 5% MeOH in DCM), the solution was cooled to room temperature, and the reaction was carefully acidified to pH 2 with 1M HCl, and immediately extracted with EtOAc (3×50 mL), dried over $Na_2SO_4$(s), and concentrated under reduced pressure to produce MRA_3069 as a clear oil (231 mg, 97%). $^{1}$H NMR (400 MHz, Methanol-$d_4$) δ 7.40 (dd, J=11.8, 2.2 Hz, 1H), 4.30 (t, J=6.2 Hz, 2H), 3.70 (s, 2H), 3.11 (t, J=6.8 Hz, 2H), 2.38 (s, 3H), 1.85-1.76 (m, 3H), 1.71-1.63 (m, 3H), 1.42 (s, 9H). $^{13}$C NMR (101 MHz, Methanol-$d_4$) δ 173.51, 161.70, 158.51, 153.00 (dd, J=244.3, 4.4 Hz), 150.12 (t, J=2.7 Hz), 144.08 (dd, J=250.5, 6.2 Hz), 139.63 (dd, J=10.3, 2.5 Hz), 139.28 (dd, J=16.0, 10.9 Hz), 121.06, 116.66 (d, J=9.1 Hz), 107.66 (dd, J=22.9, 3.6 Hz), 79.85, 75.86 (t, J=3.4 Hz), 40.86, 33.62, 28.77, 28.34, 27.25, 15.68. $^{19}$F NMR, F-H decoupled (376 MHz, Methanol-$d_4$) δ −133.41 (d, J=5.5 Hz), −150.56 (d, J=5.5 Hz). $^{19}$F NMR (377 MHz, Methanol-$d_4$) δ −133.41 (dd, J=11.8, 5.4 Hz), −150.55 (d, J=5.4 Hz). HRMS (ESI): m/z calcd. for $C_{21}H_{23}F_2NNaO_7$: 462.1346 [M+Na-2H]$^-$; found: 462.1356.

Example 9: Ex Vivo Experiments—General Aspects

Skin tissue used for enzymatic analysis of LOX activity was harvested (1 cm×1 cm) and placed in 2 ml of ice-cold PBS. Skin tissue was homogenized using an Ultra-TURRAX homogenizer (KA®-Werke GmbH & CO. KG, Staufen, Germany) and samples were spun at 2000×g to pellet out tissue debris. The supernatant was further purified using a 0.2 µm filter. Tissue homogenates were then evaluated with regard to total in solution protein retrieval using a nanospec absorbance measurement standardized to BSA at 1 mg/mL (Pierce™, Thermo Fisher Scientific Inc, Waltham, USA). Homogenates were diluted to appropriate concentrations (e.g. 1 mg/ml total protein) with 25 mM PIPES, 0.5% Triton X-100 (Sigma Aldrich, St Louis, MA, USA) and pre-incubated with the probe (10 μM or 100 μM) at 37° C. in the dark for the designated period of time prior to fluorescence measurements. The resultant fluorescence was then measured using a Tecan Spark 10M Multi-Mode Microplate Reader (Tecan, Männedorf, Switzerland) at ambient temperature with a filter for excitation/emission (e.g. 405/460 nm respectively) as defined for the experiment. Activity is observed as fluorescence measured, and is expressed in relative fluorescent units (RFUs). Graphical presentation and statistical analysis were carried out using Graphpad Prism 7 software, (GraphPad Software, Inc., San Diego, USA.) with statistical significance determined as p<0.05.

Example 10: General Protocols for the Synthesis of Collagen Model Peptides 3, 4 and 5

Protocol A—General procedure for swelling: Before automated peptide synthesis, the resin was swelled in $CH_2Cl_2$ for 15 min while shaking. Then the resin was drained and washed with DMF (3×6 mL) and drained again. Protocol B—General protocol for automated peptide synthesis: For automated peptide synthesis, a Syro I peptide synthesizer (Biotage, Sweden) was used. Couplings were performed either with the appropriate Fmoc-protected amino acid or the trimer Fmoc-Pro-Hyp-Gly-OH. After swelling the resin in DMF on the synthesizer, i-$Pr_2$NEt (9 equiv. as a 3 M solution in NMP (N-methyl-2-pyrrolidone)), HATU (3 equiv., 0.5 M in DMF) and the Fmoc-amino acid/Fmoc-tripeptide (3 equiv., 0.5 M in DMF) were added to the resin. The mixture was allowed to react in intervals of 1 min. agitation and 5 min. rests for 30 min. (2×) and was then washed with DMF (5×). Fmoc-deprotection was carried out by addition of a solution of 40% (v/v) piperidine in DMF and reaction for 1 min. This step was repeated 4 times. The resin was then washed with DMF (5×). Tripeptide couplings and Fmoc-deprotections were repeated until the desired peptides were obtained. For the automated synthesis of CMPs no acylation (capping) was performed. Protocol C—On resin N-terminal functionalization with Compound 1: Functionalization was performed manually at room temperature on the solid support-bound peptide. Compound 1 (2.0 equiv.), HATU (1.9 equiv.) and i-$Pr_2$NEt (4 equiv.) were dissolved in DMF (1-2 mL). After pre-activation for 5 min, the coupling mixture was added to the resin and agitated for 1-2 hrs. The resin was washed with $CH_2Cl_2$ (3×), DMF (3×), $CH_2Cl_2$ (3×), and petroleum ether (2×). The reaction was monitored by the qualitative color tests on bead or by LC-MS after test cleavage (see Protocol E). Protocol D—Cleavage from the resin: The resin was shaken for 1 h in a mixture of TFA/(i-$Pr_2$)$_3$Si—H/$H_2O$ (92.5:2.5:2.5), and washed with pure TFA (2×). The peptide in solution was collected by filtration in a conical flask. Addition of ice-cold $Et_2O$ afforded the peptide as a white precipitate. The solid was isolated by centrifugation followed by decantation. The solid was suspended in $Et_2O$, sonicated, centrifuged again and the supernatant was decanted. The residual white solid was dissolved in water/$CH_3CN$, frozen, and lyophilized to obtain a white foam. Protocol E—Purification and analysis by RP HPLC: $CH_3CN$ (A) and $H_2O$ containing 1% $CH_3CN$ and 0.1% TFA (B) were used as eluents. For semi-preparative HPLC a flow rate of 6 mL/min, for analytical HPLC a flow rate of 1 mL/min and for LC-MS a flow rate of 0.5 mL/min was used. After purification by semi-preparative HPLC all collected fractions were analyzed by analytical HPLC or LC-MS and only pure fractions were combined. Amine containing CMPs were desalted with a VariPure cartridge prior to lyophilizing. Preparative Columns: Reprosil Gold 120 C18, 150×10 mm. Analytical Columns: Phenomenex, Jupiter 5 μm, 300 Å, 250×4.6 mm. LC-MS: Reprosil Gold C18 5 μm, 125×3 mm. Protocol F— Gel permeation chromatography: Nanopure $H_2O$ was used as eluent. A flow rate of 0.1 mL/min. was used at room temperature.

Example 11: Synthesis of 1-[ProHypGly]$_3$-AopPro-Gly-[ProHypGly]$_3$—$NH_2$ (Compound 3)

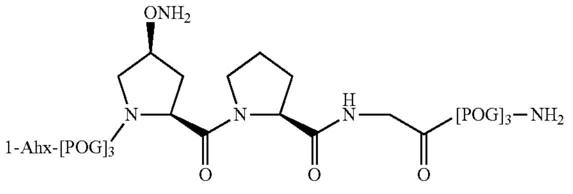

Compound 3 was synthesized on Rink amide ChemMatrix resin (~0.5 mmol/g). The resin was swelled according to protocol A. Fmoc-γ-Aminoxyproline(Aop)-OH, Fmoc-Pro-HypGly-OH, Fmoc-Pro-OH, and Fmoc-Gly-OH, and Fmoc-Ahx-OH, were coupled according to protocol B, and Compound 1 was coupled to the resin using the manual protocol C. Compound 3 was cleaved from the solid support according to protocol D and purified according to protocol E using a gradient of 92% B to 72% B over 20 min, tR=14.0 min. After desalting and lyophilization, Compound 3 was obtained as a white foam that was stored at −20° C. in the dark. Analytical reverse-phase HPLC: 91% to 60% B over 20 min, tR=8.99 min; Purity determined by analytical HPLC using UV detection at 214 nm: >97%. HRMS (MALDI): m/z calcd. for $[C_{105}H_{148}F_2N_{25}O_{33}]^+$: 2325.0634; found: 2325.0668 $[M+H]^+$.

Example 12: Synthesis of 1-Ahx-[ProHypGly]$_7$—$NH_2$ (Compound 4)

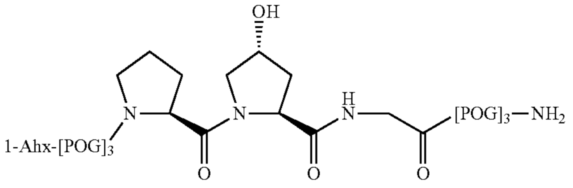

Compound 4 was synthesized on Rink amide ChemMatrix resin (~0.5 mmol/g). The resin was swelled according to protocol A. Fmoc-ProHypGly-OH and Fmoc-Ahx-OH were coupled according to protocol B, and Compound 1 was coupled to the resin using protocol C. Compound 4 was cleaved from the solid support according to protocol D and purified according to protocol E using a gradient of 92% B to 60% B over 20 min, $t_R$=15.1 min. After desalting and lyophilization, Compound 4 was obtained as a white foam that was stored at −20° C. in the dark. Analytical reverse-phase HPLC: 91% to 45% B over 20 min, $t_R$=7.47 min; Purity determined by analytical HPLC using UV detection at 214 nm: >97%. HRMS (MALDI): m/z calcd. for $[C_{105}H_{147}F_2N_{24}O_{33}]^+$: 2310.0525; found: 2310.0537 $[M+H]^+$.

Example 13a: Synthesis of 1-Ahx-[ProProGly]$_7$—NH$_2$ (Compound 5)

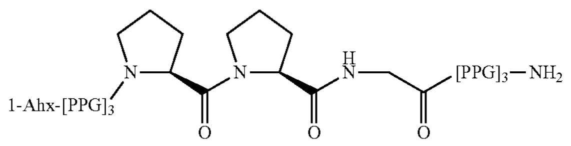

Compound 5 was synthesized on Rink amide ChemMatrix resin (~0.5 mmol/g). The resin was swelled according to protocol A. Fmoc-ProProGly-OH and Fmoc-Ahx-OH were coupled according to protocol B, and Compound 1 was coupled to the resin using protocol C. Compound 5 was cleaved from the solid support according to protocol D and purified according to protocol E using a gradient of 92% B to 62% B over 20 min, $t_R$=14.8 min. After desalting and lyophilization, Compound 5 was obtained as a white foam that was stored at −20° C. in the dark. Analytical reverse-phase HPLC: 91% B to 60% B over 20 min, $t_R$=13.7 min. Purity determined by analytical HPLC using UV detection at 214 nm: >99%. HRMS (MALDI): m/z for $[C_{105}H_{147}F_2N_{24}O_{26}]^+$: 2198.0881; found: 2198.0909 $[M+H]^+$.

Example 13b: Synthesis of 1-Ahx-[ProProGly]$_7$—NH$_2$ (Compound 6)

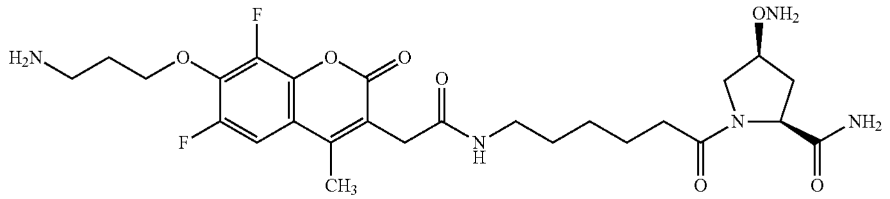

Compound 6 was synthesized on Rink amide ChemMatrix resin (~0.5 mmol/g). The resin was swollen according to protocol A. Fmoc-(4S)Aminoxyproline(Boc)-OH and Fmoc-Ahx-OH were coupled according to protocol B, and Compound 1 was coupled to the resin using the manual protocol C. The peptide was cleaved from the solid support according to protocol D and purified according to protocol E using a gradient of 98% B to 50% B over 20 min, $t_R$=10.1 min. After desalting and lyophilization, Compound 6 was obtained as a white foam that was stored at −20° C. in the dark. Analytical reverse-phase HPLC: 98% B to 40% B over 20 min, $t_R$=8.1 min. Purity determined by analytical HPLC using UV detection at 214 nm: >99%.

Example 14: CD Spectra of Compounds 3, 4, and 5

CD spectra (see FIG. 29) were recorded of 0.2 mM solution of Compounds 3, 4 and 5 in PBS buffer (pH=7.4) at 7° C. The solutions were equilibrated for >24 hrs. at 5° C. before measurement. The spectra were recorded from 190 nm to 260 nm.

Example 15: General Procedure for Determination of $T_m$-Values

The thermal denaturation experiments were performed with 0.2 mM solutions of Compounds 3, 4 and 5 that were equilibrated at 5° C. for at least 24 hrs in 50 mM PBS buffer (pH=7.4). The samples were heated with a heating rate of 1° C./100 s while monitoring the molar ellipticity at 224 nm. The experiment was repeated for each sample at least 3 times. The data obtained from the thermal denaturation experiments were fit to an all-or-none transition in which three single strands combine to a triple helix as previously reported by J. Engel, H. T. Chen, D. J. Prokop, H. Klump, *Biopolymers* 1997, 16, 601-622 and S. Frank, R. A. Kammerer, D. Mechling, T. Schulthess, R. Landwehr, J. Bann, Y. Guo, A. Lustig, H. P. Bächinger, J. Engel, *J. Mol. Biol.* 2001, 308, 1081-1089. The fit was performed using Micromath Scientist 3.0 with H=−500000 and Tm=40 as initial values. The model used is shown below:

//Model two state; IndVars: TEMP; DepVars: F, CD, K; Params: H, DEU, REFU, DEN, REFN, Tm; R=8.31; K=EXP(H/(R*(TEMP+273.15))*((TEMP+273.15)/(Tm+273.15)−1)-In(0.75*0.0002^2)); P=1/(3*K*(0.0002^2)); U=(−P/2+(P^2/4+P^3/27)^(½))^(⅓); V=−(P/2+(P^2/4+P^3/27)^(½))^(⅓); F=U+V+1; CDU=REFU+DEU*(TEMP+273.15); CDN=REFN+DEN*(TEMP+273.15); CD=F*(CDN−CDU)+CDU.

The thermal denaturation curves of Compounds 3, 4 and 5 are shown in FIG. 30.

Example 16: General Procedure for In Vivo Assays

Animals: Mice were housed and fed according to Swiss guidelines and all animal experiments were approved by the local veterinary authorities (Kantonales Veterinäramt Zürich). All mice used for these experiments are on a C57BL/6 background. Administration of Compounds 3, 4 and 5 into skin: Peptide solutions at 100 μM were brought to room temperature for 30 min. Male or female mice at 8 weeks of age were anesthetized by intraperitoneal injection of ketamine/xylazine (100 mg ketamine/5-10 mg xylazine per kg body weight), skin shaved and an injection of 50 μL was made intradermally into the back skin. Mice were housed for an additional five days and then skin harvested for histological analysis.

This example demonstrates the successful design and synthesis of a representative activity-based fluorescent compound according to the present invention which is capable of real-time quantification of lysyl oxidase activity in fibrotic conditions. The activation of the compound by enzymes was confirmed in ex vivo tissue homogenate models (see above), and demonstrated in vivo via conjugation to peptides that specifically and precisely target collagen and elastin undergoing real-time cross-linking and remodeling in the extracellular matrix. Additionally, the compounds according to the present invention with the addition of a conjugated peptide show utility for analysis of enzyme-mediated tissue remodeling in a relevant model of fibrogenesis.

Example 17: Synthesis of (5-((3-((Boc)amino)propyl)amino)-5-oxopentyl)triphenyl-phosphonium bromide

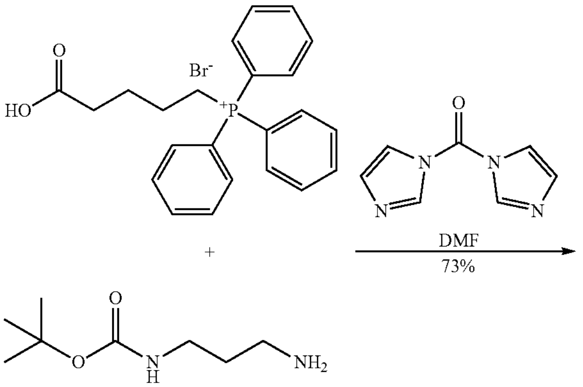

-continued

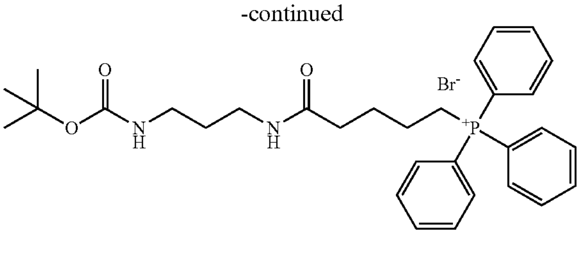

(4-Carboxybutyl)triphenyl-phosphonium bromide (2.26 mmol, 1 g) and 1,1'-carbonyldimidazole (2.26 mmol, 366 mg) were dissolved in anhydrous DMF (15 mL) and stirred for 30 min at room temperature. N-Boc-1,3-propanediamine (2.26 mmol, 393 mg) was added to the suspension, and stirred overnight. The crude mixture was concentrated by rotary evaporation, and purified by silica gel chromatography eluting with a gradient of 2-10% methanol in dichloromethane to yield (5-((3-((Boc)amino)propyl)amino)-5-oxopentyl)triphenylphosphonium bromide as a white foam (860 mg, 73%). $^{1}$H NMR (400 MHz, $CDCl_3$) δ 8.47 (t, J=6.0 Hz, 1H), 7.85-7.65 (m, 15H), 5.54 (t, J=5.7 Hz, 1H), 3.75-3.58 (m, 2H), 3.20 (q, J=6.2 Hz, 2H), 3.00 (q, J=6.2 Hz, 2H), 2.59 (t, J=6.8 Hz, 2H), 1.93 (q, J=7.0, 6.6 Hz, 2H), 1.68-1.55 (m, 4H), 1.39 (s, 9H). $^{13}$C NMR (101 MHz, $CDCl_3$) δ 173.30, 156.29, 135.23 (d, J=3.1 Hz), 133.77 (d, J=10.0 Hz), 130.60 (d, J=12.6 Hz), 118.12 (d, J=86.1 Hz), 78.62, 50.70, 36.53 (d, J=138.0 Hz), 34.17, 29.49, 28.59, 26.21 (d, J=17.0 Hz), 22.45 (d, J=50.7 Hz), 21.09 (d, J=4.2 Hz). $^{31}$P NMR (162 MHz, $CDCl_3$) δ 24.67. HRMS (ESI): m/z calcd. for $C_{31}H_{40}N_2O_3P$: 519.2771 $[M]^+$; found: 519.2764.

Example 17a: Synthesis of (5-((3-ammoniopropyl) amino)-5-oxopentyl)triphenyl-phosphonium chloride

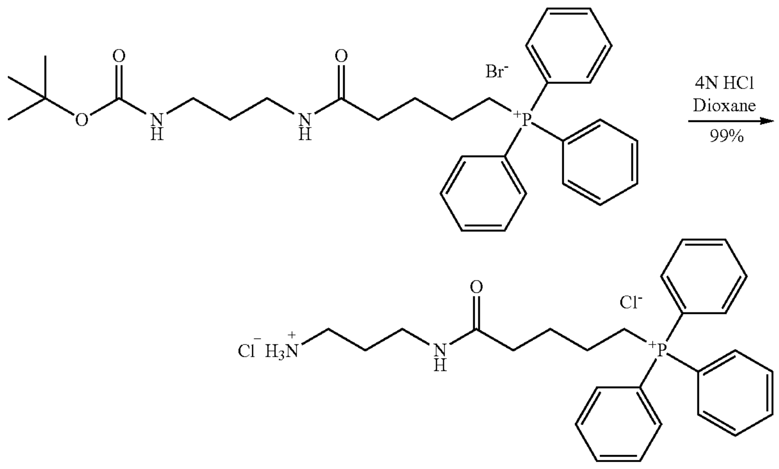

(4-Carboxybutyl)triphenyl-phosphonium bromide (2.26 mmol, 1 g) and 1,1'-carbonyldimidazole (2.26 mmol, 366 mg) were dissolved in anhydrous DMF (15 mL) and stirred for 30 min at room temperature. N-Boc-1,3-propanediamine (2.26 mmol, 393 mg) was added to the suspension, and stirred overnight. The crude mixture was concentrated by rotary evaporation, and purified by silica gel chromatography eluting with a gradient of 2-10% methanol in dichloromethane to yield (5-((3-ammoniopropyl)amino)-5-oxopentyl)triphenylphosphonium chloride as a white solid (860 mg, 73%). $^{1}$H NMR (400 MHz, MeOD) δ 7.92-7.72 (m, 15H), 3.50-3.41 (m, 2H), 3.22 (t, J=6.7 Hz, 2H), 2.91 (t, J=7.4 Hz, 2H), 2.29 (t, J=7.4 Hz, 2H), 1.89-1.77 (m, 4H), 1.76-1.64 (m, 2H). $^{13}$C NMR (101 MHz, MeOD) δ 175.94, 136.31 (d, J=3.1 Hz), 134.85 (d, J=10.0 Hz), 131.55 (d, J=12.6 Hz), 119.86 (d, J=86.5 Hz), 38.27, 36.92, 35.74, 28.67, 27.63 (d, J=17.4 Hz), 23.12 (d, J=4.1 Hz), 22.55 (d, J=51.6 Hz). $^{31}$P NMR (162 MHz, MeOD) δ 23.74. HRMS (ESI): m/z calcd. for $C_{26}H_{32}N_2OP$: 419.2247 $[M]^+$; found: 419.2241.

Example 17b: Synthesis of MRA_3103

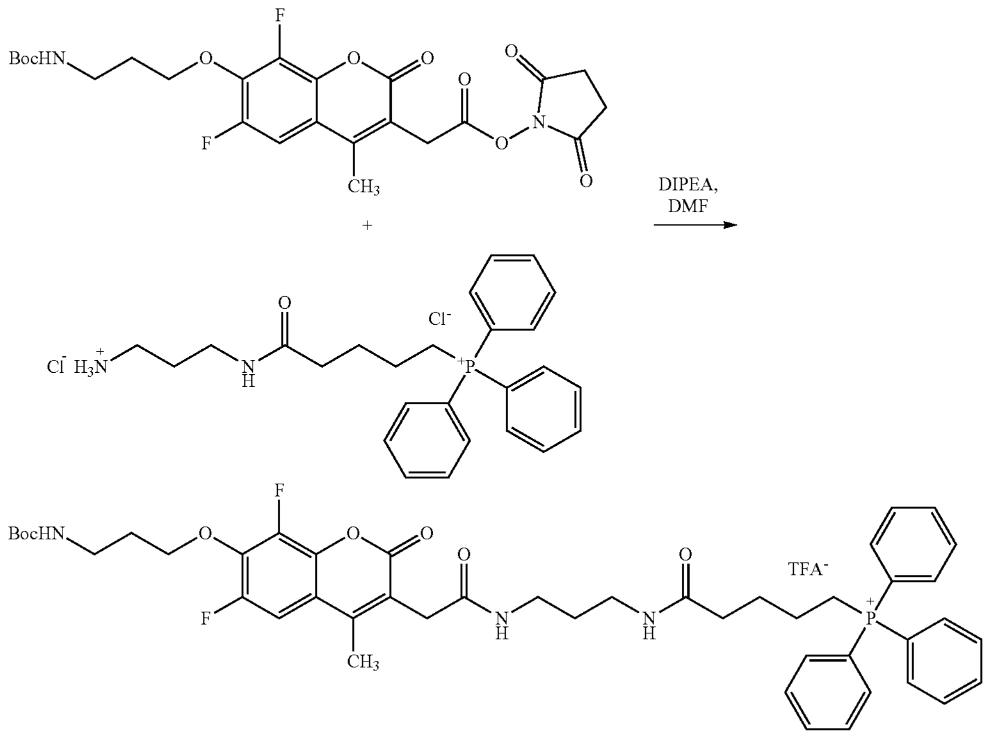

(5-((3-ammoniopropyl)amino)-5-oxopentyl)triphenylphosphonium chloride (0.21 mmol, 89 mg) was dissolved in anhydrous DMF (1.4 mL) and cooled to 0° C. with stirring. N,N-Diisopropylethylamine (0.424 mmol, 74 μL) was added, followed by MRA_3102 (0.19 mmol, 100 mg), and the solution was allowed to warm to room temperature and stir overnight. The crude mixture was concentrated by rotary evaporation, and purified by RP-HPLC with a gradient of 90-10% acetonitrile in water with 0.1% TFA. Fractions containing product as determined by HPLC-MS were combined, flash frozen, and lyophilized to yield MRA_3103 as a white solid (14 mg, 9%). $^{1}H$ NMR (600 MHz, $CD_3CN$) δ 7.88-7.82 (m, 3H), 7.72-7.65 (m, 12H), 7.37 (dd, J=12.0, 2.2 Hz, 1H), 6.94 (t, J=5.9 Hz, 1H), 6.77 (t, J=5.6 Hz, 1H), 5.46 (s, 1H), 4.30 (t, J=6.2 Hz, 2H), 3.52 (s, 2H), 3.24-3.16 (m, 4H), 3.06 (dq, J=12.9, 6.3 Hz, 4H), 2.35 (s, 3H), 2.13 (t, J=7.1 Hz, 2H), 1.89 (p, J=6.5 Hz, 2H), 1.72 (p, J=7.2 Hz, 2H), 1.60 (dq, J=15.8, 7.7 Hz, 2H), 1.49 (p, J=6.6 Hz, 2H), 1.38 (s, 9H). $^{19}F$ NMR (F-H decoupled) (376 MHz, $CD_3CN$) δ −133.94 (d, J=5.2 Hz), −150.46 (d, J=6.0 Hz). $^{19}F$ NMR (376 MHz, $CD_3CN$) δ −133.94 (dd, J=12.7, 5.8 Hz), −150.46 (d, J=6.3 Hz). $^{31}P$ NMR (162 MHz, $CD_3CN$) δ 23.50. $^{13}C$ NMR (151 MHz, $CD_3CN$) δ 173.51, 170.28, 161.20, 157.08, 152.47 (dd, J=242.9, 4.5 Hz), 149.91, 143.78 (dd, J=248.9, 6.2 Hz), 139.49 (dd, J=10.1, 1.9 Hz), 138.66 (dd, J=16.1, 11.0 Hz), 136.11 (d, J=3.1 Hz), 134.61 (d, J=10.0 Hz), 131.26 (d, J=12.6 Hz), 121.60, 119.56, 118.99, 116.69 (d, J=9.2 Hz), 107.71 (dd, J=22.7, 3.5 Hz), 79.27, 73.85, 37.85, 37.21, 36.93, 35.68, 35.49, 31.20, 30.07, 28.60, 27.05 (d, J=17.3 Hz), 22.44 (d, J=4.1 Hz), 22.40 (d, J=51.8 Hz), 16.10. HRMS (ESI): m/z calcd. for $C_{46}H_{53}F_2N_3O_7P$: 828.3584 $[M]^+$; found: 828.3582.

Example 18: General Protocols for the Synthesis of Mitochondrial-Targeting Peptides Protocol A—General Procedure for Swelling Before automated peptide synthesis, the resin was swelled in $CH_2Cl_2$ for 15 min while shaking. Then the resin was drained and washed with DMF (3×6 mL) and drained again.

Protocol B—General Protocol for Automated Peptide Synthesis

For automated peptide synthesis, a Syro I peptide synthesizer (Biotage, Sweden) was used. Couplings were performed either with the appropriate Fmoc-protected amino acid or the trimer Fmoc-Pro-Hyp-Gly-OH. After swelling the resin in DMF on the synthesizer, $i-Pr_2NEt$ (9 equiv. as a 3 M solution in NMP (N-methyl-2-pyrrolidone)), HATU (3 equiv., 0.5 M in DMF) and the Fmoc-amino acid/Fmoc-tripeptide (3 equiv., 0.5 M in DMF) were added to the resin. The mixture was allowed to react in intervals of 1 min. agitation and 5 min. rests for 30 min. (2×) and was then washed with DMF (5×). Fmoc-deprotection was carried out by addition of a solution of 40% (v/v) piperidine in DMF and reaction for 1 min. This step was repeated 4 times. The resin was then washed with DMF (5×). Tripeptide couplings and Fmoc-deprotections were repeated until the desired peptides were obtained. For the automated synthesis of CMPs no acylation (capping) was performed.

Protocol C—on Resin N-Terminal Functionalization with Compound 1

Functionalization was performed manually at room temperature on the solid support-bound peptide. Compound 1 (2.0 equiv.), HATU (1.9 equiv.) and i-$Pr_2NEt$ (4 equiv.) were dissolved in DMF (1-2 mL). After pre-activation for 5 min, the coupling mixture was added to the resin and agitated for 1-2 hrs. The resin was washed with $CH_2Cl_2$ (3×), DMF (3×), $CH_2Cl_2$ (3×), and petroleum ether (2×). The reaction was monitored by the qualitative color tests on bead or by LC-MS after test cleavage (see Protocol E).

Protocol D—Cleavage from the Resin

The resin was shaken for 1 h in a mixture of TFA/(i-$Pr_2$)$_3$Si—H/$H_2O$ (92.5:2.5:2.5), and washed with pure TFA (2×). The peptide in solution was collected by filtration in a conical flask. Addition of ice-cold $Et_2O$ afforded the peptide as a white precipitate. The solid was isolated by centrifugation followed by decantation. The solid was suspended in $Et_2O$, sonicated, centrifuged again and the supernatant was decanted. The residual white solid was dissolved in water/$CH_3CN$, frozen, and lyophilized to obtain a white foam.

Protocol E—Purification and Analysis by RP HPLC

For semi-preparative HPLC, $H_2O$ containing 1% $CH_3CN$ and 0.1% TFA (A) and $CH_3CN$ (B) were used as eluents. For semi-preparative HPLC a flow rate of 6 mL/min, for analytical HPLC a flow rate of 1 mL/min and for LC-MS a flow rate of 0.5 mL/min was used. After purification by semi-preparative HPLC all collected fractions were analyzed by analytical HPLC or LC-MS and only pure fractions were combined. For analytical HPLC, $CH_3CN$ (A) and $H_2O$ containing 1% $CH_3CN$ and 0.1% TFA (B) were used as eluents. Amine containing CMPs were desalted with a VariPure cartridge prior to lyophilizing.

Preparative Columns: Reprosil Gold 120 C18, 150×10 mm. Analytical Columns: Phenomenex, Jupiter 5 μm, 300 Å, 250×4.6 mm. LC-MS: Reprosil Gold C18, 125×3 mm.

Example 18a: Synthesis of 1-Ahx-[Char]$_3$—$NH_2$

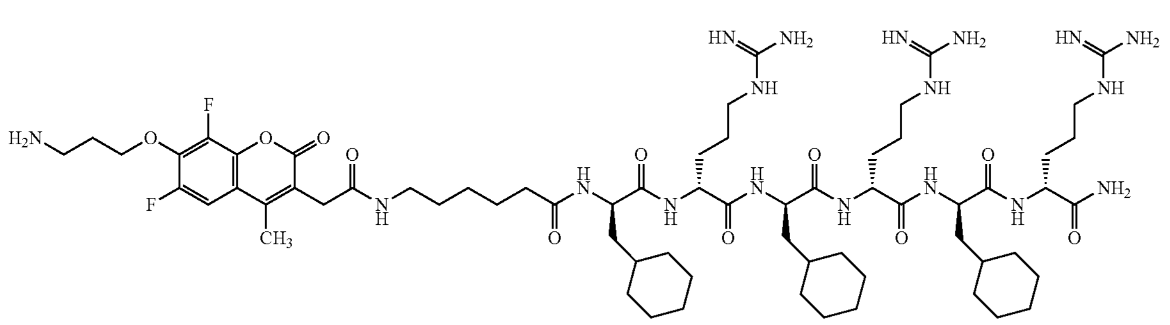 [SMILES: Cc1c(CC(=O)NCCCCCC(=O)N[C@H](CC2CCCCC2)C(=O)N[C@H](CCCNC(=N)N)C(=O)N[C@H](CC2CCCCC2)C(=O)N[C@H](CCCNC(=N)N)C(=O)N[C@H](CC2CCCCC2)C(=O)N[C@H](CCCNC(=N)N)C(N)=O)c(=O)oc2c(F)c(OCCCN)c(F)cc12]

The peptide was synthesized on Rink amide resin (~0.5 mmol/g). The resin was swelled according to protocol A. Fmoc-D-Arginine(Boc)-OH, Fmoc-Cha-OH, and Fmoc-Ahx-OH, were coupled according to protocol B, and Compound 1 was coupled to the resin using the manual protocol C. The peptide was cleaved from the solid support according to protocol D and purified according to protocol E using a gradient of 15% B to 40% B over 20 min, $t_R$=11.4 min. After desalting and lyophilization, the peptide was obtained as a white foam that was stored at −20° C. in the dark. Analytical reverse-phase HPLC: 90% to 10% B over 20 min, $t_R$=8.3 min; Purity determined by analytical HPLC using UV detection at 214 nm: >99%. HRMS (MALDI): m/z calcd. for $[C_{66}H_{110}F_2N_{18}O_{11}]^{2+}$: 684.4279; found: 684.4269 $[M+H]^{2+}$.

Example 18b: Synthesis of MRA_3069-Ahx-(ChaR)$_3$—$NH_2$

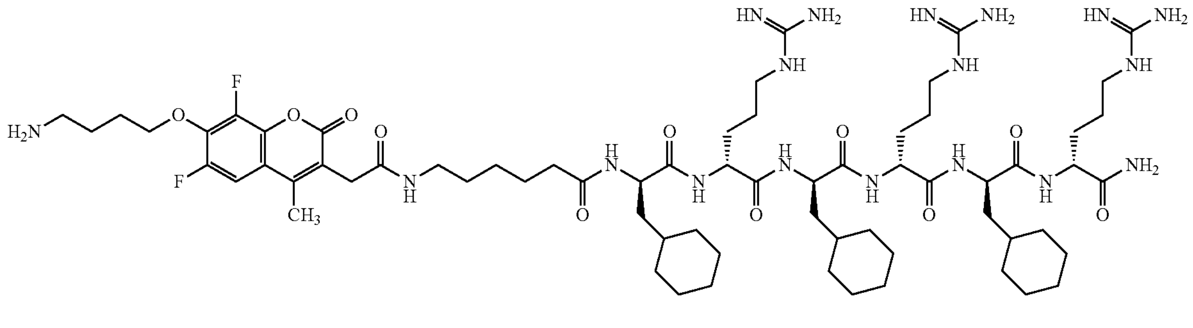 [SMILES: Cc1c(CC(=O)NCCCCCC(=O)N[C@H](CC2CCCCC2)C(=O)N[C@H](CCCNC(=N)N)C(=O)N[C@H](CC2CCCCC2)C(=O)N[C@H](CCCNC(=N)N)C(=O)N[C@H](CC2CCCCC2)C(=O)N[C@H](CCCNC(=N)N)C(N)=O)c(=O)oc2c(F)c(OCCCCN)c(F)cc12]

The peptide was synthesized on Rink amide resin (~0.5 mmol/g). The resin was swelled according to protocol A. Fmoc-D-Arginine(Boc)-OH, Fmoc-Cha-OH, and Fmoc-Ahx-OH, were coupled according to protocol B, and MRA_3069 was coupled to the resin using the manual protocol C. The peptide was cleaved from the solid support according to protocol D and purified according to protocol E using a gradient of 15% to 48% B over 20 min, $t_R$=15.0 min. After desalting and lyophilization, the peptide was obtained as a white foam that was stored at −20° C. in the dark. Analytical reverse-phase HPLC: 10% to 90% B over 20 min, $t_R$=8.7 min; Purity determined by analytical HPLC using UV detection at 214 nm: >95%. HRMS (MALDI): m/z calcd. for $[C_{66}H_{110}F_2N_{18}O_{11}]^{2+}$: 691.4358; found: 691.4343 $[M+H]^{2+}$ Example 18c: Synthesis of PB-Ahx-(ChaR)$_3$—$NH_2$

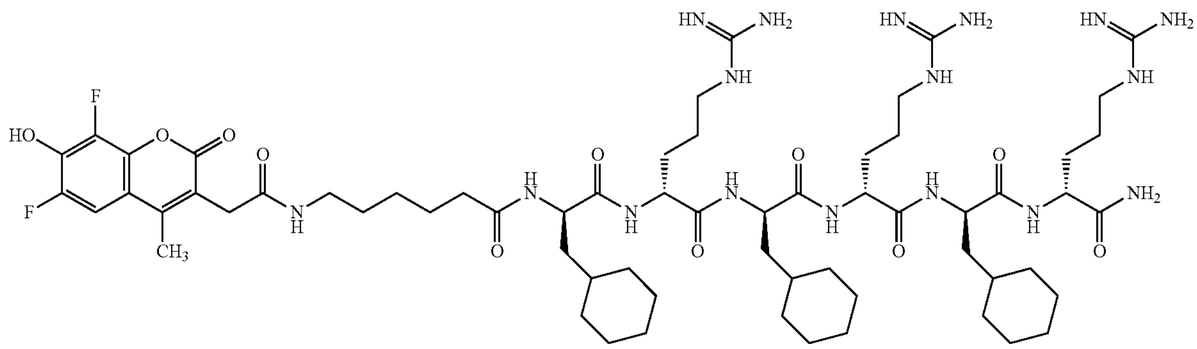 [SMILES: Cc1c(CC(=O)NCCCCCC(=O)N[C@H](CC2CCCCC2)C(=O)N[C@H](CCCNC(=N)N)C(=O)N[C@H](CC2CCCCC2)C(=O)N[C@H](CCCNC(=N)N)C(=O)N[C@H](CC2CCCCC2)C(=O)N[C@H](CCCNC(=N)N)C(N)=O)c(=O)oc2c(F)c(O)c(F)cc12]

The peptide was synthesized on Rink amide resin (~0.5 mmol/g). The resin was swelled according to protocol A. Fmoc-D-Arginine(Boc)-OH, Fmoc-Cha-OH, and Fmoc-Ahx-OH, were coupled according to protocol B. Pacific Blue (PB) NHS was coupled to the resin directly using the manual protocol C, but without the addition of HATU. The peptide was cleaved from the solid support according to protocol D and purified according to protocol E using a gradient of 15% B to 60% B over 20 min, $t_R$=13.9 min. After desalting and lyophilization, the peptide was obtained as a white foam that was stored at ~20° C. in the dark. Analytical reverse-phase HPLC: 10% to 90% B over 20 min, $t_R$=9.56 min; Purity determined by analytical HPLC using UV detection at 214 nm: >99%. HRMS (MALDI): m/z calcd. for $[C_{63}H_{103}F_2N_{17}O_{11}]^{2+}$: 655.899; found: 655.8979 $[M+H]^{2+}$.

Example 19: Cellular Assays for the Determination of Monamine Oxidase Activity from MAO A/MAO B Cell culture: MCF-7 and SY5Y cells were obtained from the Health Protection Agency (www.HPA.org.uk) or the American Type Culture Collection. The cells were grown in a humidified 5% $CO_2$ atmosphere at 37° C. using Kaighn's Modification of Ham's F-12 medium (F-12KTM) supplemented with L-glutamine (4 mM), penicillin (100 U/mL penicillin), streptomycin (100 g/mL), and 10% fetal calf serum (FCS) superior (standardized). Culture medium DMEM high glucose, F-12KTM, L-glutamine (200 mM), penicillin (10.000 U/mL), streptomycin (10 mg/mL), and trypan blue solution were purchased from Sigma, Invitrogen, ATCC or BioConcept. Trypsin-EDTA (0.05%/0.02%) in Ca2+- and Mg2+-deficient phosphate buffered saline (PBS) (1:250) was purchased from Amimed. PBS (pH 7.4) was purchased from Invitrogen. FCS superior was bought fromOxoid AG and Biochrom AG. Cell culture flasks as well as serological pipettes were purchased from BD Biosciences and Sarstedt. Ethylenediaminetetraacetic acid (EDTA) was purchased from Sigma-Aldrich. Hoechst 33342 was purchased from Invitrogen. MitoTracker Red mitochondrial staining dye and live cell imaging solution were purchased from ThermoFisher.

Confocal Microscopy: Fluorescence images of cells were collected using a Nikon Eclipse T1 microscope equipped with a Yokogawa spinning-disk confocal scanner unit CSU-W1-T2, two sCMOS cameras (Orca Flash 4.0 V2) and a LUDL BioPrecision2 stage with piezo focus. Emission in the blue channel was filtered with a 450/50 bandpass filter, emission in the green channel was filtered with a 525/50 bandpass filter and emission in the far-red channel with a 700/75 bandpass filter. Fluorescence images were obtained using an oil-immersion objective with a magnification of 100×1.49 CFI Apo TIRF. The microscope was operated using VisiVIEW (Metamorph).

Prior to the measurement, cells were seeded at a density of 10'000 cells/well in ibidi 8-well plates and were grown for 1 day in DMEM (10% FCS) at 37° C. Afterwards cells were washed with PBS and fresh DMEM was added. Compounds were added to the cells as stock solutions in PBS to reach the final 10 mM concentration. The cells were incubated for two hours at 37° C., washed with PBS and incubated with MitoTracker Red based on the manufacturers recommended procedure for 5 min at 37° C. Cells were washed with PBS and the live cell imaging solution (200 μL) was added. The live cells were then immediately examined on a confocal microscope (Vistron Spinning Disk). For detection of the coumarin-activation a laser line 405 nm and for MitoTracker a laser line of 561 nm was used.

Example 20: Biochemical and Histological Analysis of the Skin Treated with Compounds 3 to 6

Skin tissue used for histology was harvested and immediately embedded and frozen in tissue freezing Medium® (Leica Biosystems, Wetzlar, Germany). Tissue sections (7 μM) were fixed using ice-cold acetone for 10 min at −20° C. and stained with propidium iodide to visualize nuclei. Images were taken using a 20× objective. For immunofluorescent analysis of collagen, antibodies against collagen I (Southern Biotech, Birmingham, AL, USA; 1310-01) or collagen III (Abcam, Cambridge, UK, ab7778) were used. Fixed tissue sections were incubated with 1% bovine serum albumin (BSA) in PBS for 30 min followed by collagen I (1:400 dilution in 1% BSA) or collagen III (1:800 dilution in 1% BSA) antibodies for 60 min at room temperature. After washing (3×5 min PBS), secondary antibodies (anti-rabbit AF488 (711-547-003) or anti-goat AF488 (705-545-147), Jackson ImmunoResearch) were incubated on the tissues for 30 min at room temperature (both at 1:400 dilution in 1% BSA) and nuclei visualized using propidium iodide. All images were taken using a 20× objective.

Example 21: Biochemical and Histological Analysis of Tissue Sections Treated with Compounds 3 to 6

Skin tissue used for histology was harvested and immediately embedded and frozen in tissue freezing Medium®

(Leica Biosystems, Wetzlar, Germany). Tissue sections (7 uM) were treated by the addition of 50 μL of each compound at 100 μM in PBS (Compounds 3, 4, 5, or 6) by pipette to completely cover the surface of the section, incubated at 37° C. for 4 hours in the dark, and washed 2× with PBS. Sections were fixed using ice-cold acetone for 10 min at −20° C. and stained with propidium iodide to visualize nuclei. Images were taken using a 20× objective.

For immunofluorescent analysis of collagen, antibodies against collagen I (Southern Biotech, 1310-01) or collagen III (Abcam, ab7778) were used. Fixed tissue sections were incubated with collagen I or collagen III antibodies for 60 min at room temperature. After washing, secondary antibodies (anti-rabbit AF488 (711-547-003) or anti-goat AF488 (705-545-147), Jackson ImmunoResearch) were incubated on the tissues for 30 min at room temperature and nuclei visualized using propidium iodide. All images were taken using a 20× objective.

The invention claimed is:

1. A compound according to Formula I

Formula I

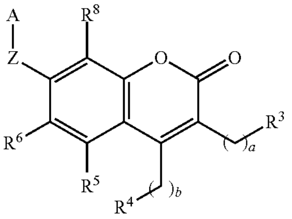

wherein a and b are independently an integer from 0 to 10;

A is a structure selected from the group consisting of

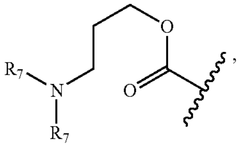

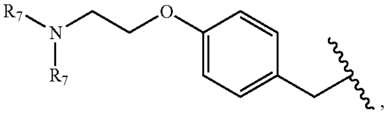

-continued

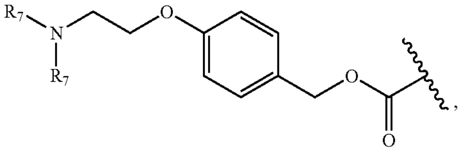

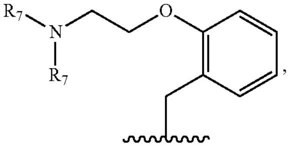

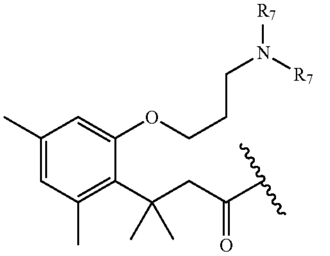

and

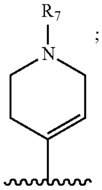

;

$R^3$ and $R^4$ are independently selected from the group consisting of $NHR^{9'}$, —$OR^{9'}$, $SR^{9'}$,

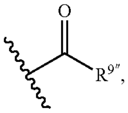

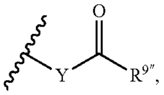

-continued

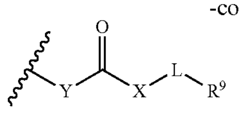

and

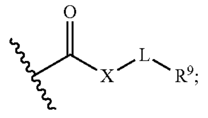

linear or branched, substituted or non-substituted ($C_{1-10}$) alkyl, ($C_{2-10}$)alkenyl and ($C_{2-10}$)alkynyl, or substituted or non-substituted carbocycle selected from the group consisting of ($C_{3-10}$)carbocycle;

substituted or non-substituted triphenylphosphine connected via the phosphorous;

N-maleimidyl; and halogens, or one of $R^3$ or $R^4$ is a proteinogenic amino acid, a non-proteinogenic amino acid or a peptide, and the other of $R^3$ or $R^4$ is a halogen;

L is absent or a linker;

X, Y and Z are independently selected from the group consisting of O, N and S;

$R^{9'}$ is selected from the group consisting of hydrogen;

linear or branched, substituted or non-substituted, optionally sulfonated, ($C_{1-10}$)alkyl, ($C_{2-10}$)alkenyl, or ($C_{2-10}$)alkynyl;

linear or branched, substituted or non-substituted ($C_{1-20}$)alkyl ether, ($C_{2-10}$)alkenyl ether, ($C_{2-10}$)alkynyl ether, or ($C_{4-10}$)carbocyclic ether;

substituted or non-substituted carbocycle selected from the group consisting of ($C_{3-10}$)carbocycle;

substituted or non-substituted triphenylphosphine connected via the phosphorous;

substituted or non-substituted ($C_{3-6}$)heterocycle and ($C_7$-$C_{10}$)carbo- or hetero-bicycle having 1 to 3 heteroatoms each independently selected from N, O and S;

a proteinogenic amino acid or non-proteinogenic amino acid;

a peptide or a peptide comprising 1 to 2000 amino acids;

a collagen peptide, fibronectin peptide, fibrillin peptide, elastin peptide, or an RGD (arginylglycylaspartic acid) peptide; and an antibody;

$R^9$ is selected from residues defined for $R^{9'}$ and is further selected from the group consisting of azide, N-maleimidyl, —$NH_2$, —OH and —$SH_2$;

$R^{9''}$ is selected from the group consisting of halogen, substituted or non-substituted triphenylphosphine connected via the phosphorous, azide, —$SR^{10}$,

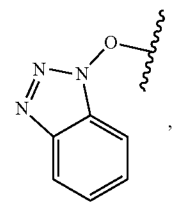

,

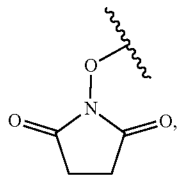

-continued

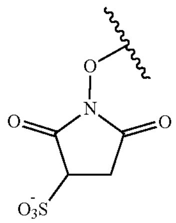

and

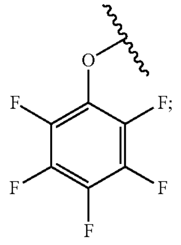

$R^{10}$ is selected from the group consisting of linear or branched, substituted or non-substituted ($C_{1-10}$)alkyl, ($C_{2-10}$)alkenyl, or ($C_{2-10}$)alkynyl; and linear or branched, substituted or non-substitutedqj ($C_{1-20}$)alkyl ether, ($C_{2-10}$)alkenyl ether, ($C_{2-10}$)alkynyl ether, or ($C_{4-10}$)carbocyclic ether;

$R^5$ is selected from the group consisting of hydrogen or —OH; and halogens;

$R^6$ and $R^8$ are independently selected from the group consisting of hydrogen, —OH, and halogen; and $R^7$ is each independently selected from the group consisting of hydrogen;

linear or branched, substituted or non-substituted ($C_{1-10}$)alkyl, ($C_{2-10}$) alkenyl, or ($C_{2-10}$)alkynyl;

linear or branched, substituted or non-substituted ($C_{1-20}$)alkyl ether, ($C_{2-10}$)alkenyl ether, ($C_{2-10}$)alkynyl ether, or ($C_{4-10}$)carbocyclic ether;

—$N_2$ forming an azide with the nitrogen atom of A; and tert-Butyloxycarbonyl (Boc), 9-fluorenylmethoxycarbonyl (Fmoc), benzyloxycarbonyl(Cbz), acetyl (Ac), trifluoroacetic acid (TFA), phthalimide, benzyl (Bn), triphenylmethyl (Tr), benzylidene, or para-toluenesulfonyl (Ts);

and salts and solvates thereof.

2. The compound according to claim 1, wherein a and b are independently an integer from 0 to 3;

A is a structure selected from the group consisting of

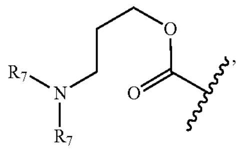

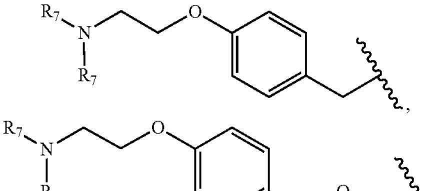

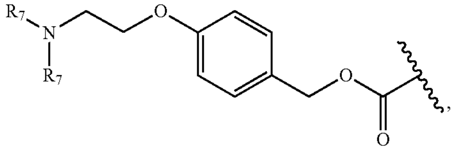

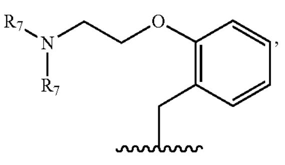

-continued

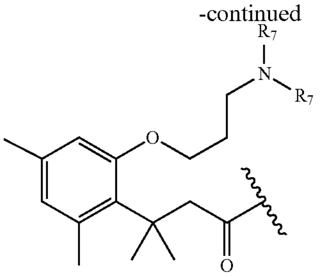

and

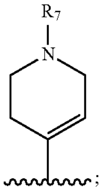

;

$R^3$ and $R^4$ are independently selected from the group consisting of

—$NHR^{9'}$, —$OR^{9'}$, $SR^{9'}$,

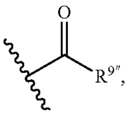

,

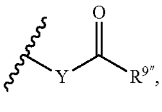

,

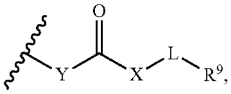

, or

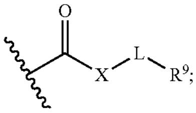

;

linear or branched, substituted or non-substituted ($C_{1-10}$) alkyl;

triphenylphosphine connected via the phosphorous;

N-maleimidyl; and halogen or one of $R^3$ or $R^4$ is a proteinogenic amino acid, a non-proteinogenic amino acid or a peptide, and the other of $R^3$ or $R^4$ is a halogen;

L is absent or a linker selected from the group consisting of linear or branched, substituted or non-substituted ($C_{1-10}$)alkyl;

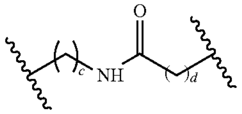

or

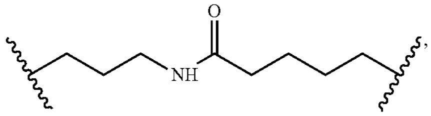

, wherein c and d are independently selected from 1, 2, 3, 4, and 5; and linear or branched, substituted or non-substituted ($C_{1-20}$) alkyl ether;

X, Y and Z are independently selected from the group consisting of O, N and S;

$R^{9'}$ is selected from the group consisting of hydrogen;

linear or branched, substituted or non-substituted, optionally sulfonated, ($C_{1-10}$)alkyl, ($C_{2-10}$)alkenyl, or ($C_{2-10}$)alkynyl;

linear or branched, substituted or non-substituted ($C_{1-20}$)alkyl ether;

triphenylphosphine connected via the phosphorous;

a proteinogenic amino acid or a non-proteinogenic amino acid;

a peptide or a peptide comprising 1 to 2000 amino acids;

a collagen peptide, fibronectin peptide, fibrillin peptide, elastin peptide, or an RGD (arginylglycylaspartic acid) peptide; and an antibody;

$R^9$ is selected from residues defined for $R^{9'}$ and is further selected from the group consisting of azide, N-maleimidyl, —$NH_2$, —OH and —$SH_2$;

$R^{9''}$ is selected from the group consisting of azide, —$SR^{10}$,

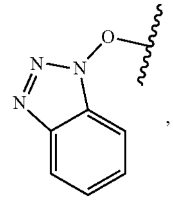

,

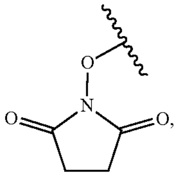

,

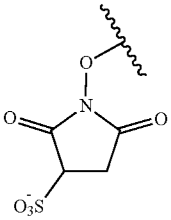

and

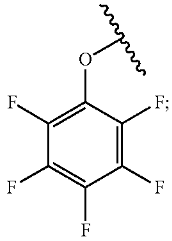

;

$R^{10}$ is selected from the group consisting of linear or branched, substituted or non-substituted ($C_{1-10}$)alkyl; and linear or branched, substituted or non-substituted ($C_{1-20}$)alkyl ether;

$R^5$ is selected from the group consisting of hydrogen or —OH; and halogen;

$R^6$ and $R^8$ are independently selected from the group consisting of hydrogen and halogen; and $R^7$ is each independently selected from the group consisting of hydrogen;

linear or branched, substituted or non-substituted ($C_{1-10}$)alkyl;

linear or branched, substituted or non-substituted ($C_{1-20}$)alkyl ether;

—$N_2$ forming an azide with the nitrogen atom of A; and

Boc, Fmoc, Cbz, Ac, TFA, phthalimide, Bn, Tr, benzylidene, or Ts.

3. The compound according to claim 1, wherein a is an integer from 0 to 3;

b is 0;

A is a structure selected from the group consisting of

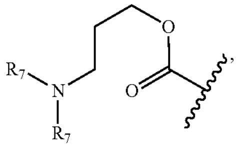

,

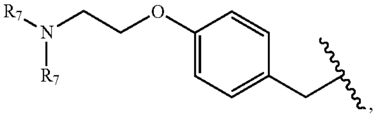

,

-continued

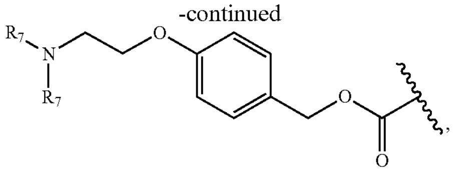

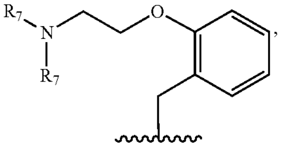

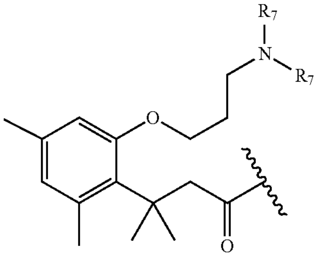

and

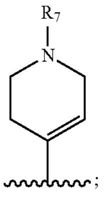

$R^3$ is

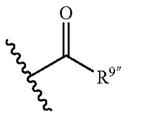

or

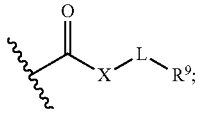

$R^4$ is hydrogen, linear or branched, substituted or non-substituted $(C_{1-10})$alkyl;

L is absent or a linker selected from the group consisting of linear or branched, substituted or non-substituted $(C_{1-10})$alkyl;

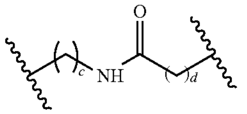

or

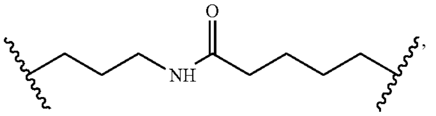

wherein c and d are independently selected from 1, 2, 3, 4, and 5; and linear or branched, substituted or non-substituted $(C_{1-10})$ alkyl ether;

X is selected from the group consisting of O, N and S;

Z is O;

$R^9$ is selected from the group consisting of hydrogen or N-maleimidyl;

linear or branched, substituted or non-substituted $(C_{1-10})$alkyl, $(C_{2-10})$alkenyl, or $(C_{2-10})$alkynyl;

linear or branched, substituted or non-substituted $(C_{1-20})$ alkyl ether;

triphenylphosphine connected via the phosphorous:

a proteinogenic amino acid, a non-proteinogenic amino acid, lysine, proline, glycine, 4-hydroxyproline, 4-aminoproline, or 4-aminooxyproline;

a peptide or a peptide comprising 1 to 2000 amino acids;

a collagen peptide, fibronectin peptide, fibrillin peptide, elastin peptide, or an RGD (arginylglycylaspartic acid) peptide;

an antibody an anti-collagen, anti-elastin, anti-fibronectin, or anti-fibrillin antibody; and azide, $—NH_2$, —OH, or $—SH_2$;

$R^{9''}$ is selected from the group consisting of azide, $—SR^{10}$,

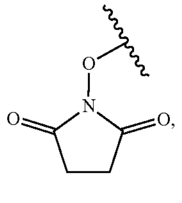

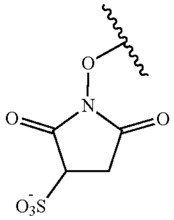

and

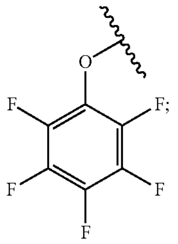

$R^{10}$ is selected from the group consisting of linear or branched, substituted or non-substituted $(C_{1-10})$alkyl, $(C_{2-10})$alkenyl, and $(C_{2-10})$ )alkynyl;

$R^5$ is selected from the group consisting of hydrogen or —OH; and halogen;

$R^6$ and $R^8$ are independently selected from the group consisting of hydrogen and halogen; and $R^7$ is each independently selected from the group consisting of hydrogen;

linear or branched, substituted or non-substituted $(C_{1-10})$alkyl;

$—N_2$ forming an azide with the nitrogen atom of A; and

Boc, Fmoc, or Cbz.

4. The compound according to claim 1, wherein the compound is a compound according to Formula II Formula II

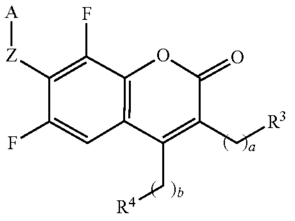

wherein a is 1 or 2;

b is 0;

A is a structure selected from the group consisting of

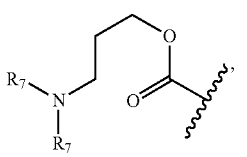

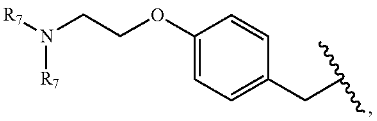

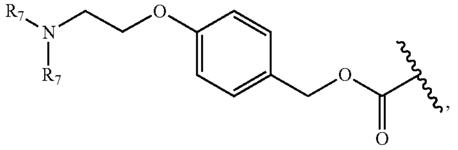

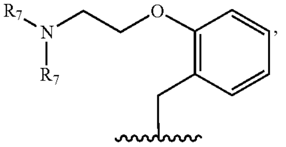

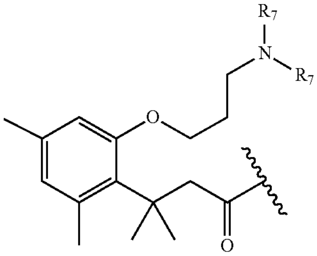

and

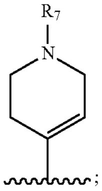

$R^3$ is

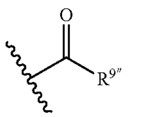

or

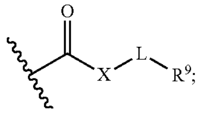

$R^4$ is hydrogen or linear or branched, substituted or non-substituted $(C_{1-10})$alkyl;

L is absent,

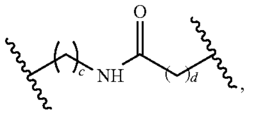

, or

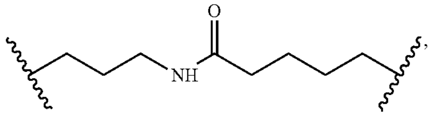

wherein c and d are independently selected from 1, 2, 3, 4, and 5;

X is selected from the group consisting of O and N;

Z is O;

$R^9$ is selected from the group consisting of hydrogen or N-maleimidyl;

linear or branched, substituted or non-substitutedqj $(C_{1-10})$alkyl;

triphenylphosphine connected via the phosphorous;

a proteinogenic amino acid, a non-proteinogenic amino acid, lysine, proline, glycine, 4-hydroxyproline, 4-aminoproline, or 4-aminooxyproline;

a collagen peptide, fibronectin peptide, fibrillin peptide, elastin peptide, or an RGD (arginylglycylaspartic acid) peptide; and azide, $—NH_2$, —OH and $—SH_2$;

$R^{9''}$ is selected from the group consisting of azide,

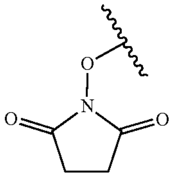

and

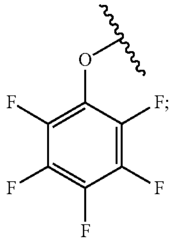

and $R^7$ is each independently selected from the group consisting of hydrogen; and linear or branched, substituted or non-substituted $(C_{1-10})$alkyl.

5. The compound according to claim 1, wherein the linear or branched, substituted or non-substituted $(C_{1-10})$alkyl for at least one of $R^3$, $R^4$, $R^7$, $R^{9'}$ and/or $R^{10}$ is selected from methyl, ethyl, and propyl.

6. The compound according to claim 1, wherein the $(C_{3-10})$carbocycle for at least one of $R^3$, $R^4$ and/or $R^{9'}$ is an aromatic $(C_6)$carbocycle.

7. The compound according to claim 1, wherein $R^3$ and/or $R^4$ are an aromatic $(C_6)$carbocycle if a and/or b are 0.

8. The compound according to claim 1, wherein for at least one of $R^3$, $R^4$, $R^5$, $R^6$, $R^8$ and/or $R^{9''}$ the halogen is selected from F, Cl, Br, and I.

9. The compound according to claim 1, wherein if one of $R^3$ or $R^4$ is a proteinogenic amino acid, a non-proteinogenic amino acid, or a peptide, the other of $R^3$ or $R^4$ is a halogen.

10. The compound according to claim 1, wherein the linker is selected from the group consisting of:

linear or branched, substituted or non-substituted $(C_{1-10})$ alkyl, $(C_{2-10})$alkenyl, or $(C_{2-10})$alkynyl;

a $(C_{1-10})$ alkyl comprising one or more amide functionalities in the alkyl chain;

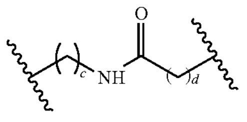

or

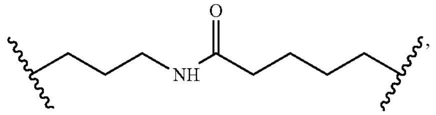

wherein c and d are independently selected from 1, 2, 3, 4, and 5; and linear or branched, substituted or non-substituted $(C_{1-20})$ alkyl ether, $(C_{2-10})$alkenyl ether, $(C_{2-10})$alkynyl ether, and $(C_{4-10})$carbocyclic ether.

11. The compound according to claim 1, wherein Z is selected from the group consisting of O and N.

12. The compound according to claim 1, wherein for at least one of $R^7$, $R^9$ and/or $R^{10}$, the $(C_{1-20})$alkyl ether is a polyethylene glycol (PEG) chain or a PEG chain with 1 to 10 ethylene oxide entities.

13. The compound according to claim 1, wherein for $R^{9'}$, the $(C_{3-10})$carbocycle is a carbocycle substituted by a substituent selected from the group consisting of Cl, F, Br, substituted or non-substituted methyl, —$(CF_3)$, ethyl, propyl and cyclopropyl.

14. The compound according to claim 1, wherein for $R^{9'}$, the $(C_7\text{-}C_{10})$heterobicycle is a substituted or non-substituted $(C_7)$heterobicycle having 2 heteroatoms selected from N and S.

15. The compound according to claim 1, wherein for $R^{9'}$, the proteinogenic amino acid or non-proteinogenic amino acid is an aminooxy or hydrazide derivative of the proteinogenic or non-proteinogenic amino acid.

16. The compound according to claim 1, wherein for $R^{9'}$, the proteinogenic amino acid or non-proteinogenic amino acid is selected from the group consisting of lysine, proline, glycine, 4-hydroxyproline, 4-aminoproline, and 4-aminooxyproline.

17. The compound according to claim 1, wherein for $R^{9'}$, the peptide comprises 1 to 2000 amino acids.

18. The compound according to claim 1, wherein for $R^{9'}$, the peptide comprises 1 to 10, [proline]-[4-hydroxyproline]-[glycine] units.

19. The compound according to claim 1, wherein for $R^{9'}$, the antibody is an anti-collagen, anti-elastin, anti-fibronectin or anti-fibrillin antibody.

* * * * *

SEQUENCE LISTING

```
<160> NUMBER OF SEQ ID NOS: 7

<210> SEQ ID NO 1
<211> LENGTH: 417
<212> TYPE: PRT
<213> ORGANISM: Homo sapiens

<400> SEQUENCE: 1

Met Arg Phe Ala Trp Thr Val Leu Leu Leu Gly Pro Leu Gln Leu Cys
1               5                   10                  15

Ala Leu Val His Cys Ala Pro Pro Ala Ala Gly Gln Gln Gln Pro Pro
                20                  25                  30

Arg Glu Pro Pro Ala Ala Pro Gly Ala Trp Arg Gln Gln Ile Gln Trp
        35                  40                  45

Glu Asn Asn Gly Gln Val Phe Ser Leu Leu Ser Leu Gly Ser Gln Tyr
    50                  55                  60

Gln Pro Gln Arg Arg Arg Asp Pro Gly Ala Ala Val Pro Gly Ala Ala
65                  70                  75                  80

Asn Ala Ser Ala Gln Gln Pro Arg Thr Pro Ile Leu Leu Ile Arg Asp
                85                  90                  95

Asn Arg Thr Ala Ala Ala Arg Thr Arg Thr Ala Gly Ser Ser Gly Val
            100                 105                 110

Thr Ala Gly Arg Pro Arg Pro Thr Ala Arg His Trp Phe Gln Ala Gly
        115                 120                 125

Tyr Ser Thr Ser Arg Ala Arg Glu Ala Gly Ala Ser Arg Ala Glu Asn
    130                 135                 140

Gln Thr Ala Pro Gly Glu Val Pro Ala Leu Ser Asn Leu Arg Pro Pro
145                 150                 155                 160

Ser Arg Val Asp Gly Met Val Gly Asp Asp Pro Tyr Asn Pro Tyr Lys
                165                 170                 175

Tyr Ser Asp Asp Asn Pro Tyr Tyr Asn Tyr Tyr Asp Thr Tyr Glu Arg
            180                 185                 190

Pro Arg Pro Gly Gly Arg Tyr Arg Pro Gly Tyr Gly Thr Gly Tyr Phe
        195                 200                 205

Gln Tyr Gly Leu Pro Asp Leu Val Ala Asp Pro Tyr Tyr Ile Gln Ala
    210                 215                 220

Ser Thr Tyr Val Gln Lys Met Ser Met Tyr Asn Leu Arg Cys Ala Ala
225                 230                 235                 240

Glu Glu Asn Cys Leu Ala Ser Thr Ala Tyr Arg Ala Asp Val Arg Asp
                245                 250                 255

Tyr Asp His Arg Val Leu Leu Arg Phe Pro Gln Arg Val Lys Asn Gln
            260                 265                 270

Gly Thr Ser Asp Phe Leu Pro Ser Arg Pro Arg Tyr Ser Trp Glu Trp
        275                 280                 285

His Ser Cys His Gln His Tyr His Ser Met Asp Glu Phe Ser His Tyr
    290                 295                 300
```

Asp Leu Leu Asp Ala Asn Thr Gln Arg Arg Val Ala Glu Gly His Lys
305 310 315 320

Ala Ser Phe Cys Leu Glu Asp Thr Ser Cys Asp Tyr Gly Tyr His Arg
325 330 335

Arg Phe Ala Cys Thr Ala His Thr Gln Gly Leu Ser Pro Gly Cys Tyr
340 345 350

Asp Thr Tyr Gly Ala Asp Ile Asp Cys Gln Trp Ile Asp Ile Thr Asp
355 360 365

Val Lys Pro Gly Asn Tyr Ile Leu Lys Val Ser Val Asn Pro Ser Tyr
370 375 380

Leu Val Pro Glu Ser Asp Tyr Thr Asn Asn Val Val Arg Cys Asp Ile
385 390 395 400

Arg Tyr Thr Gly His His Ala Tyr Ala Ser Gly Cys Thr Ile Ser Pro
405 410 415

Tyr

<210> SEQ ID NO 2
<211> LENGTH: 249
<212> TYPE: PRT
<213> ORGANISM: Homo sapiens

<400> SEQUENCE: 2

Asp Asp Pro Tyr Asn Pro Tyr Lys Tyr Ser Asp Asp Asn Pro Tyr Tyr
1 5 10 15

Asn Tyr Tyr Asp Thr Tyr Glu Arg Pro Arg Pro Gly Gly Arg Tyr Arg
20 25 30

Pro Gly Tyr Gly Thr Gly Tyr Phe Gln Tyr Gly Leu Pro Asp Leu Val
35 40 45

Ala Asp Pro Tyr Tyr Ile Gln Ala Ser Thr Tyr Val Gln Lys Met Ser
50 55 60

Met Tyr Asn Leu Arg Cys Ala Ala Glu Glu Asn Cys Leu Ala Ser Thr
65 70 75 80

Ala Tyr Arg Ala Asp Val Arg Asp Tyr Asp His Arg Val Leu Leu Arg
85 90 95

Phe Pro Gln Arg Val Lys Asn Gln Gly Thr Ser Asp Phe Leu Pro Ser
100 105 110

Arg Pro Arg Tyr Ser Trp Glu Trp His Ser Cys His Gln His Tyr His
115 120 125

Ser Met Asp Glu Phe Ser His Tyr Asp Leu Leu Asp Ala Asn Thr Gln
130 135 140

Arg Arg Val Ala Glu Gly His Lys Ala Ser Phe Cys Leu Glu Asp Thr
145 150 155 160

Ser Cys Asp Tyr Gly Tyr His Arg Arg Phe Ala Cys Thr Ala His Thr
165 170 175

Gln Gly Leu Ser Pro Gly Cys Tyr Asp Thr Tyr Gly Ala Asp Ile Asp
180 185 190

Cys Gln Trp Ile Asp Ile Thr Asp Val Lys Pro Gly Asn Tyr Ile Leu
195 200 205

Lys Val Ser Val Asn Pro Ser Tyr Leu Val Pro Glu Ser Asp Tyr Thr
210 215 220

Asn Asn Val Val Arg Cys Asp Ile Arg Tyr Thr Gly His His Ala Tyr
225 230 235 240

Ala Ser Gly Cys Thr Ile Ser Pro Tyr
245

<210> SEQ ID NO 3
<211> LENGTH: 199
<212> TYPE: PRT
<213> ORGANISM: Homo sapiens

<400> SEQUENCE: 3

```
Pro Tyr Tyr Ile Gln Ala Ser Thr Tyr Val Gln Lys Met Ser Met Tyr
1               5                   10                  15

Asn Leu Arg Cys Ala Ala Glu Glu Asn Cys Leu Ala Ser Thr Ala Tyr
            20                  25                  30

Arg Ala Asp Val Arg Asp Tyr Asp His Arg Val Leu Leu Arg Phe Pro
        35                  40                  45

Gln Arg Val Lys Asn Gln Gly Thr Ser Asp Phe Leu Pro Ser Arg Pro
    50                  55                  60

Arg Tyr Ser Trp Glu Trp His Ser Cys His Gln His Tyr His Ser Met
65                  70                  75                  80

Asp Glu Phe Ser His Tyr Asp Leu Leu Asp Ala Asn Thr Gln Arg Arg
                85                  90                  95

Val Ala Glu Gly His Lys Ala Ser Phe Cys Leu Glu Asp Thr Ser Cys
            100                 105                 110

Asp Tyr Gly Tyr His Arg Arg Phe Ala Cys Thr Ala His Thr Gln Gly
        115                 120                 125

Leu Ser Pro Gly Cys Tyr Asp Thr Tyr Gly Ala Asp Ile Asp Cys Gln
    130                 135                 140

Trp Ile Asp Ile Thr Asp Val Lys Pro Gly Asn Tyr Ile Leu Lys Val
145                 150                 155                 160

Ser Val Asn Pro Ser Tyr Leu Val Pro Glu Ser Asp Tyr Thr Asn Asn
                165                 170                 175

Val Val Arg Cys Asp Ile Arg Tyr Thr Gly His His Ala Tyr Ala Ser
            180                 185                 190

Gly Cys Thr Ile Ser Pro Tyr
        195
```

<210> SEQ ID NO 4
<211> LENGTH: 527
<212> TYPE: PRT
<213> ORGANISM: Homo sapiens

<400> SEQUENCE: 4

```
Met Glu Asn Gln Glu Lys Ala Ser Ile Ala Gly His Met Phe Asp Val
1               5                   10                  15

Val Val Ile Gly Gly Gly Ile Ser Gly Leu Ser Ala Ala Lys Leu Leu
            20                  25                  30

Thr Glu Tyr Gly Val Ser Val Leu Val Leu Glu Ala Arg Asp Arg Val
        35                  40                  45

Gly Gly Arg Thr Tyr Thr Ile Arg Asn Glu His Val Asp Tyr Val Asp
    50                  55                  60

Val Gly Gly Ala Tyr Val Gly Pro Thr Gln Asn Arg Ile Leu Arg Leu
65                  70                  75                  80

Ser Lys Glu Leu Gly Ile Glu Thr Tyr Lys Val Asn Val Ser Glu Arg
                85                  90                  95

Leu Val Gln Tyr Val Lys Gly Lys Thr Tyr Pro Phe Arg Gly Ala Phe
            100                 105                 110

Pro Pro Val Trp Asn Pro Ile Ala Tyr Leu Asp Tyr Asn Asn Leu Trp
        115                 120                 125
```

```
Arg Thr Ile Asp Asn Met Gly Lys Glu Ile Pro Thr Asp Ala Pro Trp
    130                 135                 140

Glu Ala Gln His Ala Asp Lys Trp Asp Lys Met Thr Met Lys Glu Leu
145                 150                 155                 160

Ile Asp Lys Ile Cys Trp Thr Lys Thr Ala Arg Arg Phe Ala Tyr Leu
                165                 170                 175

Phe Val Asn Ile Asn Val Thr Ser Glu Pro His Glu Val Ser Ala Leu
            180                 185                 190

Trp Phe Leu Trp Tyr Val Lys Gln Cys Gly Gly Thr Thr Arg Ile Phe
        195                 200                 205

Ser Val Thr Asn Gly Gly Gln Glu Arg Lys Phe Val Gly Gly Ser Gly
    210                 215                 220

Gln Val Ser Glu Arg Ile Met Asp Leu Leu Gly Asp Gln Val Lys Leu
225                 230                 235                 240

Asn His Pro Val Thr His Val Asp Gln Ser Ser Asp Asn Ile Ile Ile
                245                 250                 255

Glu Thr Leu Asn His Glu His Tyr Glu Cys Lys Tyr Val Ile Asn Ala
            260                 265                 270

Ile Pro Pro Thr Leu Thr Ala Lys Ile His Phe Arg Pro Glu Leu Pro
        275                 280                 285

Ala Glu Arg Asn Gln Leu Ile Gln Arg Leu Pro Met Gly Ala Val Ile
    290                 295                 300

Lys Cys Met Met Tyr Tyr Lys Glu Ala Phe Trp Lys Lys Lys Asp Tyr
305                 310                 315                 320

Cys Gly Cys Met Ile Ile Glu Asp Glu Asp Ala Pro Ile Ser Ile Thr
                325                 330                 335

Leu Asp Asp Thr Lys Pro Asp Gly Ser Leu Pro Ala Ile Met Gly Phe
            340                 345                 350

Ile Leu Ala Arg Lys Ala Asp Arg Leu Ala Lys Leu His Lys Glu Ile
        355                 360                 365

Arg Lys Lys Lys Ile Cys Glu Leu Tyr Ala Lys Val Leu Gly Ser Gln
    370                 375                 380

Glu Ala Leu His Pro Val His Tyr Glu Glu Lys Asn Trp Cys Glu Glu
385                 390                 395                 400

Gln Tyr Ser Gly Gly Cys Tyr Thr Ala Tyr Phe Pro Pro Gly Ile Met
                405                 410                 415

Thr Gln Tyr Gly Arg Val Ile Arg Gln Pro Val Gly Arg Ile Phe Phe
            420                 425                 430

Ala Gly Thr Glu Thr Ala Thr Lys Trp Ser Gly Tyr Met Glu Gly Ala
        435                 440                 445

Val Glu Ala Gly Glu Arg Ala Ala Arg Glu Val Leu Asn Gly Leu Gly
    450                 455                 460

Lys Val Thr Glu Lys Asp Ile Trp Val Gln Glu Pro Glu Ser Lys Asp
465                 470                 475                 480

Val Pro Ala Val Glu Ile Thr His Thr Phe Trp Glu Arg Asn Leu Pro
                485                 490                 495

Ser Val Ser Gly Leu Leu Lys Ile Ile Gly Phe Ser Thr Ser Val Thr
            500                 505                 510

Ala Leu Gly Phe Val Leu Tyr Lys Tyr Lys Leu Leu Pro Arg Ser
        515                 520                 525
```

<210> SEQ ID NO 5
<211> LENGTH: 394

-continued

<212> TYPE: PRT
<213> ORGANISM: Homo sapiens

<400> SEQUENCE: 5

```
Met Gly Lys Glu Ile Pro Thr Asp Ala Pro Trp Glu Ala Gln His Ala
1               5                   10                  15

Asp Lys Trp Asp Lys Met Thr Met Lys Glu Leu Ile Asp Lys Ile Cys
            20                  25                  30

Trp Thr Lys Thr Ala Arg Arg Phe Ala Tyr Leu Phe Val Asn Ile Asn
        35                  40                  45

Val Thr Ser Glu Pro His Glu Val Ser Ala Leu Trp Phe Leu Trp Tyr
    50                  55                  60

Val Lys Gln Cys Gly Gly Thr Thr Arg Ile Phe Ser Val Thr Asn Gly
65                  70                  75                  80

Gly Gln Glu Arg Lys Phe Val Gly Gly Ser Gly Gln Val Ser Glu Arg
                85                  90                  95

Ile Met Asp Leu Leu Gly Asp Gln Val Lys Leu Asn His Pro Val Thr
            100                 105                 110

His Val Asp Gln Ser Ser Asp Asn Ile Ile Ile Glu Thr Leu Asn His
        115                 120                 125

Glu His Tyr Glu Cys Lys Tyr Val Ile Asn Ala Ile Pro Pro Thr Leu
    130                 135                 140

Thr Ala Lys Ile His Phe Arg Pro Glu Leu Pro Ala Glu Arg Asn Gln
145                 150                 155                 160

Leu Ile Gln Arg Leu Pro Met Gly Ala Val Ile Lys Cys Met Met Tyr
                165                 170                 175

Tyr Lys Glu Ala Phe Trp Lys Lys Lys Asp Tyr Cys Gly Cys Met Ile
            180                 185                 190

Ile Glu Asp Glu Asp Ala Pro Ile Ser Ile Thr Leu Asp Asp Thr Lys
        195                 200                 205

Pro Asp Gly Ser Leu Pro Ala Ile Met Gly Phe Ile Leu Ala Arg Lys
    210                 215                 220

Ala Asp Arg Leu Ala Lys Leu His Lys Glu Ile Arg Lys Lys Lys Ile
225                 230                 235                 240

Cys Glu Leu Tyr Ala Lys Val Leu Gly Ser Gln Glu Ala Leu His Pro
                245                 250                 255

Val His Tyr Glu Glu Lys Asn Trp Cys Glu Glu Gln Tyr Ser Gly Gly
            260                 265                 270

Cys Tyr Thr Ala Tyr Phe Pro Pro Gly Ile Met Thr Gln Tyr Gly Arg
        275                 280                 285

Val Ile Arg Gln Pro Val Gly Arg Ile Phe Phe Ala Gly Thr Glu Thr
    290                 295                 300

Ala Thr Lys Trp Ser Gly Tyr Met Glu Gly Ala Val Glu Ala Gly Glu
305                 310                 315                 320

Arg Ala Ala Arg Glu Val Leu Asn Gly Leu Gly Lys Val Thr Glu Lys
                325                 330                 335

Asp Ile Trp Val Gln Glu Pro Glu Ser Lys Asp Val Pro Ala Val Glu
            340                 345                 350

Ile Thr His Thr Phe Trp Glu Arg Asn Leu Pro Ser Val Ser Gly Leu
        355                 360                 365

Leu Lys Ile Ile Gly Phe Ser Thr Ser Val Thr Ala Leu Gly Phe Val
    370                 375                 380

Leu Tyr Lys Tyr Lys Leu Leu Pro Arg Ser
385                 390
```

<210> SEQ ID NO 6
<211> LENGTH: 520
<212> TYPE: PRT
<213> ORGANISM: Homo sapiens

<400> SEQUENCE: 6

```
Met Ser Asn Lys Cys Asp Val Val Val Val Gly Gly Gly Ile Ser Gly
1               5                   10                  15

Met Ala Ala Ala Lys Leu Leu His Asp Ser Gly Leu Asn Val Val Val
            20                  25                  30

Leu Glu Ala Arg Asp Arg Val Gly Gly Arg Thr Tyr Thr Leu Arg Asn
        35                  40                  45

Gln Lys Val Lys Tyr Val Asp Leu Gly Gly Ser Tyr Val Gly Pro Thr
    50                  55                  60

Gln Asn Arg Ile Leu Arg Leu Ala Lys Glu Leu Gly Leu Glu Thr Tyr
65                  70                  75                  80

Lys Val Asn Glu Val Glu Arg Leu Ile His His Val Lys Gly Lys Ser
                85                  90                  95

Tyr Pro Phe Arg Gly Pro Phe Pro Pro Val Trp Asn Pro Ile Thr Tyr
            100                 105                 110

Leu Asp His Asn Asn Phe Trp Arg Thr Met Asp Asp Met Gly Arg Glu
        115                 120                 125

Ile Pro Ser Asp Ala Pro Trp Lys Ala Pro Leu Ala Glu Glu Trp Asp
    130                 135                 140

Asn Met Thr Met Lys Glu Leu Leu Asp Lys Leu Cys Trp Thr Glu Ser
145                 150                 155                 160

Ala Lys Gln Leu Ala Thr Leu Phe Val Asn Leu Cys Val Thr Ala Glu
                165                 170                 175

Thr His Glu Val Ser Ala Leu Trp Phe Leu Trp Tyr Val Lys Gln Cys
            180                 185                 190

Gly Gly Thr Thr Arg Ile Ile Ser Thr Thr Asn Gly Gly Gln Glu Arg
        195                 200                 205

Lys Phe Val Gly Gly Ser Gly Gln Val Ser Glu Arg Ile Met Asp Leu
    210                 215                 220

Leu Gly Asp Arg Val Lys Leu Glu Arg Pro Val Ile Tyr Ile Asp Gln
225                 230                 235                 240

Thr Arg Glu Asn Val Leu Val Glu Thr Leu Asn His Glu Met Tyr Glu
                245                 250                 255

Ala Lys Tyr Val Ile Ser Ala Ile Pro Pro Thr Leu Gly Met Lys Ile
            260                 265                 270

His Phe Asn Pro Pro Leu Pro Met Met Arg Asn Gln Met Ile Thr Arg
        275                 280                 285

Val Pro Leu Gly Ser Val Ile Lys Cys Ile Val Tyr Tyr Lys Glu Pro
    290                 295                 300

Phe Trp Arg Lys Lys Asp Tyr Cys Gly Thr Met Ile Ile Asp Gly Glu
305                 310                 315                 320

Glu Ala Pro Val Ala Tyr Thr Leu Asp Asp Thr Lys Pro Glu Gly Asn
                325                 330                 335

Tyr Ala Ala Ile Met Gly Phe Ile Leu Ala His Lys Ala Arg Lys Leu
            340                 345                 350

Ala Arg Leu Thr Lys Glu Glu Arg Leu Lys Lys Leu Cys Glu Leu Tyr
        355                 360                 365

Ala Lys Val Leu Gly Ser Leu Glu Ala Leu Glu Pro Val His Tyr Glu
```

-continued

```
    370                 375                 380

Glu Lys Asn Trp Cys Glu Glu Gln Tyr Ser Gly Gly Cys Tyr Thr Thr
385                 390                 395                 400

Tyr Phe Pro Pro Gly Ile Leu Thr Gln Tyr Gly Arg Val Leu Arg Gln
                405                 410                 415

Pro Val Asp Arg Ile Tyr Phe Ala Gly Thr Glu Thr Ala Thr His Trp
            420                 425                 430

Ser Gly Tyr Met Glu Gly Ala Val Glu Ala Gly Glu Arg Ala Ala Arg
        435                 440                 445

Glu Ile Leu His Ala Met Gly Lys Ile Pro Glu Asp Glu Ile Trp Gln
    450                 455                 460

Ser Glu Pro Glu Ser Val Asp Val Pro Ala Gln Pro Ile Thr Thr Thr
465                 470                 475                 480

Phe Leu Glu Arg His Leu Pro Ser Val Pro Gly Leu Leu Arg Leu Ile
                485                 490                 495

Gly Leu Thr Thr Ile Phe Ser Ala Thr Ala Leu Gly Phe Leu Ala His
            500                 505                 510

Lys Arg Gly Leu Leu Val Arg Val
        515                 520


<210> SEQ ID NO 7
<211> LENGTH: 411
<212> TYPE: PRT
<213> ORGANISM: Homo sapiens

<400> SEQUENCE: 7

Met Ala Ala Ala Lys Leu Leu His Asp Ser Gly Leu Asn Val Val Val
1               5                   10                  15

Leu Glu Ala Arg Asp Arg Val Gly Gly Arg Thr Tyr Thr Leu Arg Asn
            20                  25                  30

Gln Lys Val Lys Tyr Val Asp Leu Gly Gly Ser Tyr Val Gly Pro Thr
        35                  40                  45

Gln Asn Arg Ile Leu Arg Leu Ala Lys Glu Leu Gly Leu Glu Thr Tyr
    50                  55                  60

Lys Val Asn Glu Val Glu Arg Leu Ile His His Val Lys Gly Lys Ser
65                  70                  75                  80

Tyr Pro Phe Arg Gly Pro Phe Pro Pro Val Trp Asn Pro Ile Thr Tyr
                85                  90                  95

Leu Asp His Asn Asn Phe Trp Arg Thr Met Asp Asp Met Gly Arg Glu
            100                 105                 110

Ile Pro Ser Asp Ala Pro Trp Lys Ala Pro Leu Ala Glu Glu Trp Asp
        115                 120                 125

Asn Met Thr Met Lys Glu Leu Leu Asp Lys Leu Cys Trp Thr Glu Ser
    130                 135                 140

Ala Lys Gln Leu Ala Thr Leu Phe Val Asn Leu Cys Val Thr Ala Glu
145                 150                 155                 160

Thr His Glu Val Ser Ala Leu Trp Phe Leu Trp Tyr Val Lys Gln Cys
                165                 170                 175

Gly Gly Thr Thr Arg Ile Ile Ser Thr Thr Asn Gly Gly Gln Glu Arg
            180                 185                 190

Lys Phe Val Gly Gly Ser Gly Gln Val Ser Glu Arg Ile Met Asp Leu
        195                 200                 205

Leu Gly Asp Arg Val Lys Leu Glu Arg Pro Val Ile Tyr Ile Asp Gln
    210                 215                 220
```

-continued

```
Thr Arg Glu Asn Val Leu Val Glu Thr Leu Asn His Glu Met Tyr Glu
225                 230                 235                 240

Ala Lys Tyr Val Ile Ser Ala Ile Pro Pro Thr Leu Gly Met Lys Ile
                245                 250                 255

His Phe Asn Pro Pro Leu Pro Met Met Arg Asn Gln Met Ile Thr Arg
            260                 265                 270

Val Pro Leu Gly Ser Val Ile Lys Cys Ile Val Tyr Tyr Lys Glu Pro
        275                 280                 285

Phe Trp Arg Lys Lys Asp Tyr Cys Gly Thr Met Ile Ile Asp Gly Glu
    290                 295                 300

Glu Ala Pro Val Ala Tyr Thr Leu Asp Asp Thr Lys Pro Glu Gly Asn
305                 310                 315                 320

Tyr Ala Ala Ile Met Gly Phe Ile Leu Ala His Lys Ala Arg Lys Leu
                325                 330                 335

Ala Arg Leu Thr Lys Glu Glu Arg Leu Lys Lys Leu Cys Glu Leu Tyr
            340                 345                 350

Ala Lys Val Leu Gly Ser Leu Glu Ala Leu Glu Gly Ser Thr Pro Ala
        355                 360                 365

Ser Gly Gln Asp Leu Leu Cys Arg His Arg Asp Cys His Thr Leu Glu
    370                 375                 380

Arg Leu His Gly Gly Gly Cys Arg Gly Arg Gly Glu Ser Ser Pro Arg
385                 390                 395                 400

Asp Pro Ala Cys His Gly Glu Asp Ser Arg Gly
                405                 410
```